United States Patent
Miles et al.

(10) Patent No.: US 9,408,698 B2
(45) Date of Patent: Aug. 9, 2016

(54) METHOD INCORPORATING COMPUTER-IMPLEMENTED STEPS, A COMPUTING DEVICE, A COMPUTER READABLE STORAGE MEDIUM, AND A CLIENT COMPUTING DEVICE FOR MODELLING THE ALIGNMENT OF AN ORTHOPAEDIC IMPLANT FOR A JOINT OF A PATIENT

(71) Applicant: OPTIMIZED ORTHO PTY LTD, Pymble (AU)

(72) Inventors: Brad Peter Miles, Walsh Bay (AU); Peter Bede O'Connor, Walsh Bay (AU); Justin Roe, Walsh Bay (AU); Brett Fritsch, Walsh Bay (AU); Len Walter, Walsh Bay (AU); Ed Marel, Walsh Bay (AU); Michael Solomon, Walsh Bay (AU); Brian Cheung, Mission Viego, CA (US); Milton Scott Bergeon, Mission Viejo, CA (US); James William Pierrepont, Cremorne (AU)

(73) Assignee: CORIN LIMITED, Cirencester (GB)

(*) Notice: Subject to any disclaimer, the term of this patent is extended or adjusted under 35 U.S.C. 154(b) by 0 days.

(21) Appl. No.: 14/602,162

(22) Filed: Jan. 21, 2015

(65) Prior Publication Data

US 2015/0227711 A1 Aug. 13, 2015

Related U.S. Application Data

(62) Division of application No. 14/000,858, filed as application No. PCT/AU2012/000179 on Feb. 24, 2012, now Pat. No. 8,983,813.

(51) Int. Cl.
*G06F 17/50* (2006.01)
*A61F 2/30* (2006.01)
*G06F 19/00* (2011.01)

(52) U.S. Cl.
CPC .............. *A61F 2/30942* (2013.01); *A61B 34/10* (2016.02); *A61B 90/06* (2016.02);
(Continued)

(58) Field of Classification Search
USPC ............................ 703/2; 434/27; 606/62, 304
See application file for complete search history.

(56) References Cited

U.S. PATENT DOCUMENTS

| | | |
|---|---|---|
| 8,983,813 B2 | 3/2015 | Miles et al. |
| 2005/0197814 A1 | 9/2005 | Aram |

(Continued)

FOREIGN PATENT DOCUMENTS

WO 2010120990 A1 10/2010

OTHER PUBLICATIONS

Extended European Search Report from corresponding European Application No. 12749104.1, dated May 13, 2015, 6 pages.
(Continued)

*Primary Examiner* — Thai Phan
(74) *Attorney, Agent, or Firm* — Innovation Capital Law Group, LLP; Vic Lin

(57) ABSTRACT

The present disclosure relates to a method incorporating computer-implemented steps, a computing device, a computer readable storage medium, and a client computing device for modelling the alignment of an orthopedic implant for a joint of a patient. The method comprises the computer-implemented steps of being responsive to patient specific information data for deriving patient data, where the patient specific information data is indicative of one or more dynamic characteristics, and being responsive to the patient data for providing 3D model data of the joint, such that the 3D model data shows the orthopedic implant in an alignment configuration based on the patient specific information data.

37 Claims, 29 Drawing Sheets

(52) U.S. Cl.
CPC ............. *G06F19/3437* (2013.01); *A61B 34/30* (2016.02); *A61B 2034/102* (2016.02); *A61B 2034/105* (2016.02); *A61B 2090/3945* (2016.02); *A61F 2002/30952* (2013.01); *G06F 17/5009* (2013.01)

(56) References Cited

U.S. PATENT DOCUMENTS

| | | |
|---|---|---|
| 2007/0288030 A1 | 12/2007 | Metzger et al. |
| 2008/0300597 A1 | 12/2008 | Morgan et al. |
| 2010/0076563 A1 | 3/2010 | Otto et al. |
| 2010/0331895 A1 | 12/2010 | Linke |
| 2011/0029091 A1 | 2/2011 | Bojarski |
| 2012/0277746 A1 | 11/2012 | Morgan et al. |
| 2013/0017507 A1 | 1/2013 | Moffson et al. |
| 2013/0034838 A1 | 2/2013 | Davis et al. |

OTHER PUBLICATIONS

China Office Action from corresponding Chinese Application o. 201280020546.2, dated Apr. 20 2015, 6 pages.
Australia Patent Examination Report dated Aug. 2, 2015 from corresponding Australian Patent Application No. 2012220362, 3 pages.
Japan Office Action dated Nov. 17, 2015 from corresponding Japanese Application No. 2013-554751, 7 pages.
Notice of Allowance dated Feb. 12, 2016 from related U.S. Appl. No. 14/602,172, 10 pages.

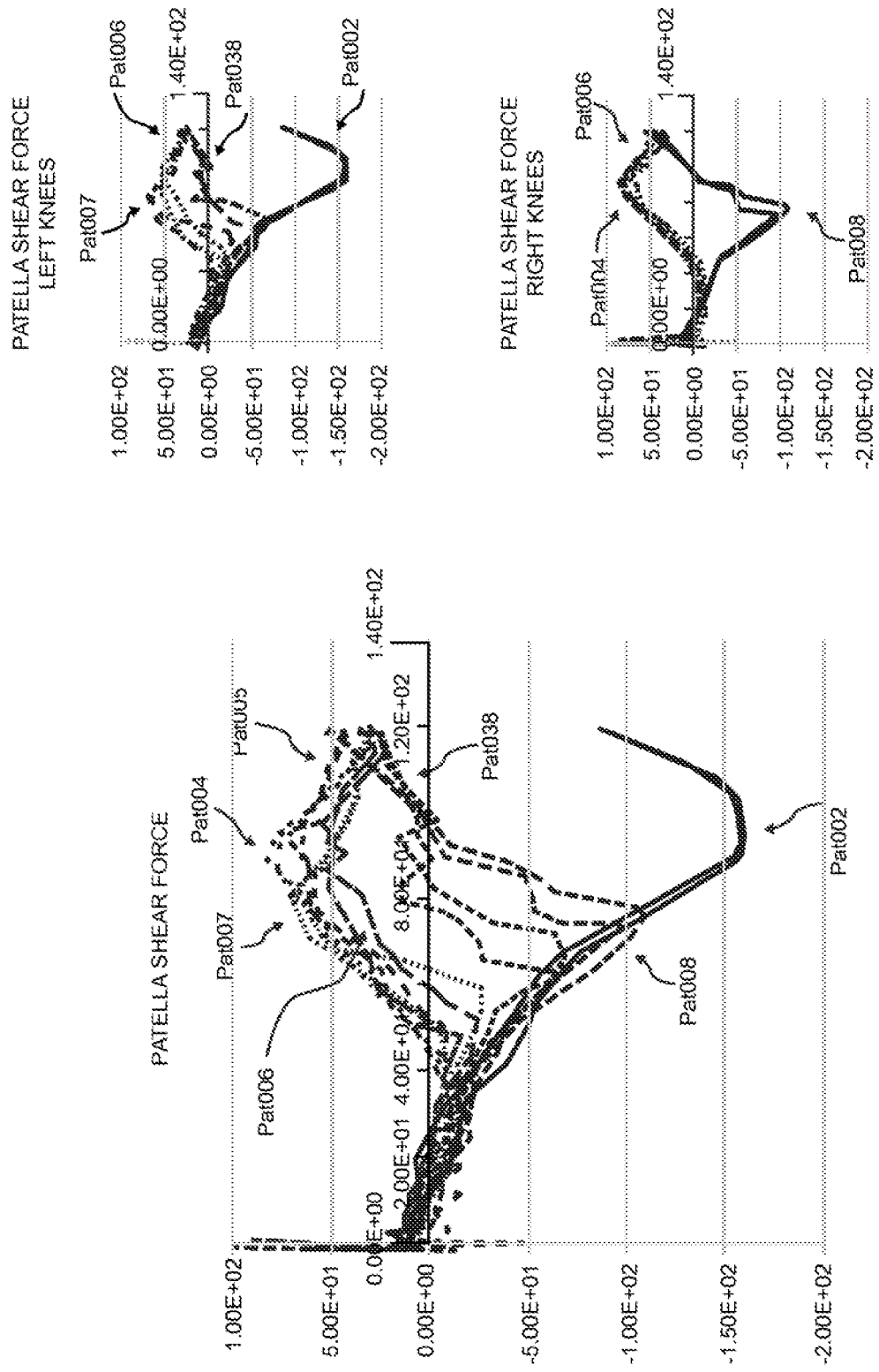

| IMPLANT | POST-IMPLANT ACTIVITY | | |
|---|---|---|---|
| | Tennis | Golf | Skiing |
| X | - | - | - |
| Y | - | - | - |
| Z | ZA | ZB | ZC |

METHOD INCORPORATING COMPUTER-IMPLEMENTED STEPS, A COMPUTING DEVICE, A COMPUTER READABLE STORAGE MEDIUM, AND A CLIENT COMPUTING DEVICE FOR MODELLING THE ALIGNMENT OF AN ORTHOPAEDIC IMPLANT FOR A JOINT OF A PATIENT

RELATED APPLICATIONS

This application is a divisional of U.S. patent application Ser. No. 14/000,858, filed on Aug. 21, 2013, issued as U.S. Pat. No. 8,983,813 on Mar. 17, 2015, and entitled COMPUTER-IMPLEMENTED METHOD, A COMPUTING DEVICE AND A COMPUTER READABLE STORAGE MEDIUM FOR PROVIDING ALIGNMENT INFORMATION DATA FOR THE ALIGNMENT OF AN ORTHOPAEDIC IMPLANT FOR A JOINT OF A PATIENT which is the National Stage of International PCT/AU2012/000179, filed on Feb. 24, 2012 which claims the benefit of Foreign Patent Application AU2011900673, filed on Feb. 25, 2011, the disclosure of which is incorporated by reference herein.

FIELD OF THE INVENTION

The present invention relates to a method comprising computer-implemented steps, a computing device, a computer readable storage medium, and a client computing device for providing alignment information data for modelling the alignment of an orthopaedic implant for a joint of a patient.

The invention has been developed primarily for use in modelling the alignment of an orthopaedic implant for a knee or hip joint of a patient, and providing tools for assisting with the modelling of the alignment of an orthopaedic implant for a knee or hip joint of a patient, and will be described hereinafter with reference to this application. However, it will be appreciated that the invention is not limited to this particular field of use.

BACKGROUND OF THE INVENTION

Replacing joints with orthopaedic implants due to injury or degeneration has been commonplace for many years. A more fitness-driven outlook and active lifestyle pursued by the older generation is giving rise to an increasing frequency of joint degeneration or injury from an earlier age.

As such, joints, such as knee and hip joints, must be surgically repaired or, in some cases, totally replaced. The current method for replacing joints typically involves mechanical axis alignment of a joint for placing the orthopaedic implant. This involves taking a number of stationary physical measurements to align the orthopaedic implant to the patient's primary mechanical weight bearing axis. For example, for a knee joint, this involves aligning the orthopaedic implant based on a mechanical weight bearing axis that intersects the centre of the hip, the centre of the knee and the centre of the ankle.

Current standard surgical practice is to use instruments (mechanical and computer driven) to align implants to reference points. The mechanical axis in knees and an analogous geometrical reference frame in hips is used (for example, 45 degrees cup inclination, 15 to 20 degrees cup ante-version, neutral femoral stem position).

It is also known to try to adjust the range of motion of the joint by varying the implant position. This is either done manually, through the expert handling/feel of the surgeon, or, through the computed identification of a central axis of the range of motion.

It is also noted that commercially available computer navigation systems currently provide information about mechanical alignment and the ability to customize implant position from this information.

Total joint replacements that are aligned using mechanical axis alignment, although showing favourable results for survivorship and longevity, are often disappointing when measured in terms of functional patient outcomes. That is, the joints are not suited to activities that a person may wish to undertake, therefore causing pain and discomfort to the person. In some cases, such activities will cause the implant to fail.

People with total joint replacements rarely achieve the lifestyle equivalents of their non-arthritic peers. As such, there is a lack of techniques that demonstrate improvements in patient function and quality of life, after a total joint replacement.

The problems mentioned above can be attributed to the lack of patient specificity offered by 'off the shelf' orthopaedic implant designs. All patients receive the same implant designs in the same position regardless of their age, gender, activity level or body shape. However, not all patients are the same.

Patient diversity has recently received much attention within the orthopaedic literature. A topical example is the difference in the size of male and female knees. This has led total knee replacement (TKR) manufacturers to introduce separate size ranges for male and female implants.

This only goes some of the way to addressing the diversity encountered by orthopaedic surgeons in practice today. Many published studies highlight many more morphological differences that exist within sampled patient populations.

A pertinent example is that of the slope of patients' tibial plateaus. Males have been measured on average to have significantly different posterior slopes to that measured in females. Furthermore, there has been significant inter-sex variation observed. Yet manufacturers recommend to surgeons implanting knee replacements that they align the tibial components with a one size fits all 'standard' recommended prostheses alignment. This alignment recommendation does not change if you are male or female, whether you have a severe tibial slope or a mild tibial slope, whether you are short or tall, or whether you have a high or low demand lifestyle.

This is not just the case for tibial component alignment. All of the alignment parameters generally recommended to surgeons are one size fits all generalisations. This one size fits approach to TKR surgery contributes to the relatively poor functional outcomes.

Similar generalisations can be found in the hip replacement arena. The 'gold standard' acetabular cup position for all patients is defined to be forty-five degrees of inclination and twenty degrees of ante version with reference to the anterior pelvic plane. This standard alignment becomes inappropriate when a patient presents with an anatomical variation, such as, pelvic tilt, pelvic mobility or pelvic stiffness.

Examples of processes for achieving mechanical axis alignment in total knee replacement surgery using imaging data and rapid prototype manufacturing techniques include: Prophecy™ (Wright Medical Technology, Inc.), Trumatch™ (DePuy Orthopaedics, Inc. a Johnson & Johnson Company), Signature™ Personalized Total Knee Replacement (Biomet, Inc.), MyKnee™ (Medacta, International SA), Zimmer™

Patient Specific Instruments (Zimmer, Inc.), Otis Knee™ (OtisMed, Corp.), and Visionaire™ (Smith & Nephew, Inc.), amongst others.

Examples of processes for achieving mechanical axis alignment in total knee replacement surgery using computer navigation software include: eNact Knee Navigation System™ (Stryker) and BrainLab™ Knee Navigation (BrainLab, Inc.).

Examples of processes for achieving mechanical axis alignment in total knee replacement surgery using robotics systems include: MAKOplasty™ Partial Knee Resurfacing (Mako Surgical Corp.).

However, as with known alignment processes, there is no factoring into the processing of, amongst others, age, gender, activity level or body shape which ultimately will have an effect on how a person will respond to a particular alignment.

The present invention seeks to provide a computer-implemented method, a computing device, and a computer readable storage medium for providing alignment information data for the alignment of an orthopaedic implant for a joint of a patient, which will overcome or substantially ameliorate at least some of the deficiencies of the prior art, or to at least provide an alternative.

It is to be understood that, if any prior art information is referred to herein, such reference does not constitute an admission that the information forms part of the common general knowledge in the art, in Australia or any other country.

SUMMARY OF THE INVENTION

According to one aspect of the present invention, there is provided a computer-implemented method for providing alignment information data for the alignment of an orthopaedic implant for a joint of a patient, the computer-implemented method comprising the steps of:
  being responsive to patient specific information data for deriving patient data, the patient specific information data being indicative of one or more dynamic characteristics; and
  being responsive to the patient data for providing the alignment information data for the alignment of the orthopaedic implant.

Advantageously, the orthopaedic implant can be accurately aligned to fit the patient's joint according to alignment information data specific to the patient.

Preferably, the alignment information data comprises actual 3D model data of the joint.

Advantageously, the alignment information data comprising 3D model data of the patient's joint ensures accurate alignment of the orthopaedic implant to fit the joint.

Preferably, the alignment information data comprises one or more of: location information data for the orthopaedic implant; and orientation information data for the orthopaedic implant.

Advantageously, the alignment information data comprising location information data and orientation information data for the orthopaedic implant, ensures that the orthopaedic implant can be accurately located and oriented relative to the patient's joint.

Preferably, the patient specific information data comprises patient acquired data indicative of one or more desired post-implant activities.

Advantageously, the orthopaedic implant can be accurately aligned to fit the patient's joint to enable the patient to form one or more desired post-implant activities.

Preferably, the one or more dynamic characteristics comprise a virtual prediction based on one or more of: joint kinematics data; joint loading data; and joint articulation behaviour data during desired post-implant activities.

Advantageously, the orthopaedic implant can be accurately aligned to fit the patient's joint by virtue of the virtual prediction of the joint kinematics data, joint loading data, and joint articulation behaviour data, thereby enabling the patient to perform the corresponding one or more desired post-implant activities.

Preferably, the virtual prediction comprises a computer model prediction.

Advantageously, the virtual prediction of the joint kinematics data, joint loading data, and joint articulation behaviour data is provided as a computer model prediction to predict the performance of the orthopaedic implant for performing the one or more desired post-implant activities.

Preferably, the patient specific information data is indicative of one or more static characteristics.

Advantageously, the orthopaedic implant can be accurately aligned to fit the patient's joint by virtue of deriving alignment information data specific to the patient's joint that takes into consideration one or more static characteristics of the patient's joint.

Preferably, the one or more static characteristics comprise one or more load bearing axes of a biomechanical reference frame.

Advantageously, the orthopaedic implant can be accurately aligned to fit the patient's joint by virtue of deriving alignment information data specific to the patient's joint that takes into consideration one or more load bearing axes of a biomechanical reference frame of the patient's joint.

Preferably, the one or more load bearing axes of the biomechanical reference frame comprises a primary load bearing axis.

Advantageously, the orthopaedic implant can be accurately aligned to fit the patient's joint by virtue of deriving alignment information data specific to the patient's joint that takes into consideration the primary load bearing axis of the patient's joint.

Preferably, the one or more static characteristics comprise one or more load bearing axes of at least one reference frame of the group of biomechanical reference frames comprising: an acetabular reference frame, a femoral reference frame, a tibial reference frame, and a spinal reference frame.

Preferably, the patient specific information data comprises 2D imaging data.

Advantageously, the orthopaedic implant can be accurately aligned to fit the patient's joint by virtue of deriving alignment information data that takes into consideration 2D imaging data of the patient's joint.

Preferably, the 2D imaging data comprises one or more of: X-Ray data and visual fluoroscopy data.

Preferably, the patient specific information data comprises 3D imaging data.

Advantageously, the orthopaedic implant can be accurately aligned to fit the patient's joint by virtue of deriving alignment information data that takes into consideration 3D imaging data of the patient's joint.

Preferably, the 3D imaging data comprises one or more of: Magnetic Resonance Imaging (MRI) data, Computed Tomography (CT) data, ultrasound data, radiological data, and motion capture data.

Preferably, the patient specific information data comprises 4D imaging data.

Advantageously, the orthopaedic implant can be accurately aligned to fit the patient's joint by virtue of deriving alignment information data that takes into consideration 4D imaging data of the patient's joint.

Preferably, the 4D imaging data comprises motion capture data.

Preferably, the patient specific information data comprises 2D and 3D imaging data.

Advantageously, the orthopaedic implant can be accurately aligned to fit the patient's joint by virtue of deriving alignment information data that takes into consideration both 2D and 3D imaging data of the patient's joint.

Preferably, the patient specific information data comprises data indicative of one or more physical characteristics of the patient.

Advantageously, the orthopaedic implant can be accurately aligned to fit the patient's joint by virtue of deriving alignment information data that takes into consideration one or more physical characteristics of the patient.

Preferably, the one or more physical characteristics comprises one or more of: age data, gender data, height data, weight data, activity level data, BMI data, body condition data, and body shape data.

Preferably, the computer-implemented method further comprises the steps of:
  determining a set of possible alignment information data according to the patient data and patient acquired data, the patient acquired data being indicative of one or more desired post-implant activities, the patient acquired data comprising post-implant activities preference data; and
  selecting the alignment information data from the set of possible alignment information data according to the post-implant activities preference data.

Advantageously, the orthopaedic implant can be accurately aligned to fit the patient's joint by virtue of deriving alignment information data that takes into consideration the patient's preference for performing one or more desired post-implant activities.

Preferably, the post-implant activities preference data is a preference ratio being indicative of comparative patient preference for the one or more desired post-implant activities.

Advantageously, the orthopaedic implant can be accurately aligned to fit the patient's joint by virtue of deriving alignment information data that takes into consideration comparative patient preference for performing the one or more desired post-implant activities.

Preferably, the computer-implemented method further comprises the step of:
  accessing a database of library alignment information data, wherein the alignment information data is further selected according to the library alignment information data.

Advantageously, the orthopaedic implant can be accurately aligned to fit the patient's joint by virtue of deriving alignment information data that takes into consideration library alignment information data for performing the one or more desired post-implant activities.

Preferably, the library alignment information data comprises data relating to a group of available orthopaedic implants for performing at least one of the one or more desired post-implant activities.

Advantageously, the orthopaedic implant can be accurately aligned to fit the patient's joint by virtue of deriving alignment information data that takes into consideration library alignment information data that relates to a group of available orthopaedic implants for performing at least one of the one or more desired post-implant activities.

Preferably, the library alignment information data comprises data relating to a group of patients fitted with an orthopaedic implant for performing at least one of the one or more desired post-implant activities.

Advantageously, the orthopaedic implant can be accurately aligned to fit the patient's joint by virtue of deriving alignment information data that takes into consideration library alignment information data that relates to a group of patients fitted with an orthopaedic implant for performing at least one of the one or more desired post-implant activities.

According to another aspect of the present invention, there is provided a method of controlling an alignment system to align an orthopaedic implant according to alignment information data generated by the computer-implemented method as defined in any one of the preceding paragraphs.

Advantageously, the orthopaedic implant can be accurately aligned to fit the patient's joint using an alignment system according to the alignment information data derived above.

Preferably, the alignment system is selected from a group of alignment systems comprising: a robotic alignment system, a haptic feedback alignment system, and a computer-assisted alignment system.

Advantageously, the orthopaedic implant can be accurately aligned to fit the patient's joint using either a robotic alignment system, a haptic feedback alignment system, or a computer-assisted alignment system according to the alignment information data derived above.

According to another aspect of the present invention, there is provided a computing device for providing alignment information data for the alignment of an orthopaedic implant for a joint of a patient, the computing device comprising:
  a processor for processing digital data;
  a memory device for storing digital data including computer program code and being coupled to the processor via a bus; and
  a data interface for sending and receiving digital data and being coupled to the processor via the bus, wherein the processor is controlled by the computer program code to:
    receive, via the data interface, patient specific information data being indicative of one or more dynamic characteristics;
    calculate patient data according to the patient specific information data; and
    calculate the alignment information data for the orthopaedic implant according to the patient data.

Preferably, the alignment information data comprises actual 3D model data of the joint.

Preferably, the alignment information data comprises one or more of: location information data for the orthopaedic implant; and orientation information data for the orthopaedic implant.

Preferably, the patient specific information data comprises patient acquired data indicative of one or more desired post-implant activities.

Preferably, the one or more dynamic characteristics comprises a virtual prediction based on one or more of: joint kinematics data; joint loading data; and joint articulation behaviour data during desired post-implant activities.

Preferably, the virtual prediction comprises a computer model prediction.

Preferably, the patient specific information data is indicative of one or more static characteristics.

Preferably, the one or more static characteristics comprise one or more load bearing axes of a biomechanical reference frame.

Preferably, the one or more load bearing axes of the biomechanical reference frame comprises a primary load bearing axis.

Preferably, the one or more static characteristics comprise one or more load bearing axes of at least one reference frame of a biomechanical reference frame comprising: an acetabular reference frame, a femoral reference frame, a tibial reference frame, and a spinal reference frame.

Preferably, the patient specific information data comprises 2D imaging data.

Preferably, the 2D imaging data comprises one or more of: X-Ray data and visual fluoroscopy data.

Preferably, the patient specific information data comprises 3D imaging data.

Preferably, the 3D imaging data comprises one or more of: Magnetic Resonance Imaging (MRI) data, Computed Tomography (CT) data, ultrasound data, radiological data, and motion capture data.

Preferably, the patient specific information data comprises 4D imaging data.

Preferably, the 4D imaging data comprises motion capture data.

Preferably, the patient specific information data comprises 2D and 3D imaging data.

Preferably, the patient specific information data comprises data indicative of one or more physical characteristics of the patient.

Preferably, the one or more physical characteristics comprises one or more of: age data, gender data, height data, weight data, activity level data, BMI data, body condition data, and body shape data.

Preferably, the processor is further controlled by the computer program code to:
  receive, via the data interface, patient acquired data being indicative of one or more desired post-implant activities, the patient acquired data comprising post-implant activities preference data;
  calculate a set of possible alignment information data according to the patient data and the patient acquired data; and
  select the alignment information data from the set of possible alignment information data according to the post-implant activities preference data.

Preferably, the post-implant activities preference data is a preference ratio being indicative of comparative patient preference for the one or more desired post-implant activities.

Preferably, the computing device further comprises a database for storing digital data including library alignment information data, the database being coupled to the processor, wherein the processor is further controlled by the computer program code to:
  load, from the database, the library alignment information data, wherein the alignment information data is further selected according to the library alignment information data.

Preferably, the library alignment information data comprises data relating to a group of available orthopaedic implants for performing at least one of the one or more desired post-implant activities.

Preferably, the library alignment information data comprises data relating to a group of patients fitted with an orthopaedic implant for performing at least one of the one or more desired post-implant activities.

According to another aspect of the present invention, there is provided a computer readable storage medium comprising computer program code instructions, being executable by a computer, for:

receiving, via a data interface, patient specific information data indicative of one or more dynamic characteristics;
  calculating patient data according to the patient specific information data; and
  calculating alignment information data for an orthopaedic implant according to the patient data.

Preferably, the alignment information data comprises actual 3D model data of the joint.

Preferably, the alignment information data comprises one or more of: location information data for the orthopaedic implant; and orientation information data for the orthopaedic implant.

Preferably, the patient specific information data comprises patient acquired data indicative of one or more desired post-implant activities.

Preferably, the one or more dynamic characteristics comprise a virtual prediction based on one or more of: joint kinematics data; joint loading data; and joint articulation behaviour data during desired post-implant activities.

Preferably, the virtual prediction comprises a computer model prediction.

Preferably, the patient specific information data is indicative of one or more static characteristics.

Preferably, the one or more static characteristics comprise one or more load bearing axes of a biomechanical reference frame.

Preferably, the one or more load bearing axes of the biomechanical reference frame comprises a primary load bearing axis.

Preferably, the one or more static characteristics comprise one or more load bearing axes of at least one reference frame of a biomechanical reference frame comprising: an acetabular reference frame, a femoral reference frame, a tibial reference frame, and a spinal reference frame.

Preferably, the patient specific information data comprises 2D imaging data.

Preferably, the 2D imaging data comprises one or more of: X-Ray data and visual fluoroscopy data.

Preferably, the patient specific information data comprises 3D imaging data.

Preferably, the 3D imaging data comprises one or more of: Magnetic Resonance Imaging (MRI) data, Computed Tomography (CT) data, ultrasound data, radiological data, and motion capture data.

Preferably, the patient specific information data comprises 4D imaging data.

Preferably, the 4D imaging data comprises motion capture data.

Preferably, the patient specific information data comprises 2D and 3D imaging data.

Preferably, the patient specific information data comprises data indicative of one or more physical characteristics of the patient.

Preferably, the one or more physical characteristics comprises one or more of: age data, gender data, height data, weight data, activity level data, BMI data, body condition data, and body shape data.

Preferably, the computer readable storage medium further comprises instructions for:
  receiving, via a data interface, patient acquired data being indicative of one or more desired post-implant activities, the patient acquired data comprising post-implant activities preference data;
  calculating a set of possible alignment information data according to the patient data and the patient acquired data; and selecting the alignment information data from the set of possible alignment information data according to the post-implant activities preference data.

Preferably, the post-implant activities preference data is a preference ratio being indicative of comparative patient preference for the one or more desired post-implant activities.

Preferably, the computer readable storage medium further comprises instructions for:
loading, from a database, library alignment information data, wherein the alignment information data is further selected according to the library alignment information data.

Preferably, the library alignment information data comprises data relating to a group of available orthopaedic implants for performing at least one of the one or more desired post-implant activities.

Preferably, the library alignment information data comprises data relating to a group of patients fitted with an orthopaedic implant for performing at least one of the one or more desired post-implant activities.

According to another aspect of the present invention, there is provided a client computing device comprising an interface for sending and receiving digital data and being coupled, across a data link, to a computing device as defined in any one of the preceding paragraphs, wherein the interface is adapted for sending and receiving digital data as referred to in any one of the preceding paragraphs.

According to another aspect of the present invention, there is provided a computer-implemented method for selecting an orthopaedic implant for a joint of a patient from a group of available orthopaedic implants, the computer-implemented method comprising the steps of:
obtaining alignment information data for a patient according to the computer-implemented method as defined in any one of the preceding paragraphs; and
being responsive to the alignment information data for selecting the orthopaedic implant from the group of available orthopaedic implants.

Advantageously, the orthopaedic implant can be selected from the group of available orthopaedic implants to fit the patient's joint according to the alignment information data specific to the patient.

Preferably, the computer-implemented method further comprises the step of:
being responsive to the selected orthopaedic implant for updating a library alignment information database with the alignment information data.

Advantageously, the library alignment information database can be updated with the alignment information data associated with the joint of the patient once a suitable orthopaedic implant has been selected from the group of available orthopaedic implants to fit the patient's joint according to the specific alignment information data.

According to another aspect of the present invention, there is provided a computing device for selecting an orthopaedic implant for a joint of a patient from a group of available orthopaedic implants, the computing device comprising:
a processor for processing digital data;
a memory device for storing digital data including computer program code and being coupled to the processor via a bus; and
a data interface for sending and receiving digital data and being coupled to the processor via the bus, wherein the processor is controlled by the computer program code to:
receive alignment information data for a patient according to the computer-implemented method as defined in any one of the preceding paragraphs; and
select the orthopaedic implant from the group of available orthopaedic implants according to the alignment information data.

Preferably, the computing device further comprises a database for storing digital data including alignment information data, the database being coupled to the processor, wherein the processor is further controlled by the computer program code to:
update the database with the alignment information data according to the selected orthopaedic implant.

According to another aspect of the present invention, there is provided a computer readable storage medium comprising computer program code instructions, being executable by a computer, for:
receiving alignment information data for a patient according to the computer-implemented method as defined in any one of the preceding paragraphs; and
selecting an orthopaedic implant from a group of available orthopaedic implants according to the alignment information data.

Preferably, the computer readable storage medium further comprises instructions for:
updating a database with the alignment information data according to the selected orthopaedic implant.

According to another aspect of the present invention, there is provided a client computing device comprising an interface for sending and receiving digital data and being coupled, across a data link, to a computing device as defined in any one of the preceding paragraphs, wherein the interface is adapted for sending and receiving digital data as referred to in any one of the preceding paragraphs.

According to another aspect of the present invention, there is provided a computer-implemented method for aligning an orthopaedic implant for a joint of a patient, the computer-implemented method comprising the steps of:
obtaining alignment information data according to the computer-implemented method as defined in any one of the preceding paragraphs; and
being responsive to the alignment information data, causing the orthopaedic implant to be aligned relative to the joint of the patient.

Advantageously, the orthopaedic implant can be accurately aligned relative to the patient's joint according to the obtained alignment information data specific to the patient.

Preferably, the orthopaedic implant is aligned by an alignment system that receives the alignment information data.

Advantageously, the orthopaedic implant can be accurately aligned to fit the patient's joint using an alignment system according to the alignment information data derived above.

Preferably, the alignment system is selected from a group of alignment systems comprising: a robotic alignment system, a haptic feedback alignment system, and a computer-assisted alignment system.

Advantageously, the orthopaedic implant can be accurately aligned to fit the patient's joint using either a robotic alignment system, a haptic feedback alignment system, or a computer-assisted alignment system according to the alignment information data derived above.

Preferably, the computer-implemented method further comprises the step of:
being responsive to the aligned orthopaedic implant for updating a library alignment information database with the alignment information data.

Advantageously, the library alignment information database can be updated with the alignment information data associated with the joint of the patient once the orthopaedic implant has been aligned to fit the patient's joint according to the specific alignment information data.

According to another aspect of the present invention, there is provided a computing device for aligning an orthopaedic implant for a joint of a patient, the computing device comprising:

a processor for processing digital data;
a memory device for storing digital data including computer program code and being coupled to the processor via a bus; and
a data interface for sending and receiving digital data and being coupled to the processor via the bus, wherein the processor is controlled by the computer program code to:
receive, via the data interface, alignment information data for a patient according to the computer-implemented method as defined in any one of the preceding paragraphs; and
send, via the data interface, the alignment information data to an alignment system for aligning the orthopaedic implant relative to the joint of the patient.

Preferably, the alignment system is selected from a group of alignment systems comprising: a robotic alignment system, a haptic feedback alignment system; and a computer-assisted alignment system.

Preferably, the computing device further comprises a database for storing digital data including alignment information data, the database being coupled to the processor, wherein the processor is further controlled by the computer program code to:
update the database with the alignment information data according to the aligned orthopaedic implant.

According to another aspect of the present invention, there is provided a computer readable storage medium comprising computer program code instructions, being executable by a computer, for:
receiving, via a data interface, alignment information data for a patient according to the computer-implemented method as defined in any one of the preceding paragraphs; and
sending, via the data interface, the alignment information data to an alignment system for aligning the orthopaedic implant relative to the joint of the patient.

Preferably, the alignment system is selected from a group of alignment systems comprising: a robotic alignment system, a haptic feedback alignment system, and a computer-assisted alignment system.

Preferably, the computer readable storage medium further comprises instructions for:
updating a database with the alignment information data according to the aligned orthopaedic implant.

According to another aspect of the present invention, there is provided a client computing device comprising an interface for sending and receiving digital data and being coupled, across a data link, to a computing device as defined in any one of the preceding paragraphs, wherein the interface is adapted for sending and receiving digital data as referred to in any one of the preceding paragraphs.

According to another aspect of the present invention, there is provided a computer-implemented method for modelling the alignment of an orthopaedic implant for a joint of a patient, the computer-implemented method comprising the steps of:

being responsive to patient specific information data for deriving patient data, the patient specific information data being indicative of one or more dynamic characteristics; and
being responsive to the patient data for providing 3D model data of the joint, such that the 3D model data shows the orthopaedic implant in an alignment configuration based on the patient specific information data.

Advantageously, the alignment configuration of the orthopaedic implant can be accurately modelled for fitting the orthopaedic implant to the patient's joint by virtue of the patient specific information data.

Preferably, the one or more dynamic characteristics comprise a virtual prediction based on one or more of: joint kinematics data; joint loading data; and joint articulation behaviour data during desired post-implant activities.

Advantageously, the alignment configuration of the orthopaedic implant can be accurately modelled for fitting the orthopaedic implant to the patient's joint by virtue of the virtual prediction based on the joint kinematics data, joint loading data, and joint articulation behaviour data.

Preferably, the virtual prediction comprises a computer model prediction.

Advantageously, the virtual prediction of the joint kinematics data, joint loading data, and joint articulation behaviour data is provided as a computer model prediction to predict the alignment configuration of the orthopaedic implant for fitting the orthopaedic implant to the patient's joint.

Preferably, the patient specific information data is indicative of one or more static characteristics.

Advantageously, the alignment configuration of the orthopaedic implant can be accurately modelled for fitting the orthopaedic implant to the patient's joint by virtue of the patient specific information data associated with the patient's joint which takes into consideration one or more static characteristics of the patient's joint.

Preferably, the one or more static characteristics comprises one or more load bearing axes of a biomechanical reference frame.

Advantageously, the alignment configuration of the orthopaedic implant can be accurately modelled for fitting the orthopaedic implant to the patient's joint by virtue of the patient specific information data associated with the patient's joint which takes into consideration one or more load bearing axes of a biomechanical reference frame of the patient's joint.

Preferably, the one or more load bearing axes of the biomechanical reference frame comprises a primary load bearing axis.

Advantageously, the alignment configuration of the orthopaedic implant can be accurately modelled for fitting the orthopaedic implant to the patient's joint by virtue of the patient specific information data associated with the patient's joint which takes into consideration the primary load bearing axis of the patient's joint.

Preferably, the one or more static characteristics comprise one or more load bearing axes of at least one reference frame of the group of biomechanical reference frames comprising: an acetabular reference frame, a femoral reference frame, a tibial reference frame, and a spinal reference frame.

Preferably, the patient specific information data comprises 2D imaging data.

Advantageously, the alignment configuration of the orthopaedic implant can be accurately modelled for fitting the orthopaedic implant to the patient's joint by virtue of the patient specific information data associated with the patient's joint which takes into consideration 2D imaging data of the patient's joint.

Preferably, the 2D imaging data comprises one or more of: X-Ray data and visual fluoroscopy data.

Preferably, the patient specific information data comprises 3D imaging data.

Advantageously, the alignment configuration of the orthopaedic implant can be accurately modelled for fitting the orthopaedic implant to the patient's joint by virtue of the patient specific information data associated with the patient's joint which takes into consideration 3D imaging data of the patient's joint.

Preferably, the 3D imaging data comprises one or more of: Magnetic Resonance Imaging (MRI) data, Computed Tomography (CT) data, ultrasound data, radiological data, and motion capture data.

Preferably, the patient specific information data comprises 4D imaging data.

Advantageously, the alignment configuration of the orthopaedic implant can be accurately modelled for fitting the orthopaedic implant to the patient's joint by virtue of the patient specific information data associated with the patient's joint which takes into consideration 4D imaging data of the patient's joint.

Preferably, the 4D imaging data comprises motion capture data.

Preferably, the patient specific information data comprises 2D and 3D imaging data.

Advantageously, the alignment configuration of the orthopaedic implant can be accurately modelled for fitting the orthopaedic implant to the patient's joint by virtue of the patient specific information data associated with the patient's joint which takes into consideration both 2D and 3D imaging data of the patient's joint.

Preferably, the patient specific information data comprises data being indicative of one or more physical characteristics of the patient.

Advantageously, the alignment configuration of the orthopaedic implant can be accurately modelled for fitting the orthopaedic implant to the patient's joint by virtue of the patient specific information data associated with the patient's joint which takes into consideration one or more physical characteristics of the patient.

Preferably, the one or more physical characteristics comprises one or more of: age data, gender data, height data, weight data, activity level data, BMI data, body condition data, and body shape data.

Preferably, the computer-implemented method further comprises the steps of:
determining a set of possible alignment configurations according to the patient data and patient acquired data, the patient acquired data being indicative of one or more desired post-implant activities, the patient acquired data comprising post-implant activities preference data; and
selecting an alignment configuration from the set of possible alignment configurations according to the post-implant activities preference data.

Advantageously, the alignment configuration of the orthopaedic implant can be selected for fitting the orthopaedic implant to the patient's joint by virtue of the patient specific information data associated with the patient's joint which takes into consideration the patient's preference for performing one or more desired post-implant activities.

Preferably, the post-implant activities preference data is a preference ratio being indicative of comparative patient preference for the one or more desired post-implant activities.

Advantageously, the alignment configuration of the orthopaedic implant can be selected for fitting the orthopaedic implant to the patient's joint by virtue of the patient specific information associated with the patient's joint which takes into consideration comparative patient preference for performing the one or more desired post-implant activities.

Preferably, the computer-implemented method further comprises the step of:
accessing a database of library alignment configuration data, wherein the alignment configuration is further selected according to the library alignment configuration data.

Advantageously, the alignment configuration of the orthopaedic implant can be selected for fitting the orthopaedic implant to the patient's joint by virtue of the patient specific information data associated with the patient's joint which takes into consideration library alignment configurations suitable for performing the one or more desired post-implant activities.

Preferably, the library alignment configuration data comprises data relating to a group of available orthopaedic implants for performing at least one of the one or more desired post-implant activities.

Advantageously, the alignment configuration of the orthopaedic implant can be selected for fitting the orthopaedic implant to the patient's joint by virtue of the patient specific information data associated with the patient's joint which takes into consideration library alignment configurations that relate to a group of available orthopaedic implants having been previously selected by other patients for performing at least one of the one or more desired post-implant activities.

Preferably, the library alignment configuration data comprises data relating to a group of patients fitted with an orthopaedic implant for performing at least one of the one or more desired post-implant activities.

Advantageously, the alignment configuration of the orthopaedic implant can be selected for fitting the orthopaedic implant to the patient's joint by virtue of the patient specific information data associated with the patient's joint which takes into consideration library alignment configurations that relate to a group of patients having previously been fitted with an orthopaedic implant suitable for performing at least one of the one or more desired post-implant activities.

According to another aspect of the present invention, there is provided a computing device for modelling the alignment of an orthopaedic implant for a joint of a patient, the computing device comprising:
a processor for processing digital data;
a memory device for storing digital data including computer program code and being coupled to the processor via a bus; and
a data interface for sending and receiving digital data and being coupled to the processor via the bus, wherein the processor is controlled by the computer program code to:
receive, via the data interface, patient specific information data for deriving patient data, the patient specific information data being indicative of one or more dynamic characteristics;
calculate patient data according to the patient specific information data; and
calculate 3D model data of the joint according to the patient data, such that the 3D model data shows the orthopaedic implant in an alignment configuration.

Preferably, the one or more dynamic characteristics comprise a virtual prediction based on one or more of: joint kinematics data; joint loading data; and joint articulation behaviour data during desired post-implant activities.

Preferably, the virtual prediction comprises a computer model prediction.

Preferably, the patient specific information data is indicative of one or more static characteristics.

Preferably, the one or more static characteristics comprises one or more load bearing axes of a biomechanical reference frame.

Preferably, the one or more load bearing axes of the biomechanical reference frame comprises a primary load bearing axis.

Preferably, the one or more static characteristics comprise one or more load bearing axes of at least one reference frame of the group of biomechanical reference frames comprising: an acetabular reference frame, a femoral reference frame, a tibial reference frame, and a spinal reference frame.

Preferably, the patient specific information data comprises 2D imaging data.

Preferably, the 2D imaging data comprises one or more of: X-Ray data and visual fluoroscopy data.

Preferably, the patient specific information data comprises 3D imaging data.

Preferably, the 3D imaging data comprises one or more of: Magnetic Resonance Imaging (MRI) data, Computed Tomography (CT) data, ultrasound data, radiological data, and motion capture data.

Preferably, the patient specific information data comprises 4D imaging data.

Preferably, the 4D imaging data comprises motion capture data.

Preferably, the patient specific information data comprises 2D and 3D imaging data.

Preferably, the patient specific information data comprises data being indicative of one or more physical characteristics of the patient.

Preferably, the one or more physical characteristics comprises one or more of: age data, gender data, height data, weight data, activity level data, BMI data, body condition data, and body shape data.

Preferably, the processor is further controlled by the computer program code to:
  receive, via the data interface, patient acquired data being indicative of one or more desired post-implant activities, the patient acquired data comprising post-implant activities preference data;
  calculate a set of possible alignment configurations according to the patient data and the patient acquired data; and
  select an alignment configuration from the set of possible alignment configurations according to the post-implant activities preference data.

Preferably, the post-implant activities preference data is a preference ratio being indicative of comparative patient preference for the one or more desired post-implant activities.

Preferably, the computing device further comprises a database for storing digital data including library alignment configuration data, the database being coupled to the processor, wherein the processor is further controlled by the computer program code to:
  load, from the database, the library alignment configuration data, wherein the alignment configuration is further selected according to the library alignment configuration data.

Preferably, the library alignment configuration data comprises data relating to a group of available orthopaedic implants for performing at least one of the one or more desired post-implant activities.

Preferably, the library alignment configuration data comprises data relating to a group of patients fitted with an orthopaedic implant for performing at least one of the one or more desired post-implant activities.

According to another aspect of the present invention, there is provided a computer readable storage medium comprising computer program code instructions, being executable by a computer, for:
  receiving, via a data interface, patient specific information data for deriving patient data, the patient specific information being indicative of one or more dynamic characteristics;
  calculating patient data according to the patient specific information data; and
  calculating 3D model data of a joint according to the patient data, such that the 3D model data shows an orthopaedic implant in an alignment configuration.

Preferably, the one or more dynamic characteristics comprise a virtual prediction based on one or more of: joint kinematics data; joint loading data; and joint articulation behaviour data during desired post-implant activities.

Preferably, the virtual prediction comprises a computer model prediction.

Preferably, the patient specific information data is indicative of one or more static characteristics.

Preferably, the one or more static characteristics comprises one or more load bearing axes of a biomechanical reference frame.

Preferably, the one or more load bearing axes of the biomechanical reference frame comprises a primary load bearing axis.

Preferably, the one or more static characteristics comprise one or more load bearing axes of at least one reference frame of the group of biomechanical reference frames comprising: an acetabular reference frame, a femoral reference frame, a tibial reference frame, and a spinal reference frame.

Preferably, the patient specific information data comprises 2D imaging data.

Preferably, the 2D imaging data comprises one or more of: X-Ray data and visual fluoroscopy data.

Preferably, the patient specific information data comprises 3D imaging data.

Preferably, the 3D imaging data comprises one or more of: Magnetic Resonance Imaging (MRI) data, Computed Tomography (CT) data, ultrasound data, radiological data, and motion capture data.

Preferably, the patient specific information data comprises 4D imaging data.

Preferably, the 4D imaging data comprises motion capture data.

Preferably, the patient specific information data comprises 2D and 3D imaging data.

Preferably, the patient specific information data comprises data indicative of one or more physical characteristics of the patient.

Preferably, the one or more physical characteristics comprises one or more of: age data, gender data, height data, weight data, activity level data, BMI data, body condition data, and body shape data.

Preferably, the computer readable storage medium further comprises instructions for:
  receiving, via the data interface, patient acquired data being indicative of one or more desired post-implant activities, the patient acquired data comprising post-implant activities preference data;
  calculating a set of possible alignment configurations according to the patient data and the patient acquired data; and
  selecting an alignment configuration from the set of possible alignment configurations according to the post-implant activities preference data.

Preferably, the post-implant activities preference data is a preference ratio being indicative of comparative patient preference for the one or more desired post-implant activities.

Preferably, the computer readable storage medium further comprises instruction for:

loading from a database, library alignment configuration data, wherein the alignment configuration is further selected according to the library alignment configuration data.

Preferably, the library alignment configuration data comprises data relating to a group of available orthopaedic implants for performing at least one of the one or more desired post-implant activities.

Preferably, the library alignment configuration data comprises data relating to a group of patients fitted with an orthopaedic implant for performing at least one of the one or more desired post-implant activities.

According to another aspect of the present invention, there is provided a client computing device comprising an interface for sending and receiving digital data and being coupled, across a data link, to a computing device as defined in any one of the preceding paragraphs, wherein the interface is adapted for sending and receiving digital data as referred to in any one of the preceding paragraphs.

According to another aspect of the present invention, there is provided a computer-implemented method for selecting an orthopaedic implant for a joint of a patient from a group of orthopaedic implants, the computer-implemented method comprising the steps of:

being responsive to patient specific information data for deriving patient data, the patient specific information data being indicative of one or more dynamic characteristics;

being responsive to the patient data for providing actual 3D model data;

being responsive to the patient data for providing preferred 3D model data of the joint; and using the actual 3D model data and the preferred 3D model data to select the orthopaedic implant from the group of orthopaedic implants.

Advantageously, the orthopaedic implant can be selected from the group of orthopaedic implants for fitting to the patient's joint by virtue of comparing the actual 3D model of the joint with a preferred 3D model based on the one or more dynamic characteristics.

Preferably, the computer-implemented method further comprises the steps of:

receiving patient acquired data, the patient acquired data being indicative of one or more desired post-implant activities, the patient acquired data comprising post-implant activities preference data; and being responsive to the post-implant activities preference data for further optimizing the preferred 3D model data of the joint.

Advantageously, the orthopaedic implant can be selected from the group of orthopaedic implants for fitting to the patient's joint by virtue of comparing the actual 3D model of the joint with a preferred 3D model which takes into consideration post-implant activities preference data.

Preferably, the post-implant activities preference data is a preference ratio being indicative of comparative patient preference for the one or more desired post-implant activities.

Advantageously, the orthopaedic implant can be selected from the group of orthopaedic implants for fitting to the patient's joint by virtue of comparing the actual 3D model of the joint with a preferred 3D model which takes into consideration comparative patient preference for performing the one or more desired post-implant activities.

Preferably, the computer-implemented method further comprises the step of:

accessing a database of library alignment configuration data, wherein the preferred 3D model data of the joint is further provided based on an optimization of the actual 3D model data according to the library alignment configuration data.

Advantageously, the orthopaedic implant can be selected from the group of orthopaedic implants for fitting to the patient's joint by virtue of comparing the actual 3D model of the joint with a preferred 3D model which takes into consideration library alignment configuration data.

Preferably, the library alignment configuration data comprises data relating to a group of available orthopaedic implants for performing at least one of the one or more desired post-implant activities.

Advantageously, the orthopaedic implant can be selected from the group of orthopaedic implants for fitting to the patient's joint by virtue of comparing the actual 3D model of the joint with a preferred 3D model which takes into consideration library alignment configuration data that relates to a group of available orthopaedic implants having been previously selected by other patients for performing at least one of the one or more desired post-implant activities.

Preferably, the library alignment configuration data comprises data relating to a group of patients fitted with an orthopaedic implant for performing at least one of the one or more desired post-implant activities.

Advantageously, the orthopaedic implant can be selected from the group of orthopaedic implants for fitting to the patient's joint by virtue of comparing the actual 3D model of the joint with a preferred 3D model which takes into consideration library alignment configuration data that relates to a group of patients having previously been fitted with an orthopaedic implant suitable for performing at least one of the one or more desired post-implant activities.

Preferably, the computer-implemented method further comprises the step of:

displaying a graphical user interface comprising at least the preferred 3D model data of the joint.

Advantageously, the orthopaedic implant can be selected from the group of orthopaedic implants for fitting to the patient's joint by virtue of visually comparing the actual 3D model of the joint with a preferred 3D model displayed on the graphical user interface.

According to another aspect of the present invention, there is provided a computing device for selecting an orthopaedic implant for a joint of a patient from a group of orthopaedic implants, the computing device comprising:

a processor for processing digital data;

a memory device for storing digital data including computer program code and being coupled to the processor via a bus; and a data interface for sending and receiving digital data and being coupled to the processor via the bus, wherein the processor is controlled by the computer program code to:

receive, via the data interface, patient specific information data for deriving patient data, the patient specific information data being indicative of one or more dynamic characteristics;

calculate actual 3D model data of the joint according to the patient data;

calculate preferred 3D model data of the joint according to the patient data; and select the orthopaedic implant from the group of orthopaedic implants according to the actual 3D model data and the preferred 3D model data.

Preferably, the processor is further controlled by the computer program code to:
receive, via the data interface, patient acquired data, the patient acquired data being indicative of one or more desired post-implant activities, the patient acquired data comprising post-implant activities preference data; and
calculate the preferred 3D model data of the joint according to the post-implant activities preference data.

Preferably, the post-implant activities preference data is a preference ratio being indicative of comparative patient preference for the one or more desired post-implant activities.

Preferably, the computing device further comprises a database for storing digital data including library alignment configuration data, the database being coupled to the processor, wherein the processor is further controlled by the computer program code to:
load from the database, the library alignment configuration data, wherein the preferred 3D model of the joint is further calculated based on an optimization of the actual 3D model data according to the library alignment configuration data.

Preferably, the library alignment configuration data comprises data relating to a group of available orthopaedic implants for performing one or more desired post-implant activities.

Preferably, the library alignment configuration data comprises data relating to a group of patients fitted with an orthopaedic implant for performing one or more desired post-implant activities.

Preferably, the computing device further comprises a display device coupled to the processor, wherein the display device is controlled by the computer program code to display a graphical user interface comprising at least the preferred 3D model data of the joint; the data interface being controlled by the computer program code to receive at least the preferred 3D model data of the joint.

According to another aspect of the present invention, there is provided a computer readable storage medium comprising computer program code instructions, being executable by a computer, for:
receiving, via a data interface, patient specific information data for deriving patient data, the patient specific information data being indicative of one or more dynamic characteristics;
calculating actual 3D model data of the joint according to the patient data;
calculating preferred 3D model data of the joint according to the patient data; and
selecting the orthopaedic implant from a group of implants according to the actual 3D model data and the preferred 3D model data.

Preferably, the computer readable storage medium further comprises instructions for
receiving, via the data interface, patient acquired data, the patient acquired data being indicative of one or more desired post-implant activities, the patient acquired data comprising post-implant activities preference data; and
calculating the preferred 3D model data of the joint according to the post-implant activities preference data.

Preferably, the post-implant activities preference data is a preference ratio being indicative of comparative patient preference for the one or more desired post-implant activities.

Preferably, the computer readable storage medium further comprises instruction for:
loading from a database, library alignment configuration data, wherein the preferred 3D model data of the joint is further calculated based on an optimization of the actual 3D model data according to the library alignment configuration data.

Preferably, the library alignment configuration data comprises data relating to a group of available orthopaedic implants for performing at least one of the one or more desired post-implant activities.

Preferably, the library alignment configuration data comprises data relating to a group of patients fitted with an orthopaedic implant for performing at least one of the one or more desired post-implant activities.

Preferably, the computer readable storage medium further comprises instruction for:
displaying a graphical user interface comprising at least the preferred 3D model data of the joint.

According to another aspect of the present invention, there is provided a client computing device comprising an interface for sending and receiving digital data and being coupled, across a data link, to a computing as defined in any one of the preceding paragraphs, wherein the interface is adapted for sending and receiving digital data as referred to in any one of the preceding paragraphs.

According to another aspect of the present invention, there is provided a computer-implemented method for developing manufacturing parameters for manufacturing an orthopaedic implant for a joint of a patient having an orthopaedic implant articulation surface, the computer-implemented method comprising the steps of:
being responsive to patient specific information data for deriving patient data, the patient specific information data being indicative of one or more dynamic characteristics;
being responsive to the patient data for calculating design data for the orthopaedic implant; and
developing the manufacturing parameters for manufacturing the orthopaedic implant according to the design data.

Advantageously, manufacturing parameters for manufacturing an orthopaedic implant having a desired articulation surface can be developed by virtue of taking into consideration patient specific information data indicative of one or more dynamic characteristics for calculating design data for the orthopaedic implant.

Preferably, the patient specific information data comprises 2D imaging data.

Advantageously, manufacturing parameters for manufacturing an orthopaedic implant having a desired articulation surface can be developed by virtue of taking into consideration 2D imaging data of the patient's joint.

Preferably, the 2D imaging data comprises one or more of: X-Ray data and visual fluoroscopy data.

Preferably, the patient specific information data comprises 3D imaging data.

Advantageously, manufacturing parameters for manufacturing an orthopaedic implant having a desired articulation surface can be developed by virtue of taking into consideration 3D imaging data of the patient's joint.

Preferably, the 3D imaging data comprises one or more of: Magnetic Resonance Imaging (MRI) data, Computed Tomography (CT) data, ultrasound data, radiological data, and motion capture data.

Preferably, the patient specific information data comprises 4D imaging data.

Advantageously, manufacturing parameters for manufacturing an orthopaedic implant having a desired articulation surface can be developed by virtue of taking into consideration 4D imaging data of the patient's joint.

Preferably, the 4D imaging data comprises motion capture data.

Preferably, the patient specific information data comprises 2D and 3D imaging data.

Advantageously, manufacturing parameters for manufacturing an orthopaedic implant having a desired articulation surface can be developed by virtue of taking into consideration both 2D and 3D imaging data of the patient's joint.

Preferably, the patient specific information data comprises patient acquired data indicative of one or more desired post-implant activities.

Advantageously, manufacturing parameters for manufacturing an orthopaedic implant having a desired articulation surface can be developed by virtue of taking into consideration one or more desired post-implant activities.

Preferably, the one or more dynamic characteristics comprise a virtual prediction based on one or more of: joint kinematics data; joint loading data; and joint articulation behaviour data during desired post-implant activities.

Advantageously, manufacturing parameters for manufacturing an orthopaedic implant having a desired articulation surface can be developed by virtue of taking into consideration a virtual prediction based on the joint kinematics data, joint loading data, and joint articulation behaviour data.

Preferably, the virtual prediction comprises a computer model prediction.

Advantageously, manufacturing parameters for manufacturing an orthopaedic implant having a desired articulation surface can be developed by virtue of taking into consideration the virtual prediction of the joint kinematics data, joint loading data, and joint articulation behaviour data provided as a computer model prediction.

Preferably, the patient specific information data is indicative of one or more static characteristics.

Advantageously, manufacturing parameters for manufacturing an orthopaedic implant having a desired articulation surface can be developed by virtue of taking into consideration one or more static characteristics of the patient's joint.

Preferably, the one or more static characteristics comprises one or more load bearing axes of a biomechanical reference frame.

Advantageously, manufacturing parameters for manufacturing an orthopaedic implant having a desired articulation surface can be developed by virtue of taking into consideration one or more load bearing axes of a biomechanical reference frame of the patient's joint.

Preferably, the one or more load bearing axes of the biomechanical reference frame comprises a primary load bearing axis.

Advantageously, manufacturing parameters for manufacturing an orthopaedic implant having a desired articulation surface can be developed by virtue of taking into consideration the primary load bearing axis of the patient's joint.

Preferably, the one or more static characteristics comprise one or more load bearing axes of at least one reference frame of the group of biomechanical reference frames comprising: an acetabular reference frame, a femoral reference frame, a tibial reference frame, and a spinal reference frame.

Preferably, the patient specific information data comprises data indicative of one or more physical characteristics of the patient.

Advantageously, manufacturing parameters for manufacturing an orthopaedic implant having a desired articulation surface can be developed by virtue of taking into consideration one or more physical characteristics of the patient.

Preferably, the one or more physical characteristics comprises one or more of: age data, gender data, height data, weight data, activity level data, BMI data, body condition data, and body shape data.

Preferably, the computer-implemented method further comprises the steps of:
receiving patient acquired data, the patient acquired data being indicative of one or more desired post-implant activities, the patient acquired data comprising post-implant activities preference data;
being responsive to the post-implant activities preference data for calculating post-implant design data for the orthopaedic implant; and
developing the manufacturing parameters for manufacturing the orthopaedic implant further according to the post-implant design data.

Advantageously, manufacturing parameters for manufacturing an orthopaedic implant having a desired articulation surface can be developed by virtue of taking into consideration the patient's preference for performing one or more desired post-implant activities.

Preferably, the post-implant activities preference data is a preference ratio being indicative of comparative patient preference for the one or more desired post-implant activities.

Advantageously, manufacturing parameters for manufacturing an orthopaedic implant having a desired articulation surface can be developed by virtue of taking into consideration comparative patient preference for performing the one or more desired post-implant activities.

Preferably, the computer-implemented method further comprises the step of:
accessing a database of library design data, wherein the manufacturing parameters for manufacturing the orthopaedic implant are further developed according to the library design data.

Advantageously, manufacturing parameters for manufacturing an orthopaedic implant having a desired articulation surface can be developed by virtue of taking into consideration library design data suitable for performing the one or more desired post-implant activities.

Preferably, the library design data comprises data relating to a group of available orthopaedic implants for performing at least one of the one or more desired post-implant activities.

Advantageously, manufacturing parameters for manufacturing an orthopaedic implant having a desired articulation surface can be developed by virtue of taking into consideration library design data that relates to a group of available orthopaedic implants having been previously selected by other patients for performing at least one of the one or more desired post-implant activities.

Preferably, the library design data comprises data relating to a group of patients fitted with an orthopaedic implant for performing at least one of the one or more desired post-implant activities.

Advantageously, manufacturing parameters for manufacturing an orthopaedic implant having a desired articulation surface can be developed by virtue of taking into consideration library design data that relates to a group of patients having previously been fitted with an orthopaedic implant suitable for performing at least one of the one or more desired post-implant activities.

According to another aspect of the present invention, there is provided a method for manufacturing an orthopaedic implant for a joint of a patient having an orthopaedic implant articulation surface, the method comprising the steps of:

developing manufacturing parameters using the computer-implemented method as defined in any one of the preceding paragraphs; and manufacturing the orthopaedic implant according to the manufacturing parameters.

Advantageously, an orthopaedic implant having a desired articulation surface can be manufactured by virtue of taking into consideration the manufacturing parameters developed above.

Preferably, the orthopaedic implant is manufactured using a manufacturing process, comprising one or both of: an additive manufacturing process, and a subtractive manufacturing process.

Advantageously, the orthopaedic implant having a desired articulation surface can be manufactured according to either an additive or subtractive manufacturing process.

Preferably, the additive manufacturing process comprises one or more of: stereolithography (SLA), selective laser sintering (SLS), direct metal laser sintering (DMLS), electron beam melting (EBM), and 3D printing (3DP).

Preferably, the subtractive manufacturing process comprises one or more of: biomachining, abrasive flow machining, abrasive jet machining, milling, laser cutting, and water jet cutting.

According to another aspect of the present invention, there is provided an orthopaedic implant for a joint of a patient having an orthopaedic implant articulation surface manufactured using the method as defined in any one of the preceding paragraphs.

According to another aspect of the present invention, there is provided a computing device for developing manufacturing parameters for manufacturing an orthopaedic implant for a joint of a patient having an orthopaedic implant articulation surface, the computing device comprising:
- a processor for processing digital data;
- a memory device for storing digital data including computer program code and being coupled to the processor via a bus; and
- a data interface for sending and receiving digital data and being coupled to the processor via the bus, wherein the processor is controlled by the computer program code to:
  - receive, via the data interface, patient specific information data for deriving patient data, the patient specific information being indicative of one or more dynamic characteristics;
  - calculate patient data according to the patient specific information data;
  - calculate design data for the orthopaedic implant according to the patient data; and
  - calculate the manufacturing parameters for manufacturing the orthopaedic implant according to the design data.

Preferably, the patient specific information data comprises 2D imaging data.

Preferably, the 2D imaging data comprises one or more of: X-Ray data and visual fluoroscopy data.

Preferably, the patient specific information data comprises 3D imaging data.

Preferably, the 3D imaging data comprises one or more of: Magnetic Resonance Imaging (MRI) data, Computed Tomography (CT) data, ultrasound data, radiological data, and motion capture data.

Preferably, the patient specific information data comprises 4D imaging data.

Preferably, the 4D imaging data comprises motion capture data.

Preferably, the patient specific information data comprises 2D and 3D imaging data.

Preferably, the patient specific information data comprises patient acquired data indicative of one or more desired post-implant activities.

Preferably, the one or more dynamic characteristics comprises a virtual prediction based on one or more of: joint kinematics data; joint loading data; and joint articulation behaviour data during desired post-implant activities.

Preferably, the virtual prediction comprises a computer model prediction.

Preferably, the patient specific information data is indicative of one or more static characteristics.

Preferably, the one or more static characteristics comprise one or more load bearing axes of a biomechanical reference frame.

Preferably, the one or more load bearing axes of the biomechanical reference frame comprises a primary load bearing axis.

Preferably, the one or more static characteristics comprise one or more load bearing axes of at least one reference frame of the group of biomechanical reference frames comprising: an acetabular reference frame, a femoral reference frame, a tibial reference frame, and a spinal reference frame.

Preferably, the patient specific information data comprises data indicative of one or more physical characteristics of the patient.

Preferably, the one or more physical characteristics comprises one or more of: age data, gender data, height data, weight data, activity level data, BMI data, body condition data, and body shape data.

Preferably, the processor is further controlled by the computer program code to:
- receive, via the data interface, patient acquired data being indicative of one or more desired post-implant activities, the patient acquired data comprising post-implant activities preference data;
- calculate post-implant design data for the orthopaedic implant according to the post-implant activities preference data; and
- calculate the manufacturing parameters for manufacturing the orthopaedic implant further according to the post-implant design data.

Preferably, the post-implant activities preference data is a preference ratio being indicative of comparative patient preference for the one or more desired post-implant activities.

Preferably, the computing device further comprises a database for storing digital data including library design data, the database being coupled to the processor, wherein the processor is further controlled by the computer program code to:
- load from the database, the library design data, wherein the manufacturing parameters for manufacturing the orthopaedic implant are further calculated according to the library design data.

Preferably, the library design data comprises data relating to a group of available orthopaedic implants for performing at least one of the one or more desired post-implant activities.

Preferably, the library design data comprises data relating to a group of patients fitted with an orthopaedic implant for performing at least one of the one or more desired post-implant activities.

According to another aspect of the present invention, there is provided a computer readable storage medium comprising computer program code instructions, being executable by a computer, for:

receiving, via a data interface, patient specific information data for deriving patient data, the patient specific information being indicative of one or more dynamic characteristics;
  calculating patient data according to the patient specific information data;
  calculating design data for an orthopaedic implant according to the patient data; and
  calculating manufacturing parameters for manufacturing the orthopaedic implant according to the design data.

Preferably, the patient specific information data comprises 2D imaging data.

Preferably, the 2D imaging data comprises one or more of: X-Ray data and visual fluoroscopy data.

Preferably, the patient specific information data comprises 3D imaging data.

Preferably, the 3D imaging data comprises one or more of: Magnetic Resonance Imaging (MRI) data, Computed Tomography (CT) data, ultrasound data, radiological data, and motion capture data.

Preferably, the patient specific information data comprises 4D imaging data.

Preferably, the 4D imaging data comprises motion capture data.

Preferably, the patient specific information data comprises 2D and 3D imaging data.

Preferably, the patient specific information data comprises patient acquired data indicative of one or more desired post-implant activities.

Preferably, the one or more dynamic characteristics comprises a virtual prediction based on one or more of: joint kinematics data; joint loading data; and joint articulation behaviour data during desired post-implant activities.

Preferably, the virtual prediction comprises a computer model prediction.

Preferably, the patient specific information data is indicative of one or more static characteristics.

Preferably, the one or more static characteristics comprise one or more load bearing axes of a biomechanical reference frame.

Preferably, the one or more load bearing axes of the biomechanical reference frame comprises a primary load bearing axis.

Preferably, the one or more static characteristics comprise one or more load bearing axes of at least one reference frame of the group of biomechanical reference frames comprising: an acetabular reference frame, a femoral reference frame, a tibial reference frame, and a spinal reference frame.

Preferably, the patient specific information data comprises data indicative of one or more physical characteristics of the patient.

Preferably, the one or more physical characteristics comprises one or more of: age data, gender data, height data, weight data, activity level data, BMI data, body condition data, and body shape data.

Preferably, the computer readable storage medium further comprises instructions for:
  receiving, via the data interface, patient acquired data being indicative of one or more desired post-implant activities, the patient acquired data comprising post-implant activities preference data;
  calculating post-implant design data according to the post-implant activities preference data; and
  calculating manufacturing parameters for manufacturing the orthopaedic implant according to the post-implant design data.

Preferably, the post-implant activities preference data is a preference ratio being indicative of comparative patient preference for the one or more desired post-implant activities.

Preferably, the computer readable storage medium further comprises instruction for:
  loading from a database, library design data, wherein the manufacturing parameters for manufacturing the orthopaedic implant are further calculated according to the library design data.

Preferably, the library design data comprises data relating to a group of available orthopaedic implants for performing at least one of the one or more desired post-implant activities.

Preferably, the library design data comprises data relating to a group of patients fitted with an orthopaedic implant for performing at least one of the one or more desired post-implant activities.

According to another aspect of the present invention, there is provided a computer-implemented method for developing manufacturing parameters for manufacturing a custom articulation for attachment to an orthopaedic implant, the computer-implemented method comprising the steps of:
  receiving design data according to the computer-implemented method as defined in any one of the preceding paragraphs; and
  developing the manufacturing parameters for manufacturing the custom articulation according to the design data.

Advantageously, manufacturing parameters for manufacturing a custom articulation for attachment to an orthopaedic implant can be developed by virtue of taking into consideration the design data calculated for developing the manufacturing parameters for the orthopaedic implant.

Preferably, the computer-implemented method further comprises the steps of:
  receiving post-implant design data according to the computer-implemented method as defined in any one of the preceding paragraphs; and
  developing the manufacturing parameters for manufacturing the custom implant further according to the post-implant design data.

Advantageously, manufacturing parameters for manufacturing a custom articulation for attachment to an orthopaedic implant can be further developed by virtue of taking into consideration the post-implant design data corresponding to the patient's preference for performing one or more desired post-implant activities.

Preferably, the computer-implemented method further comprises the step of:
  accessing a database of library design data, wherein the manufacturing parameters for manufacturing the custom implant are further developed according to the library design data.

Advantageously, manufacturing parameters for manufacturing a custom articulation for attachment to an orthopaedic implant can be developed further by virtue of taking into consideration the library design data suitable for performing the one or more desired post-implant activities.

Preferably, the library design data comprises data relating to a group of available orthopaedic implants for performing at least one of the one or more desired post-implant activities.

Advantageously, manufacturing parameters for manufacturing a custom articulation for attachment to an orthopaedic implant can be developed further by virtue of taking into consideration the library design data that relates to a group of available orthopaedic implants having been previously selected by other patients for performing at least one of the one or more desired post-implant activities.

Preferably, the library design data comprises data relating to a group of patients fitted with an orthopaedic implant for performing at least one of the one or more desired post-implant activities.

Advantageously, manufacturing parameters for manufacturing a custom articulation for attachment to an orthopaedic implant can be developed further by virtue of taking into consideration the library design data that relates to a group of patients having previously been fitted with an orthopaedic implant suitable for performing at least one of the one or more desired post-implant activities.

According to another aspect of the present invention, there is provided a method for manufacturing a custom articulation for attachment to an orthopaedic implant, the method comprising the steps of:

developing manufacturing parameters using the computer-implemented method as defined in any one of the preceding paragraphs; and manufacturing the custom articulation according to the manufacturing parameters.

Advantageously, a custom articulation can be manufactured by virtue of taking into consideration the manufacturing parameters developed above.

Preferably, the custom articulation is manufactured using a manufacturing process, comprising one or both of: an additive manufacturing process, and a subtractive manufacturing process.

Advantageously, a custom articulation can be manufactured according to either an additive or subtractive manufacturing process.

Preferably, the additive manufacturing process comprises one or more of: stereolithography (SLA), selective laser sintering (SLS), direct metal laser sintering (DMLS), electron beam melting (EBM), and 3D printing (3DP).

Preferably, the subtractive manufacturing process comprises one or more of: biomachining, abrasive flow machining, abrasive jet machining, milling, laser cutting, and water jet cutting.

According to another aspect of the present invention, there is provided a custom articulation for attachment to an orthopaedic implant manufactured using the method as defined in any one of the preceding paragraphs.

According to another aspect of the present invention, there is provided a computing device for developing manufacturing parameters for manufacturing a custom articulation for attachment to an orthopaedic implant, the computing device comprising:

a processor for processing digital data;

a memory device for storing digital data including computer program code and being coupled to the processor via a bus; and a data interface for sending and receiving digital data and being coupled to the processor via the bus, wherein the processor is controlled by the computer program code to:

receive, via the data interface, design data according to the computer-implemented method as defined in any one of the preceding paragraphs; and calculate the manufacturing parameters for manufacturing the custom articulation according to the design data.

Preferably, the processor is further controlled by the computer program code to:

receive, via the data interface, post-implant design data according to the computer-implemented method as defined in any one of the preceding paragraphs; and calculate the manufacturing parameters for manufacturing the custom articulation further according to the post-implant design data.

Preferably, the computing device further comprises a database for storing digital data including library design data, the database being coupled to the processor, wherein the processor is further controlled by the computer program code to:

load from the database, the library design data, wherein the manufacturing parameters for manufacturing the custom articulation are further calculated according to the library design data.

Preferably, the library design data comprises data relating to a group of available orthopaedic implants for performing at least one of the one or more desired post-implant activities.

Preferably, the library design data comprises data relating to a group of patients fitted with an orthopaedic implant for performing at least one of the one or more desired post-implant activities.

According to another aspect of the present invention, there is provided a computer readable storage medium comprising computer program code instructions, being executable by a computer, for:

receiving, via a data interface, design data as defined according to the computer-implemented method as defined in any one of the preceding paragraphs; and calculating manufacturing parameters for manufacturing a custom articulation according to the design data.

Preferably, the computer readable storage medium further comprises instructions for:

receiving, via the data interface, post-implant design data according to the computer-implemented method as defined in any one of the preceding paragraphs; and calculating the manufacturing parameters for manufacturing the custom articulation according to the post-implant design data.

Preferably, the computer readable storage medium further comprises instruction for:

loading from a database, library design data, wherein the manufacturing parameters for manufacturing the custom articulation are further calculated according to the library design data.

Preferably, the library design data comprises data relating to a group of available orthopaedic implants for performing at least one of the one or more desired post-implant activities.

Preferably, the library design data comprises data relating to a group of patients fitted with an orthopaedic implant for performing at least one of the one or more desired post-implant activities.

According to another aspect of the present invention, there is provided a computer-implemented method for developing manufacturing parameters for manufacturing a patient specific jig for aligning an orthopaedic implant to a joint of a patient, the computer-implemented method comprising the steps of:

being responsive to patient specific information data for deriving patient data, the patient specific information data being indicative of one or more dynamic characteristics;

being responsive to the patient data for calculating jig design data for the patient specific jig; and developing the manufacturing parameters for manufacturing the patient specific jig according to the jig design data.

Advantageously, manufacturing parameters for manufacturing a patient specific jig can be developed by virtue of taking into consideration patient specific information data for calculating jig design data to enable the patient specific jig to be fitted to the joint of the patient.

Preferably, the patient specific information data comprises patient acquired data indicative of one or more desired post-implant activities.

Advantageously, manufacturing parameters for manufacturing a patient specific jig can be developed by virtue of taking into consideration one or more desired post-implant activities.

Preferably, the one or more dynamic characteristics comprise a virtual prediction based on one or more of: joint kinematics data; joint loading data; and joint articulation behaviour data during desired post-implant activities.

Advantageously, manufacturing parameters for manufacturing a patient specific jig can be developed by virtue of taking into consideration a virtual prediction based on the joint kinematics data, joint loading data, and joint articulation behaviour data.

Preferably, the virtual prediction comprises a computer model prediction.

Advantageously, manufacturing parameters for manufacturing a patient specific jig can be developed by virtue of taking into consideration the virtual prediction of the joint kinematics data, joint loading data, and joint articulation behaviour data provided as a computer model prediction.

Preferably, the patient specific information data is indicative of one or more static characteristics.

Advantageously, manufacturing parameters for manufacturing a patient specific jig can be developed by virtue of deriving patient specific information data that takes into consideration one or more static characteristics of the patient's joint.

Preferably, the one or more static characteristics comprises one or more load bearing axes of a biomechanical reference frame.

Advantageously, manufacturing parameters for manufacturing a patient specific jig can be developed by virtue of deriving patient specific information data that takes into consideration one or more load bearing axes of a biomechanical reference frame of the patient's joint.

Preferably, the one or more load bearing axes of the biomechanical reference frame comprises a primary load bearing axis.

Advantageously, manufacturing parameters for manufacturing a patient specific jig can be developed by virtue of deriving patient specific information data that takes into consideration the primary load bearing axis of the patient's joint.

Preferably, the one or more static characteristics comprise one or more load bearing axes of at least one reference frame of the group of biomechanical reference frames comprising: an acetabular reference frame, a femoral reference frame, a tibial reference frame, and a spinal reference frame.

Preferably, the patient specific information data comprises 2D imaging data.

Advantageously, manufacturing parameters for manufacturing a patient specific jig can be developed by virtue of deriving patient specific information data that takes into consideration 2D imaging data of the patient's joint.

Preferably, the 2D imaging data comprises one or more of: X-Ray data and visual fluoroscopy data.

Preferably, the patient specific information data comprises 3D imaging data.

Advantageously, manufacturing parameters for manufacturing a patient specific jig can be developed by virtue of deriving patient specific information data that takes into consideration 3D imaging data of the patient's joint.

Preferably, the 3D imaging data comprises one or more of: Magnetic Resonance Imaging (MRI) data, Computed Tomography (CT) data, ultrasound data, radiological data, and motion capture data.

Preferably, the patient specific information data comprises 4D imaging data.

Advantageously, manufacturing parameters for manufacturing a patient specific jig can be developed by virtue of deriving patient specific information data that takes into consideration 4D imaging data of the patient's joint.

Preferably, the 4D imaging data comprises motion capture data.

Preferably, the patient specific information data comprises 2D and 3D imaging data.

Advantageously, manufacturing parameters for manufacturing a patient specific jig can be developed by virtue of deriving patient specific information data that takes into consideration both 2D and 3D imaging data of the patient's joint.

Preferably, the patient specific information data comprises data indicative of one or more physical characteristics of the patient.

Advantageously, manufacturing parameters for manufacturing a patient specific jig can be developed by virtue of deriving patient specific information data that takes into consideration one or more physical characteristics of the patient.

Preferably, the one or more physical characteristics comprises one or more of: age data, gender data, height data, weight data, activity level data, BMI data, body condition data, and body shape data.

According to another aspect of the present invention, there is provided a method for manufacturing a patient specific jig for aligning an orthopaedic implant to a joint of a patient, the method comprising the steps of:

developing manufacturing parameters using the computer-implemented method as defined in any one of the preceding paragraphs; and manufacturing the patient specific jig according to the manufacturing parameters.

Preferably, the patient specific jig is manufactured using a manufacturing process, comprising one or both of: an additive manufacturing process, and a subtractive manufacturing process.

Preferably, the additive manufacturing process comprises one or more of: stereolithography (SLA), selective laser sintering (SLS), direct metal laser sintering (DMLS), electron beam melting (EBM), and 3D printing (3DP).

Preferably, the subtractive manufacturing process comprises one or more of: biomachining, abrasive flow machining, abrasive jet machining, milling, laser cutting, and water jet cutting.

According to another aspect of the present invention, there is provided a patient specific jig for aligning an orthopaedic implant to a joint of a patient manufactured using the method as defined in any one of the preceding paragraphs.

According to another aspect of the present invention, there is provided a computing device for developing manufacturing parameters for manufacturing a patient specific jig for aligning an orthopaedic implant to a joint of a patient, the computing device comprising:

a processor for processing digital data;

a memory device for storing digital data including computer program code and being coupled to the processor via a bus; and a data interface for sending and receiving digital data and being coupled to the processor via the bus, wherein the processor is controlled by the computer program code to:

receive, via the data interface, patient specific information data for deriving patient data, the patient specific information data being indicative of one or more dynamic characteristics;

calculate patient data according to the patient specific information data;

calculate jig design data for the patient specific jig according to the patient data; and calculate the manufacturing parameters for manufacturing the patient specific jig according to the jig design data.

Preferably, the patient specific information data comprises patient acquired data indicative of one or more desired post-implant activities.

Preferably, the one or more dynamic characteristics comprise a virtual prediction based on one or more of: joint kinematics data; joint loading data; and joint articulation behaviour data during desired post-implant activities.

Preferably, the virtual prediction comprises a computer model prediction.

Preferably, the patient specific information data is indicative of one or more static characteristics.

Preferably, the one or more static characteristics comprises one or more load bearing axes of a biomechanical reference frame.

Preferably, the one or more load bearing axes of the biomechanical reference frame comprises a primary load bearing axis.

Preferably, the one or more static characteristics comprise one or more load bearing axes of at least one reference frame of the group of biomechanical reference frames comprising: an acetabular reference frame, a femoral reference frame, a tibial reference frame, and a spinal reference frame.

Preferably, the patient specific information data comprises 2D imaging data.

Preferably, the 2D imaging data comprises one or more of: X-Ray data and visual fluoroscopy data Preferably, the patient specific information data comprises 3D imaging data.

Preferably, the 3D imaging data comprises one or more of: Magnetic Resonance Imaging (MRI) data, Computed Tomography (CT) data, ultrasound data, radiological data, and motion capture data.

Preferably, the patient specific information data comprises 4D imaging data.

Preferably, the 4D imaging data comprises motion capture data.

Preferably, the patient specific information data comprises 2D and 3D imaging data.

Preferably, the patient specific information data comprises data indicative of one or more physical characteristics of the patient.

Preferably, the one or more physical characteristics comprises one or more of: age data, gender data, height data, weight data, activity level data, BMI data, body condition data, and body shape data.

According to another aspect of the present invention, there is provided a computer readable storage medium comprising computer program code instructions, being executable by a computer, for:

receiving, via a data interface, patient specific information data for deriving patient data, the patient specific information data being indicative of one or more dynamic characteristics;

calculating patient data according to the patient specific information data;

calculating jig design data for a patient specific jig according to the patient data; and calculating manufacturing parameters for manufacturing the patient specific jig according to the jig design data.

Preferably, the patient specific information data comprises patient acquired data indicative of one or more desired post-implant activities.

Preferably, the one or more dynamic characteristics comprise a virtual prediction based on one or more of: joint kinematics data; joint loading data; and joint articulation behaviour data during desired post-implant activities.

Preferably, the virtual prediction comprises a computer model prediction.

Preferably, the patient specific information data is indicative of one or more static characteristics.

Preferably, the one or more static characteristics comprises one or more load bearing axes of a biomechanical reference frame.

Preferably, the one or more load bearing axes of the biomechanical reference frame comprises a primary load bearing axis.

Preferably, the one or more static characteristics comprise one or more load bearing axes of at least one reference frame of the group of biomechanical reference frames comprising: an acetabular reference frame, a femoral reference frame, a tibial reference frame, and a spinal reference frame.

Preferably, the patient specific information data comprises 2D imaging data.

Preferably, the 2D imaging data comprises one or more of: X-Ray data and visual fluoroscopy data.

Preferably, the patient specific information data comprises 3D imaging data.

Preferably, the 3D imaging data comprises one or more of: Magnetic Resonance Imaging (MRI) data, Computed Tomography (CT) data, ultrasound data, radiological data, and motion capture data.

Preferably, the patient specific information data comprises 4D imaging data.

Preferably, the 4D imaging data comprises motion capture data.

Preferably, the patient specific information data comprises 2D and 3D imaging data.

Preferably, the patient specific information data comprises data indicative of one or more physical characteristics of the patient.

Preferably, the one or more physical characteristics comprises one or more of: age data, gender data, height data, weight data, activity level data, BMI data, body condition data, and body shape data.

According to another aspect of the present invention, there is provided a computer-implemented method for calculating implant design data for a group of orthopaedic implants, the computer-implemented method comprising the steps of:

receiving patient library data;

receiving implant range data; and calculating the implant design data for the group of orthopaedic implants according to the patient library data and the implant range data.

Advantageously, implant design data can be calculated for a group of orthopaedic implants by virtue of taking into consideration patient library data and implant range data.

Preferably, the patient library data comprises alignment information data of multiple orthopaedic implants of multiple patients provided by the computer-implemented method as defined in any one of the preceding paragraphs.

Advantageously, implant design data can be calculated for a group of orthopaedic implants by virtue of taking into consideration alignment information data of multiple orthopaedic implants of multiple patients.

Preferably, the implant range data is indicative of one or more subsets of the patient library data selected according to a user input request.

Advantageously, implant design data can be calculated for a group of orthopaedic implants by virtue of selecting one or more subsets of the patient library data.

Preferably, at least one of the one or more subsets comprises patient satisfaction data relating to a number of satisfied patients selected from a group of patients fitted with an orthopaedic implant for performing one or more post-implant activities.

Preferably, at least one of the one or more subsets comprises implant activity data relating to a number of orthopaedic implants selected from a group of orthopaedic implants for performing one or more post-implant activities.

Preferably, at least one of the one or more subsets comprises implant size data relating to a number of orthopaedic implants of a particular size range selected from a group of orthopaedic implants for performing one or more post-implant activities.

Preferably, revised patient library data is calculated on the basis of filtering the patient library data according to the implant range data.

Advantageously, implant design data can be calculated for a group of orthopaedic implants by virtue of taking into consideration patient library data that has been filtered according to the implant range data.

Preferably, the implant design data is calculated according to a statistical analysis of the revised patient library data.

Advantageously, implant design data can be calculated for a group of orthopaedic implants by virtue of a statistical analysis of the patient library data revised according to the implant range data.

Preferably, the statistical analysis is selected from a group of statistical analyses comprising: regression analysis and least squares analysis.

According to another aspect of the present invention, there is provided a computing device for calculating implant design data for a group of orthopaedic implants, the computing device comprising:
 a processor for processing digital data;
 a memory device for storing digital data including computer program code and being coupled to the processor via a bus; and
 a data interface for sending and receiving digital data and being coupled to the processor via the bus, wherein the processor is controlled by the computer program code to:
  receive, via the data interface, patient library data;
  receive, via the data interface, implant range data; and
  calculate the implant design data for the group of orthopaedic implants according to the patient library data and the implant range data.

Preferably, the patient library data comprises alignment information data of multiple orthopaedic implants of multiple patients provided by the computer-implemented method as defined in any one of the preceding paragraphs.

Preferably, the implant range data is indicative of one or more subsets of the patient library data selected according to a user input request.

Preferably, at least one of the one or more subsets comprises patient satisfaction data relating to a number of satisfied patients selected from a group of patients fitted with an orthopaedic implant for performing one or more post-implant activities.

Preferably, at least one of the one or more subsets comprises implant activity data relating to a number of orthopaedic implants selected from a group of orthopaedic implants for performing one or more post-implant activities.

Preferably, at least one of the one or more subsets comprises implant size data relating to a number of orthopaedic implants of a particular size range selected from a group of orthopaedic implants for performing one or more post-implant activities.

Preferably, revised patient library data is calculated on the basis of filtering the patient library data according to the implant range data.

Preferably, the implant design data is calculated according to a statistical analysis of the revised patient library data.

Preferably, the statistical analysis is selected from a group of statistical analyses comprising: regression analysis and least squares analysis.

According to another aspect of the present invention, there is provided a computer readable storage medium comprising computer program code instructions, being executable by a computer, for:
 receiving, via a data interface, patient library data;
 receiving, via the data interface, implant range data; and
 calculating implant design data for a group of orthopaedic implants according to the patient library data and the implant range data.

Preferably, the patient library data comprises alignment information data of multiple orthopaedic implants of multiple patients provided by the computer-implemented method as defined in any one of the preceding paragraphs.

Preferably, the implant range data is indicative of one or more subsets of the patient library data selected according to a user input request.

Preferably, at least one of the one or more subsets comprises patient satisfaction data relating to a number of satisfied patients selected from a group of patients fitted with an orthopaedic implant for performing one or more post-implant activities.

Preferably, at least one of the one or more subsets comprises implant activity data relating to a number of orthopaedic implants selected from a group of orthopaedic implants for performing one or more post-implant activities.

Preferably, at least one of the one or more subsets comprises implant size data relating to a number of orthopaedic implants of a particular size range selected from a group of orthopaedic implants for performing one or more post-implant activities.

Preferably, revised patient library data is calculated on the basis of filtering the patient library data according to the implant range data Preferably, the implant design data is calculated according to a statistical analysis of the revised patient library data.

Preferably, the statistical analysis is selected from a group of statistical analyses comprising: regression analysis and least squares analysis.

According to another aspect of the present invention, there is provided a client computing device comprising an interface for sending and receiving digital data and being coupled, across a data link, to a computing device as defined in any one of the preceding paragraphs, wherein the interface is adapted for sending and receiving digital data as referred to in any one of the preceding paragraphs.

Other aspects of the invention are also disclosed.

BRIEF DESCRIPTION OF THE DRAWINGS

Notwithstanding any other forms which may fall within the scope of the present invention, preferred embodiments of the invention will now be described, by way of example only, with reference to the accompanying drawings in which:

FIGS. 20A and 20B show graphical representations of library alignment information data obtained for a group of eight patients, each fitted with an orthopaedic implant, for use in selecting alignment information data for the alignment of an orthopaedic implant for a joint of a patient in accordance with an embodiment of the present invention, shown for the change in internal-external rotation of the left and right knee joints, FIG. 20A, and the change in patella shear force, FIG. 20B, when moving from a generally standing to a generally crouching or squatting position;

DESCRIPTION OF EMBODIMENTS

Figure 1:
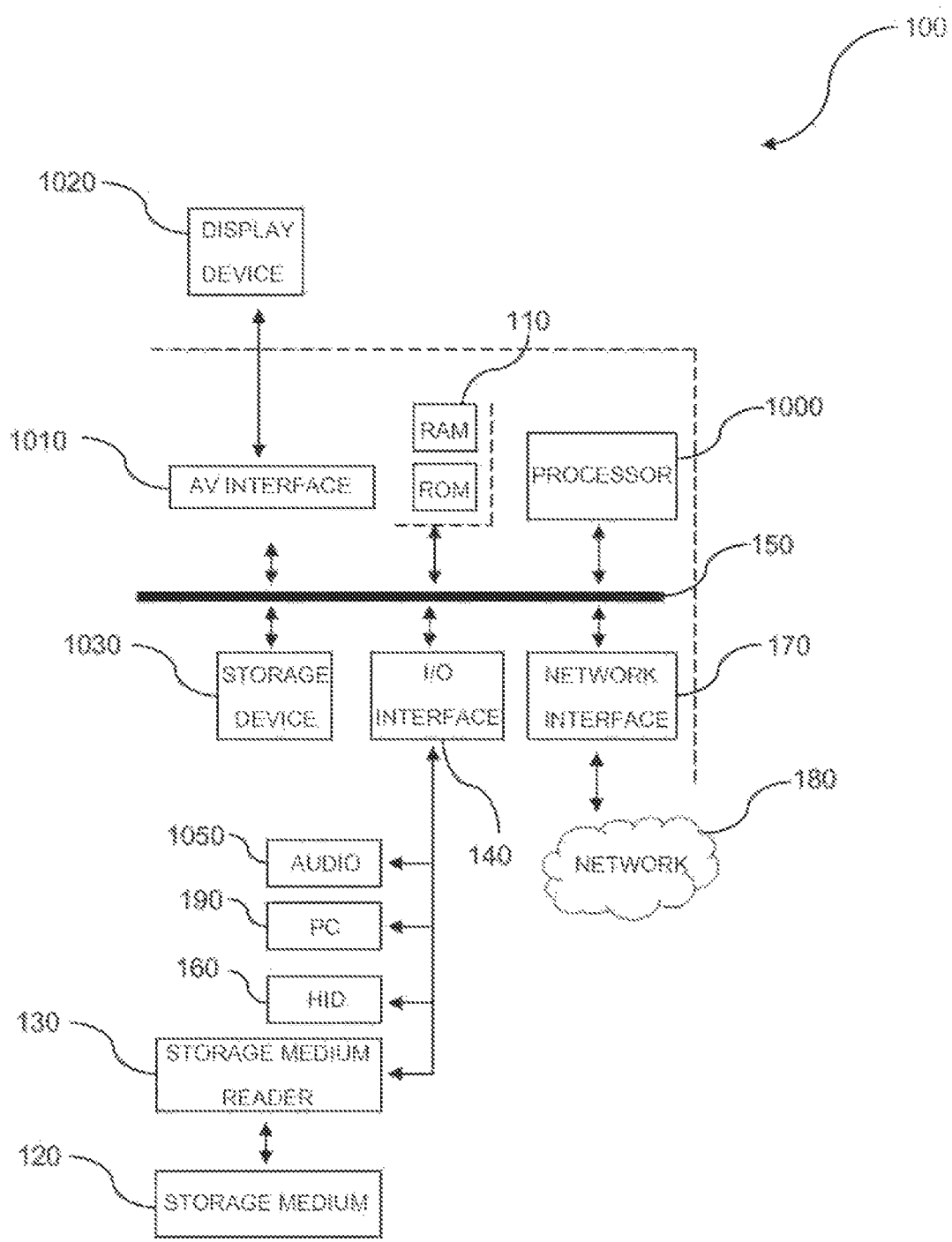
FIG. 1 shows a computing device on which the various embodiments described herein may be implemented in accordance with a preferred embodiment of the present invention.

It should be noted in the following description that like or the same reference numerals in different embodiments denote the same or similar features.

FIG. 1 shows a computing device 100 on which the various embodiments described herein may be implemented. The computer program code instructions may be divided into one or more computer program code instruction libraries, such as dynamic link libraries (DLL), wherein each of the libraries performs a one or more steps of the method. Additionally, a subset of the one or more of the libraries may perform graphical user interface tasks relating to the steps of the method.

The computing device 100 comprises semiconductor memory 110 comprising volatile memory such as random access memory (RAM) or read only memory (ROM). The memory 100 may comprise either RAM or ROM or a combination of RAM and ROM.

The computing device 100 comprises a computer program code storage medium reader 130 for reading the computer program code instructions from computer program code storage media 120. The storage media 120 may be optical media such as CD-ROM disks, magnetic media such as floppy disks and tape cassettes or flash media such as USB memory sticks.

The computing device 100 further comprises I/O interface 140 for communicating with one or more peripheral devices. The I/O interface 140 may offer both serial and parallel interface connectivity. For example, the I/O interface 140 may comprise a Small Computer System Interface (SCSI), Universal Serial Bus (USB) or similar I/O interface for interfacing with the storage medium reader 130. The I/O interface 140 may also communicate with one or more human input devices (HID) 160 such as keyboards, pointing devices, joysticks and the like. The I/O interface 140 may also comprise a computer to computer interface, such as a Recommended Standard 232 (RS-232) interface, for interfacing the device 100 with one or more personal computer (PC) devices 190. The I/O interface 140 may also comprise an audio interface for communicate audio signals to one or more audio devices 1050, such as a speaker or a buzzer.

The computing device 100 also comprises a network interface 170 for communicating with one or more computer networks 180. The network 180 may be a wired network, such as a wired Ethernet™ network or a wireless network, such as a Bluetooth™ network or IEEE 802.11 network. The network 180 may be a local area network (LAN), such as a home or office computer network, or a wide area network (WAN), such as the Internet 230 or private WAN.

The computing device 100 comprises an arithmetic logic unit or processor 1000 for performing the computer program code instructions. The processor 1000 may be a reduced instruction set computer (RISC) or complex instruction set computer (CISC) processor or the like. The computing device 100 further comprises a storage device 1030, such as a magnetic disk hard drive or a solid state disk drive.

Computer program code instructions may be loaded into the storage device 1030 from the storage media 120 using the storage medium reader 130 or from the network 180 using network interface 170. During the bootstrap phase, an operating system and one or more software applications are loaded from the storage device 1030 into the memory 110. During the fetch-decode-execute cycle, the processor 1000 fetches computer program code instructions from memory 110, decodes the instructions into machine code, executes the instructions and stores one or more intermediate results in memory 100.

The computing device 100 also comprises a video interface 1010 for conveying video signals to a display device 1020, such as a liquid crystal display (LCD), cathode-ray tube (CRT) or similar display device.

The computing device 100 also comprises a communication bus subsystem 150 for interconnecting the various devices described above. The bus subsystem 150 may offer parallel connectivity such as Industry Standard Architecture (ISA), conventional Peripheral Component Interconnect (PCI) and the like or serial connectivity such as PCI Express (PCIe), Serial Advanced Technology Attachment (Serial ATA) and the like.

Figure 2:
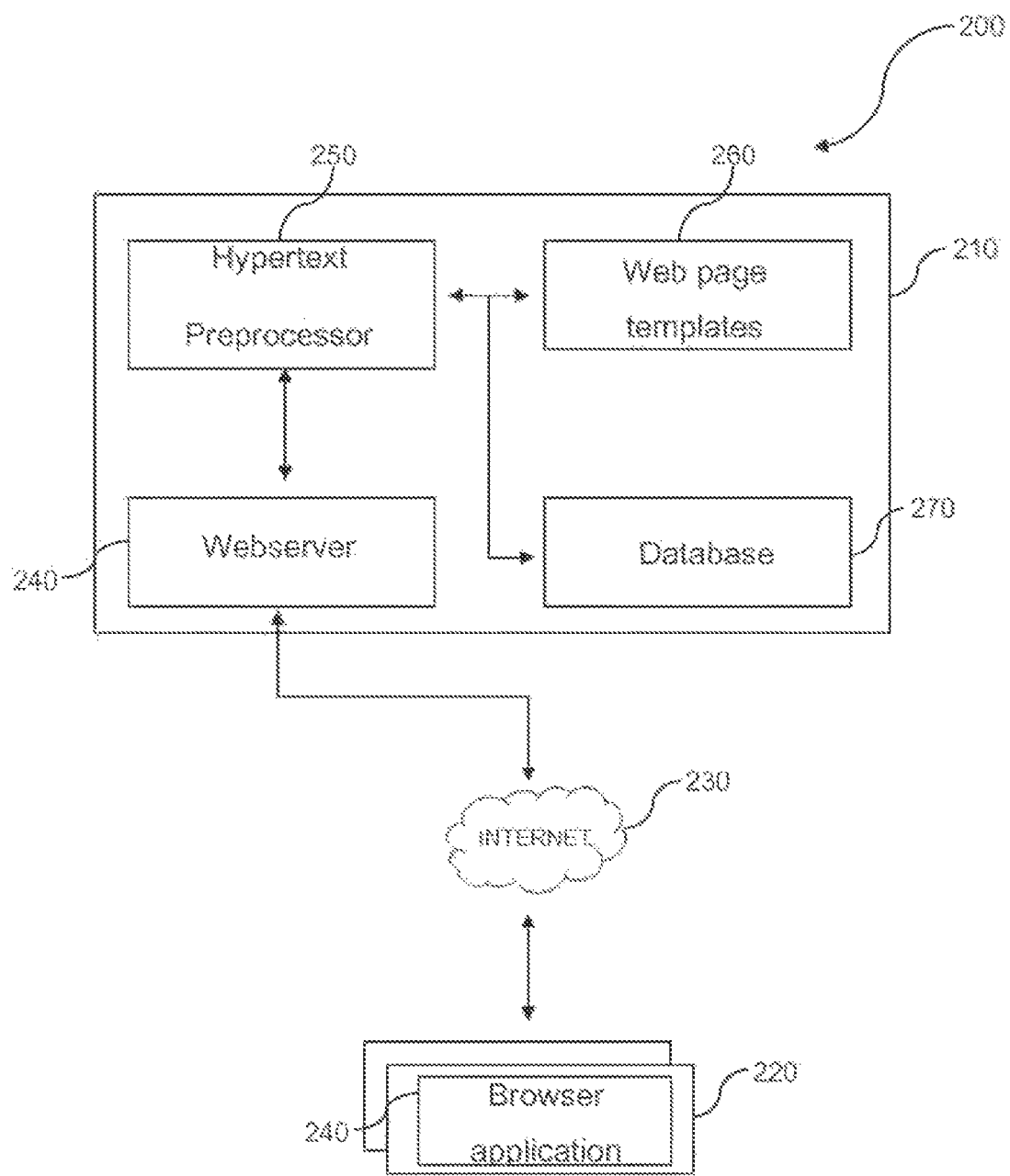
FIG. 2 shows a network of computing devices on which the various embodiments described herein may be implemented in accordance with a preferred embodiment of the present invention.

FIG. 2 shows a network 200 of computing devices 100 on which the various embodiments described herein may be implemented. The network 200 comprises a web server 210 for serving web pages to one or more client computing devices 220 over the Internet 230.

The web server 210 is provided with a web server application 240 for receiving requests, such as Hypertext Transfer Protocol (HTTP) and File Transfer Protocol (FTP) requests, and serving hypertext web pages or files in response. The web server application 240 may be, for example the Apache™ or the Microsoft™ IIS HTTP server.

The web server 210 is also provided with a hypertext preprocessor 250 for processing one or more web page templates 260 and data from one or more databases 270 to generate hypertext web pages. The hypertext preprocessor may, for example, be the PHP: Hypertext Preprocessor (PHP) or Microsoft Asp™ hypertext preprocessor. The web server 210 is also provided with web page templates 260, such as one or more PHP or ASP files.

Upon receiving a request from the web server application 240, the hypertext preprocessor 250 is operable to retrieve a web page template, from the web page templates 260, execute any dynamic content therein, including updating or loading information from the one or more databases 270, to compose a hypertext web page. The composed hypertext web page may comprise client side code, such as Javascript, for Document Object Model (DOM) manipulating, asynchronous HTTP requests and the like.

Client computing devices 220 are provided with a browser application 280, such as the Mozilla Firefox™ or Microsoft Internet Explorer™ browser applications. The browser application 280 requests hypertext web pages from the web server 210 and renders the hypertext web pages on a display device 1020.

The computing device 100 enables thin client communications with remote users. However, in other embodiments, remote users need to have specific software installed on the relevant client computing devices 220 to permit communication with the computing device 100.

Providing Alignment Information Data

Figure 3:
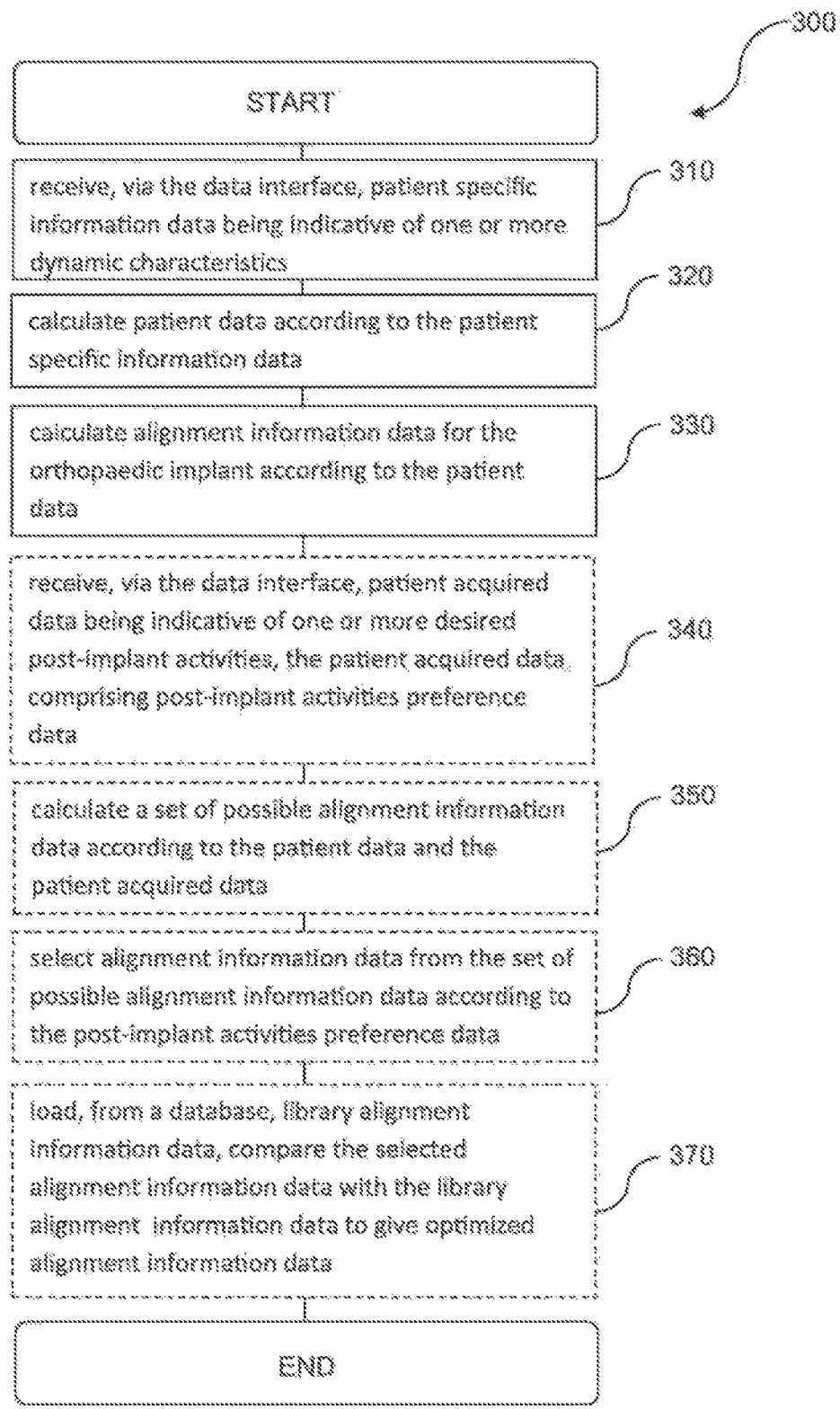
FIG. 3 shows a computer-implemented method in accordance with an embodiment of the present invention.

FIG. 3 shows a computer-implemented method 300 for providing alignment information data for the alignment of an orthopaedic implant for a joint of a patient in accordance with an embodiment of the present invention. The computer-implemented method 300 is suited for implementation on one or more computing devices 100 and in particular one or more computing devices 100 communicating across a network 200, as substantially shown in FIG. 2.

Specifically, such a computing device 100 comprises a processor 1000 for processing digital data, a memory device 110 for storing digital data including computer program code and being coupled to the processor 1000 via a communications bus 150, a data interface (180, 140) for sending and receiving digital data and being coupled to the processor 1000 via the bus 150, and a storage device such as a database 1030 for storing digital data including the alignment information data, and library data, and being coupled to the processor 1000 via the bus 150.

Library Data

The library data stored in the database 1030 includes—library alignment information data, library alignment configuration data, and library design data that are indicative of a set of available predetermined simulation models for the movement of a generalized and idealized joint during a respective predetermined post-implant activity. Each simulation model is created by taking various measurements from a sample of test subjects performing movements for the particular predetermined activity. These measurements are collated and processed to produce the ideal simulation model. In embodiments, the ideal simulation models are not only differentiated by the post-implant activity, but also by other factors such as gender data, age data, height data, weight data, activity level data, BMI data, body condition data, and body shape data, medical history, occupation, and race, among others.

The library data also includes library alignment configuration data relating to a group of available orthopaedic implants for performing post-implant activities and library alignment configuration data relating to a group of patients fitted with an orthopaedic implant for performing post-implant activities. The orthopaedic implants may be commercially available orthopaedic implants, or orthopaedic implants that have been customised specifically for previous patients.

The library data also includes library design data for the group of available orthopaedic implants from which the structural parameters of the orthopaedic implants can be derived. The library design data may be provided in the form of, for example, a CAD file.

The library data also includes data relating to the durability and wear of orthopaedic implants that have been prior fitted to patients. Such data can be obtained by using, for example, 2D and 3D imaging techniques such as Magnetic Resonance Imaging (MRI) data, Computed Tomography (CT) data, ultrasound data, and radiological data, and recording such data at various time intervals. The obtained durability and wear score data associated with the orthopaedic implants can then be used to assist an operator, such as a surgeon, in predicting how well an orthopaedic implant having the same structural parameters that a now worn orthopaedic implant had prior to being implanted, will perform in another patient.

The library data may also include subjective metrics relating to a patient's own view of the biomechanical performance of their joint post-implant surgery, and objective metrics directed to the patient by the operator, such as a surgeon, to understand how the joint and the orthopaedic implant are actually performing post-implant surgery, in quantifiable terms.

The computer-implemented method 300 starts at step 310 where the processor 1000 is controlled by the computer program code to receive, via the data interface (180, 140), patient specific information data specific to the patient to be fitted with an orthopaedic implant, and indicative of one or more dynamic characteristics. The patient specific information data is buffered and then compiled by the computing device 100 as patient file 7 in an electronic form for storing in the database 1030. The processor 1000 is further controlled by the computer program code, at step 320, to calculate patient data according to the patient specific information data contained within the patient file 7. In this step, the computing device 100 receives the patient file 7 from the database 1030 via bus 150 and then derives at least a portion of the patient data by virtue of segmenting and filtering out any unwanted data from the patient file 7. Such unwanted data may include a variety of information that represents non-essential tissues in the joint, for example muscle, fat and skin, amongst others. This allows the isolation and more streamlined analysis of only the relevant data. This filtration of unwanted data can be partially automated but for the present embodiment, manual inputs are generally required.

Patient Specific Information Data

The patient specific information data comprises 2D and 3D imaging data of the bone geometry of the joint. The 2D imaging data comprises data obtained using such techniques as X-Ray and visual fluoroscopy, while the 3D imaging data comprises data obtained using such techniques as Magnetic Resonance Imaging (MRI) data, Computed Tomography (CT) data, ultrasound data, and radiological data. The patient specific information data also comprises 4D imaging data obtained using such techniques as motion capture. Such 4D imaging may entail placing markers (not shown) at various locations on the relevant bones associated with the joint and then tracking the motion of the markers as the patient engages in a desired activity.

The patient specific information data also comprises data indicative of one or more physical characteristics of the patient, such as: age data, gender data, height data, weight data, activity level data, BMI data, body condition data, race, and body shape data, among others. Other patient specific information data may comprise data indicative of the history of the patient and the history of other family members for the purpose of identifying any heredity defects that have occurred, or might occur in the patient in the future.

Once the patient file 7 has been filtered, relevant anatomical landmarks in the joint are then manually identified and identification instructions are entered via the data interface (180, 140). The computing device 100 is responsive to the identification instructions to define at least another portion of the patient data from the highlight identified landmarks. It has been found that each joint has special anatomical features that need to be considered. Examples of such landmarks include bony protuberances called prominences, lines between landmarks, and ligament and tendon insertions and attachments.

In embodiments, relevant anatomical landmarks in the joint are automatically identified using such processes as functional referencing, algorithmic identification of anatomy, and algorithmic identification of moment arms. In other embodiments, semi-automatic identification of relevant anatomical landmarks is used such as forms of functional imaging, including visual fluoroscopy and endoscopy.

Figure 13:
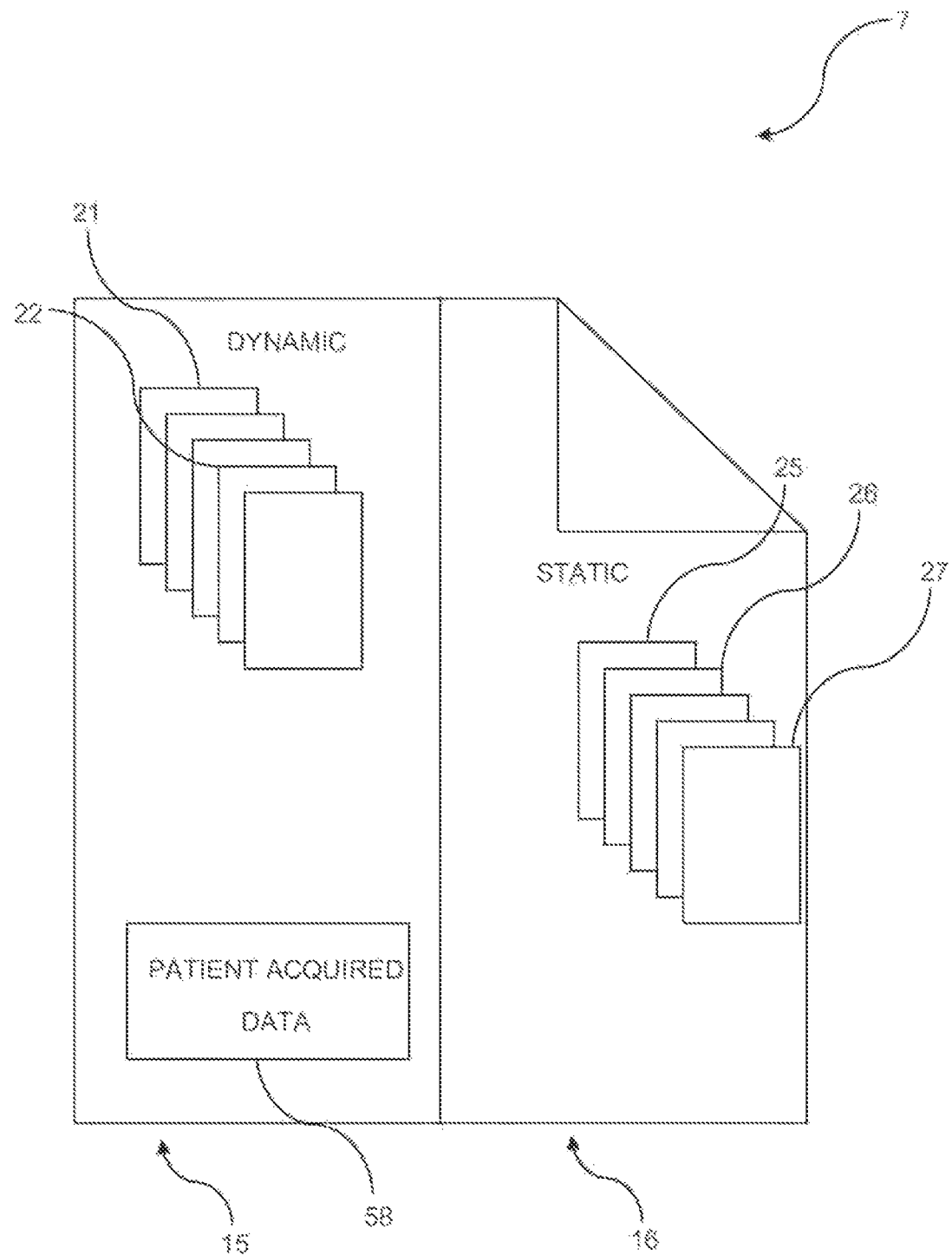
FIG. 13 is a schematic representation of a file stored in a database of the computing device of FIG. 1.

As shown in FIG. 13, the patient file 7 comprises first and second data 15 and 16. Data 15 includes information records indicative of one or more dynamic characteristics and data 16 includes information records indicative of one or more static characteristics.

Dynamic Characteristics

The dynamic characteristics of the joint comprise data in the form of a virtual prediction, namely a computer model prediction based on joint kinematics data, joint loading data, and joint articulation behaviour data in response to particular movements, patient specific loads, moment arms, contact stresses, external forces, and muscle forces, amongst others, associated with the patient's desired post-implant activities.

Data 15 is based on an array of records, where each record corresponds to a selected one of the set of available predetermined ideal simulation models included within the library alignment information data, library alignment configuration data, and library design data stored in the database 1030.

Each model in the set of models corresponds to a particular joint performing a particular activity. For example, a record 21 included in data 15 corresponds to a model of the movements anticipated to be performed by a generalized knee joint at those times when the associated human body is partaking in a game of tennis. That is, this model provides the ideal knee joint configuration and range of articulation, amongst other quantifiable factors, for a person playing tennis based on the specific movements a tennis player makes. A record 22 corresponds to a model of the movements of a generalized knee joint when the associated human body is undertaking the action of climbing up and down a staircase and includes a plurality of quantifications (of different quantum).

In other embodiments, data 15 is based upon a single record.

In one embodiment, data 15 is indicative of at least two simulation models. In further embodiments, data 15 is indicative of more or less than two simulation models.

Static Characteristics

Data 16 is indicative of the static characteristics of the joint and includes one or more stationary measurements taken of the joint and/or of its alignment relative to other physiological components specific to the patient. Available stationary measurements comprise: the mechanical axis alignment; a range of motion simulations based on implant shape and patient anatomy; and others that would be appreciated by those skilled in the art given the benefit of the teaching herein. In the case of the mechanical axis alignment data, such data corresponds to the particular mechanical load bearing axes of a biomechanical reference frame associated with the joint. In the case where the joint corresponds to a knee or hip joint, then such biomechanical reference frames include the acetabular reference frame, the femoral reference frame, the tibial reference frame, and the spinal reference frame. Such mechanical load bearing axes when combined result in a primary mechanical load bearing axis, corresponding to the overall mechanical axis alignment of the joint. It will be appreciated that the biomechanical reference frames are not limited to those related to the knee and hip as described above, but may also include reference frames associated with other joints of the body including the shoulder, and ankle, among others.

As shown in FIG. 13, data 16 includes an array of records corresponding to static properties or characteristics of the joint. More particularly, in this embodiment, data 16 contains a plurality of images of the joint. These images include a Magnetic Resonance Imaging (MRI) image, in the form of record 25, a Computed Tomography (CT) image, in the form of record 26, and an X-ray image, in the form of record 27. Embedded and inherent within, and extractable from, these images are many stationary or static measures for the joint.

Records 25, 26 and 27 are in DICOM (Digital Imaging and Communications in Medicine) format for allowing, as will be described below, the automated extraction of a number of static characteristics of the joint. In other embodiments, records 25, 26 and 27 are an image that is digitized for then allowing the required characteristics to be extracted. In other embodiments, records 25, 26 and 27 is other than a DICOM format which still allows automated extraction of a number of static characteristics of the joint.

In other embodiments, data 16 is indicative of information other than images, while in further embodiments, different images are used instead of or in addition to those explicitly mentioned above. Examples of other images include ultrasound images, laser scans, and scans from point matching, surface matching and/or surface recognition, amongst others. It is also appreciated that a person skilled would recognize with the benefit of the teaching herein, that such images are able, in some instances, to be used to derive one or more of the records included in data 15.

In summary, the filtered and identified information from the patient file 7 defines the patient data, which is then stored in the database 1030.

At step 330, the processor 1000 is further controlled by the computer program code to calculate the alignment information data for aligning the orthopaedic implant for the joint according to the patient data. In this step, the patient data is retrieved from the database 1030 and a deterministic patient specific rigid body mechanics simulation is performed on the patient data using a physics engine, that is, a simulation of the joint using multi-body simulation software.

The simulation is a multi-body simulation which could include the use of forward and/or inverse dynamics in order to produce knee or hip joint simulations.

The alignment information data comprises an actual 3D model data of the joint, as obtained from the various 2D and 3D imaging data stored in data 16. From data 15 and data 16, it is possible to generate data corresponding to magnitudes and directions of force vectors, loads, shear stresses, and moments associated with the orthopaedic implant during the simulation. The alignment information data thus takes into consideration both location information data and orientation information data for locating and orienting, respectively, the orthopaedic implant relative to the joint.

At step 340, the processor 1000 is controlled by the computer program code to receive, via the data interface (180, 140), patient acquired data 58 indicative of one or more desired post-implant activities of the patient. The one or more post-implant activities relate to the number and type of activities that the patient would like to eventually fulfil after an implant operation has been undertaken. In this embodiment, the post-implant activities are categorized into day to day activities (such as, for example, climbing up and down a stair case, getting in and out of a car, picking up their grandchildren), outdoor activities (for example kneeling in the garden for the purposes of gardening, casual jogging) and sporting activities (such as, for example, playing tennis, golf, skiing, football, or any defined kinematic propositions). It will be appreciated that in other embodiments, the post-implant activities are not limited to those described above, but may comprise any desired activity of the patient. Such patient acquired data 58 is obtained by virtue of the patient communicating remotely with the computing device 100 via a client computing device 220. The client computing device 220 comprises an interface for sending and receiving digital data and is coupled, across a data link, to the computing device 100. The patient provides the patient acquired data 58 in the form of an electronic questionnaire (not shown), which is submitted by the patient or a healthcare professional via the client computing device 220 to the computing device 100. The patient acquired data 58 is stored as a record in data 15 in the patient file 7 in the database 1030.

The patient acquired data 58 comprises post-implant activities preference data, which is a preference ratio being indicative of comparative patient preference for the one or more desired post-implant activities. In this sense, the patient can order their preferred post-implant activities in terms of specific personal preference. For example, where one patient wishes to be able to kneel in the garden so as to attend to gardening, and occasionally play tennis, the preference ratio orders kneeling in the garden ahead of playing tennis. In the case of a knee joint, the action of kneeling would require extensive flexion of the joint, but minimal varus/valgus and internal/external rotation of the joint. On the other hand, the action of playing tennis would require a greater degree of varus/valgus and internal/external rotation of the joint.

Other types of patient metrics that may appear in the questionnaire could include subjective metrics relating to the patient's own view of the biomechanical performance of the joint pre-implant surgery, and objective metrics directed to the patient by the operator, such as a surgeon, to understand how the joint is actually performing pre-implant surgery, in quantifiable terms. A surgeon can use such patient metrics to understand the current limitations of the patient's joint.

Essentially, the questionnaire provides a predetermined list of post-implant activities of which the patient would rate in order of personal preference. The post-implant activities preference data thus forms a patient functional score that can then be used to define boundary conditions in a multi-body simulation to assist an operator in identifying the most appropriate orthopaedic implant to enable the patient to achieve the desired post-implant activities.

In other embodiments, the questionnaire is a paper survey (not shown) that is filled out by the patient and then entered manually into the database 1030 by, for example, an operator or a surgeon, via the data interface (180, 140).

In other embodiments, the patient acquired data 58 is input into the questionnaire remotely via a personal digital assistant (PDA) such as, for example, an iPhone and/or iPad application (not shown).

At step 350, once the patient acquired data 58 has been input by the user, the processor 1000 is controlled by the computer program code to calculate a set of possible alignment information data according to the patient data and the patient acquired data 58. In this step, the simulation of the joint is tested against the patient acquired data 58 with respect to the post-implant activities. This is known as the improvement approach. Essentially, this step examines the simulated joint in conjunction with the desired motion of the post-implant activities to show where, amongst others, the maximum functional kinematic response will occur on the patient's joint for that particular movement. The set of possible alignment information data thus takes into consideration the alignment information data relating to the actual joint of the patient in its current state and the alignment information data that would enable the patient to perform the desired post-implant activities.

At step 360, the processor 1000 is controlled by the computer program code to select alignment information data from the set of possible alignment information data according to the post-implant activities preference data. In this step, once the one or more points of maximum functional kinematic response are identified, certain variables, for example, the positioning and shape of the articulation surface of the orthopaedic implant are varied as desired to thereby produce a simulation file, which is stored in the database 1030 for future access by the operator or by one or more remote users. The selected alignment information data thus relates to alignment information data that would enable the patient to perform their desired post-implant activities according to their personal preference. So, for the example above, the selected alignment information data would allow a high degree of flexion of the knee joint to allow the patient to preferentially perform the action of kneeling in the garden, but still have a reasonable degree of varus/valgus and internal/external rotation of the joint to afford the patient with the ability to play the occasional game of tennis.

The simulation file is a DICOM (Digital Imaging and Communications in Medicine) file comprising 2D slices that can be viewed in 3D by compiling the 2D slices using image processing software. In other embodiments, other image filetypes are used such as STL, JPEG, GIF, and TIF.

In other embodiments, operators can virtually implant an orthopaedic implant into the joint of the patient in order to identify optimal alignment configurations and orientations of that orthopaedic implant that will yield the best biomechanical performance for the desired post-implant activities.

At step 370, the processor 1000 is further controlled by the computer program code to load, from the database 1030, library alignment information data corresponding to alignment information data relating to a group of available orthopaedic implants for performing at least one of the one or more desired post-implant activities or alignment information data relating to a group of patients fitted with an orthopaedic implant for performing at least one of the one or more desired post-implant activities. In this step, the alignment information data for aligning the orthopaedic implant to the joint of the patient can be further improved by virtue of comparing the selected alignment information data for the simulated joint developed by the multi-body simulation with the library alignment information data associated with commercially available orthopaedic implants or patients fitted with orthopaedic implants that are known to be suitable for performing at least one of the one or more desired post-implant activities of the patient.

The data interface (180, 140) is responsive to a user input from the client computing device 220 to enable a remote user, such as a surgeon, to access the simulation file from the database 1030 to generate, buffer and display, for example, a graphic representation of the joint derived from the simulation file. The data interface (180, 140) is also accessible by remote users by logging on to a web page (not shown) via the Internet 230 using, for example, a pre-defined username and/or password.

It will be appreciated that all data stored in the database 1030 is categorized with a security level and all remote users accessing the data via a client computing device 220 will have an allocated security access rights. Access to any specific data is regulated based upon not only the security level of the data itself and the security access rights of the remote user seeking access to the data, but also on the relationship between the patient from whom the data is derived and the user. In this way, the operator assisting the patient is able to selectively input at least some of the patient specific information data, such as CT scans and MRI scans for the patient, as well as personal preferences for the post-implant activities. In other embodiments, more or less access to information is provided to selected persons.

Selecting an Implant from Group of Implants

Figure 4:
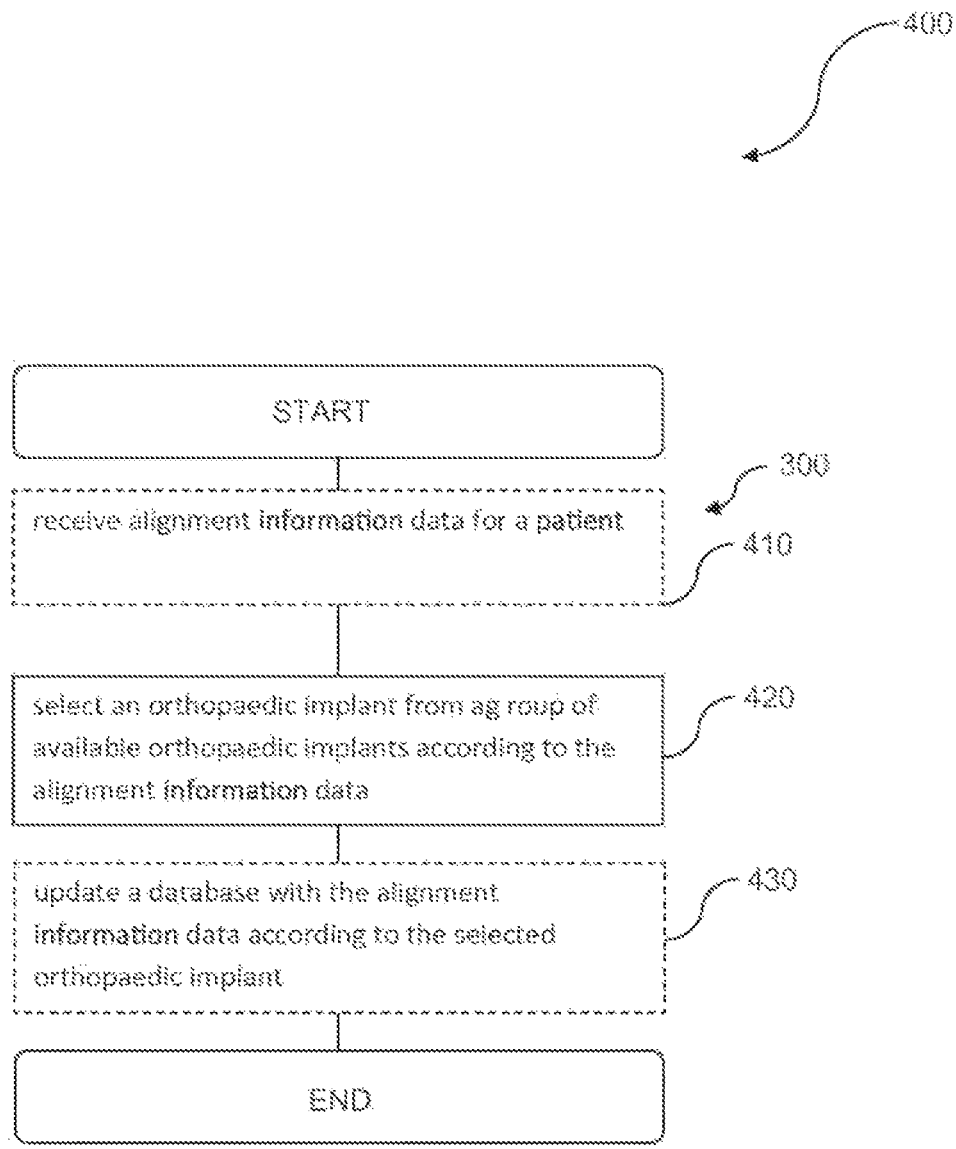
FIG. 4 shows a computer-implemented method in accordance with an embodiment of the present invention.

FIG. 4 shows a computer-implemented method 400 for selecting an orthopaedic implant for a joint of a patient from a group of available orthopaedic implants in accordance with another embodiment of the present invention. The computer-implemented method 400 starts at step 410 where the processor 1000 is controlled by the computer program code to receive from the database 1030, via the data interface (180, 140), the alignment information data for the alignment of the orthopaedic implant calculated according to the computer-implemented method 300 described above, and to then use this calculated alignment information data, at step 420, to select an orthopaedic implant from a group of available orthopaedic implants.

In one embodiment, the group of available orthopaedic implants relates to a group of generic, commercially available implants, which have been manufactured for the purpose of providing implants to fit a range of patients. It will be appreciated each implant within the group of generic orthopaedic implants has structural parameter data that can be used in the computer-implemented method 400 to enable an operator such as a surgeon, to compare the alignment information data of the patient with the known structural parameter data of the generic orthopaedic implants to aid in the selection of an orthopaedic implant of most appropriate fit with respect to the patient's joint.

Once the most appropriate orthopaedic implant has been selected, the processor 1000 is then further controlled by the computer program code at step 430, to update the database 1030 by virtue of sending, via the data interface (140, 180), the corresponding alignment information data associated with the patient's joint to the database 1030 for use in future data requests relating to the selection of an orthopaedic implant for the same patient or another patient.

Aligning an Implant

Figure 5:
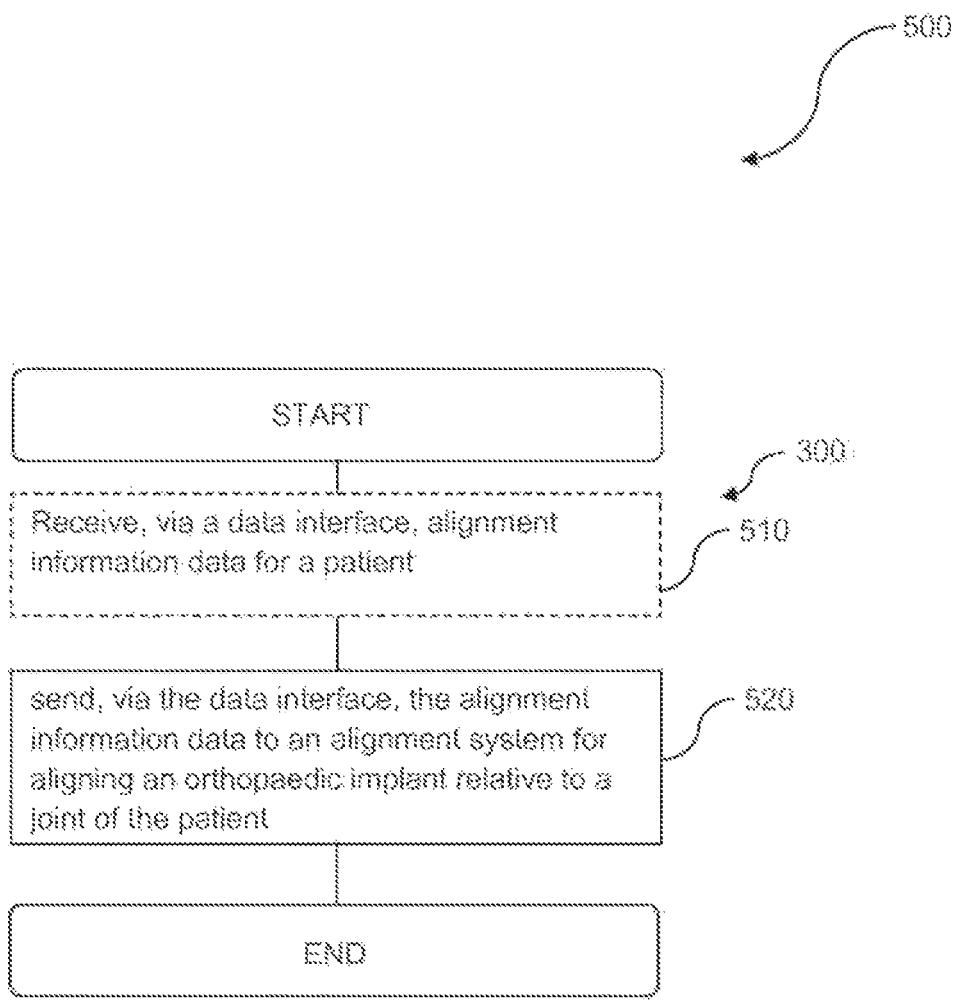
FIG. 5 shows a computer-implemented method in accordance with an embodiment of the present invention.

FIG. 5 shows a computer-implemented method 500 for aligning an orthopaedic implant for a joint of a patient in accordance with another embodiment of the present invention. The computer-implemented method 500 starts at step 510 where the processor 1000 is controlled by the computer program code to receive, via the data interface (140, 180), the alignment information data calculated according to the computer-implemented method 300 described above, and to then send this calculated alignment information data, via the data interface (140, 180), at step 520, to an alignment system (not shown) such as a robotic alignment system, a haptic feedback alignment system, a computer-assisted alignment system, or any standard or custom-made instrument, for use in controlling the alignment system to physically align the orthopaedic implant for the joint of the patient in a corresponding surgical procedure. In this arrangement, the alignment system is connected to the computing device 100 by virtue of a wired network, such as a wired Ethernet™ network or a wireless network, such as a Bluetooth™ network or IEEE 802.11 network.

In one embodiment, the calculated alignment information data is sent directly to the alignment system, via the data interface (140, 180), by virtue of a direct network connection over a wide area network (WAN), such as the Internet 230 or private WAN.

In one embodiment, the alignment information data is transferred to the alignment system indirectly in the form of a robotics file (not shown) comprising the alignment information data as instructions for controlling the alignment system to perform the alignment of the orthopaedic implant for the joint. The robotics file may be transferred to an operator of the alignment system via electronic mail or file transfer process (FTP) over the Internet 230 or private WAN.

In one embodiment, the robotics file is loaded onto one or more storage media (not shown) such as, for example, CD-ROM disks, floppy disks, tape cassettes, or USB memory sticks, and physically transferred to the operator of the alignment system for direct input into the alignment system.

Modelling an Alignment of an Implant

Figure 6:
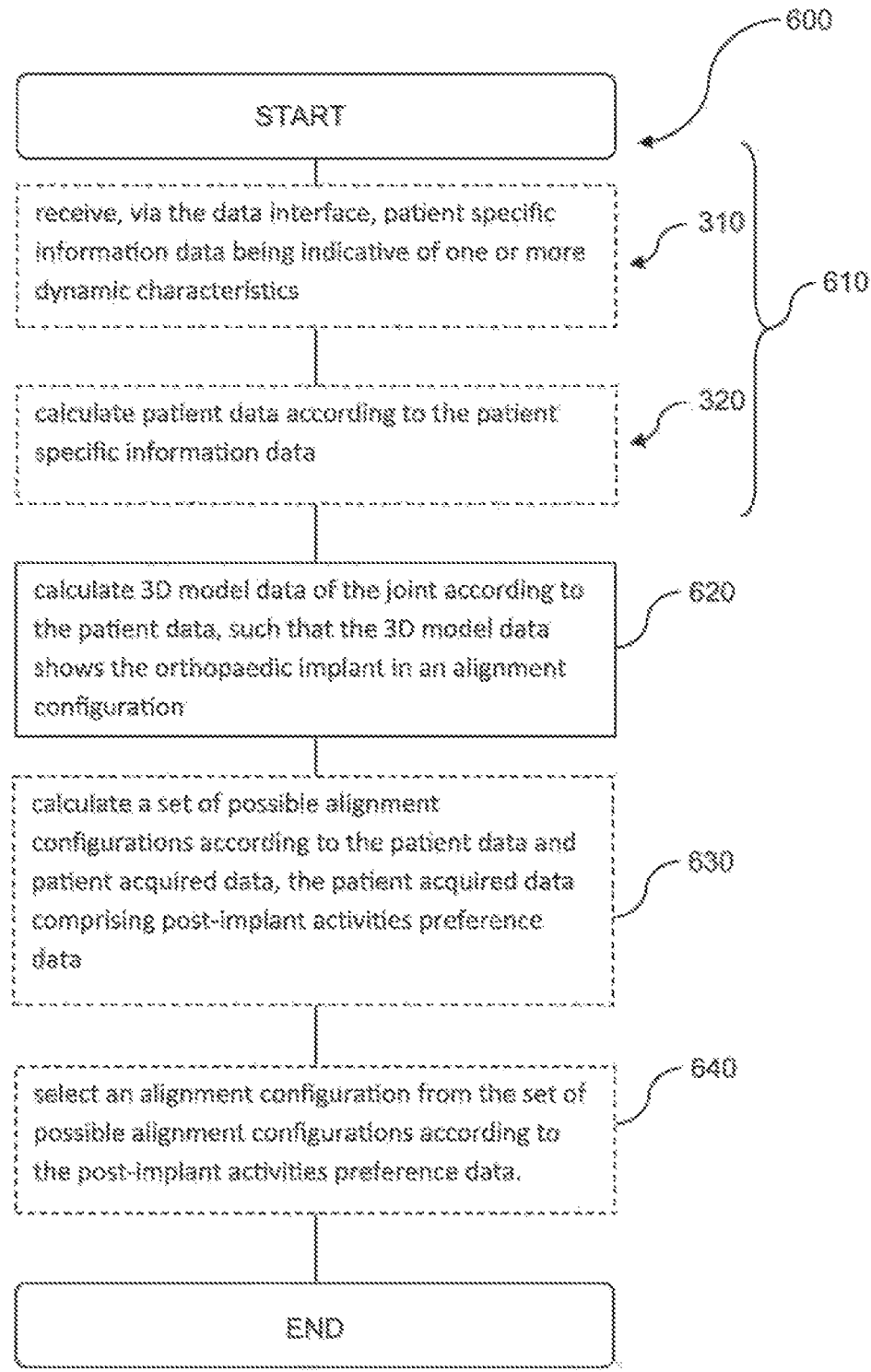
FIG. 6 shows a computer-implemented method in accordance with an embodiment of the present invention.

FIG. 6 shows a computer-implemented method 600 for modelling the alignment of an orthopaedic implant for a joint of a patient in accordance with another embodiment of the present invention. The computer-implemented method 600 starts at step 610, by deriving the patient data from the patient specific information data according to the computer-implemented method 300 described above. The processor 1000 is then further controlled by the computer program code to calculate at step 620, 3D model data of the joint according to the alignment information data. The 3D model data when viewed as a graphical representation on the display device 1020 provides a schematic dynamic 3D model of the joint, which can then be manipulated as desired by, an operator, such as a surgeon, and used to enable the operator to visualize the effect and dynamics of the orthopaedic implant in position.

In one embodiment, the processor 1000 is controlled by the computer program code to calculate, at step 630, a set of possible alignment configurations according to the alignment information data and the patient acquired data 58. The calculated set of possible alignment configurations thus takes into consideration the 3D model and the one or more post-implant activities the patient wishes to engage in after the orthopaedic implant has been fitted to the joint to establish alignment configurations that would allow the patient to perform such post-implant activities. By then taking into consideration the post-implant activities preference data relating to the patient's preference for performing the post-implant activities, the processor 1000 is further controlled by the computer program code, at step 640, to select an alignment configuration from the set of possible alignment configurations calculated above according to the post-implant activities preference data. As a result, the selected alignment configuration when viewed as a graphical representation on the display device 1020 enables the operator to visualize the joint of the patient and visualize how the orthopaedic implant can be aligned relative to the joint to achieve the desired post-implant activities.

Selecting an Implant from a Group of Implants According to 3D Model Data

Figure 7:
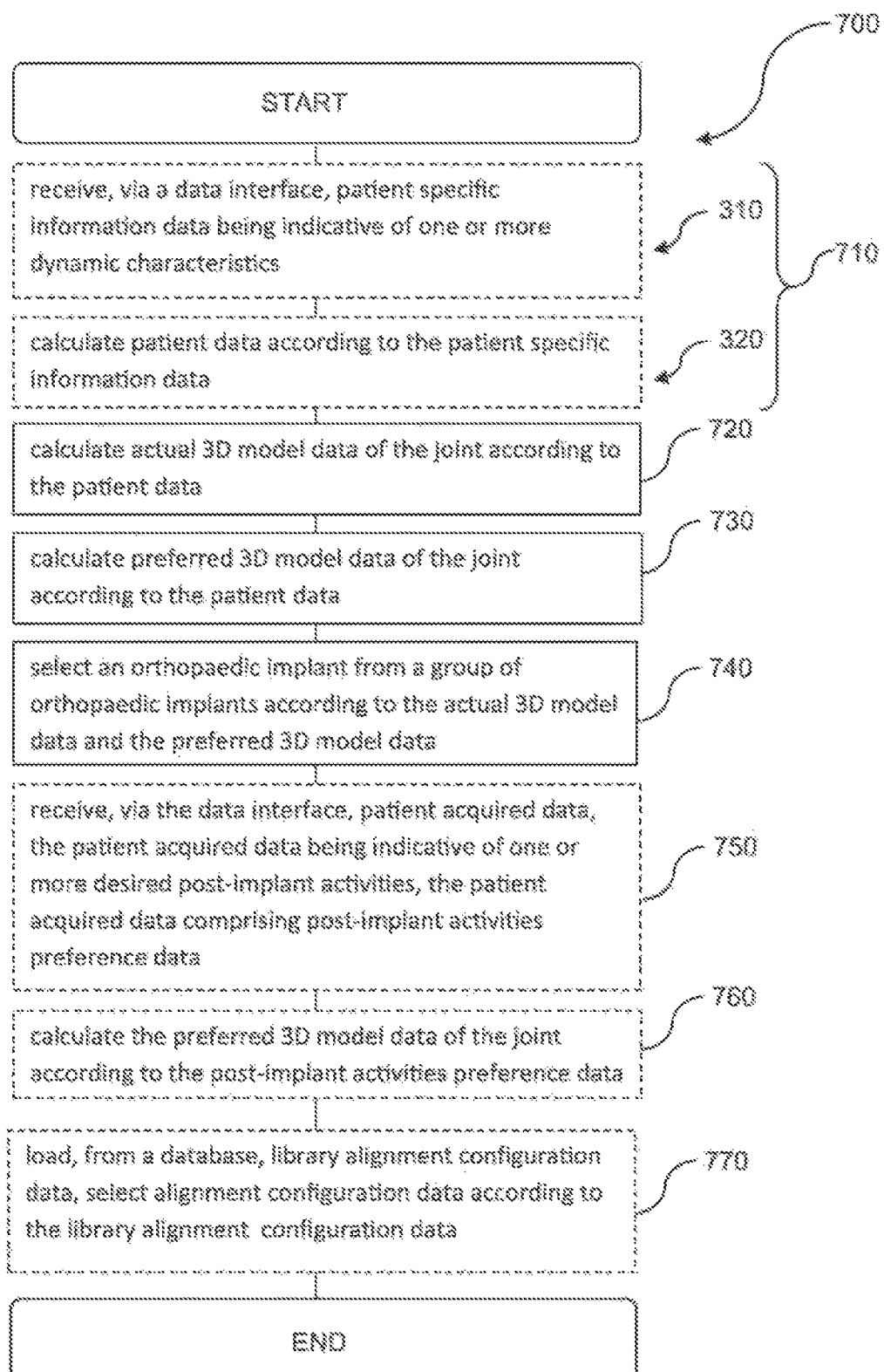
FIG. 7 shows a computer-implemented method in accordance with an embodiment of the present invention.

FIG. 7 shows a computer-implemented method 700 for selecting an orthopaedic implant for a joint of a patient from a group of orthopaedic implants in accordance with another embodiment of the present invention. The computer-implemented method 700 starts by deriving the patient data from the patient specific information data according to steps 310 and 320, and then uses the patient data to calculate the actual 3D model data of the joint according to step 720.

The processor 1000 is then further controlled by the computer program code to calculate, at step 730, preferred 3D model data of the joint according to the patient data. In this step, a deterministic model of the joint is developed when the simulation is performed by an operator according to the above computer-implemented method 700 to produce a simulation model of a "preferred" joint that takes into consideration both the dynamic characteristics and the static characteristics described above. The processor 1000 is further controlled by the computer program code, at step 740, to select an orthopaedic implant from a group of orthopaedic implants according to the actual 3D model data and the preferred 3D model data. In this step, the operator can use the preferred 3D model data of the joint in order to select an orthopaedic implant that most closely recreates the results proposed by the preferred 3D model data.

In one embodiment, the processor 1000 is controlled by the computer program code to receive, via the data interface (140, 180), at step 750, patient acquired data 58, being indicative of the one or more desired post-implant activities, in which the patient acquired data comprises post-implant activities preference data. By then taking into consideration the post-implant activities preference data relating to the patient's preference for performing the post-implant activities, the processor 1000 is further controlled by the computer program code, at step 760, to calculate the preferred 3D model data of the joint according to the post-implant activities preference data. As a result the preferred 3D model data takes into consideration the patient's desired post-implant activities to produce a simulation model of the joint that would enable the patient to perform their desired post-implant activities.

In one embodiment, the computer-implemented method 700 is taken one step further to take into consideration library alignment configuration data relating to a group of available orthopaedic implants for performing at least one of the one or more desired post-implant activities or library alignment configuration data relating to a group of patients fitted with an orthopaedic implant for performing at least one of the one or more desired post-implant activities. In this embodiment, the processor 1000 is controlled by the computer program code, at step 770, to load from the database 1030, the library alignment configuration data, and to then select the orthopaedic implant according to the library alignment configuration data. In this step, the preferred 3D model of the joint is further calculated based on an improvement of the actual 3D model data according to a comparison with the known library alignment configuration data.

As a result of the embodiments, the preferred 3D model data of the joint when viewed as a graphical representation on the display device 1020 enables the operator to visualize and compare how the preferred 3D model of the joint will align with selected orthopaedic implants from the library alignment configuration data and how the orthopaedic implants are likely to perform functionally for specific post-implant activities. An operator is thus able to select the orthopaedic implant from the group of available orthopaedic implants that would best suit the patient to enable them to perform the desired post-implant activities according to their desired preference.

In use, the above described modelling technique is applied to testing predetermined orthopaedic implants at predetermined alignment configurations. The simulation file can then be viewed as, for example, a graphical representation, by the operator who can then extract information regarding the functional kinematic response on the patient's joint fitted with the predetermined orthopaedic implant and the predetermined alignment configuration. The surgeon can then choose to run another simulation with a different predetermined orthopaedic implant and/or a different predetermined alignment configuration in response to information regarding, for example, stress on the patient's joint based on the first simulation operation. This process is then repeated, as desired, until the surgeon is happy with the predetermined implant and the predetermined alignment configuration.

Figure 12:
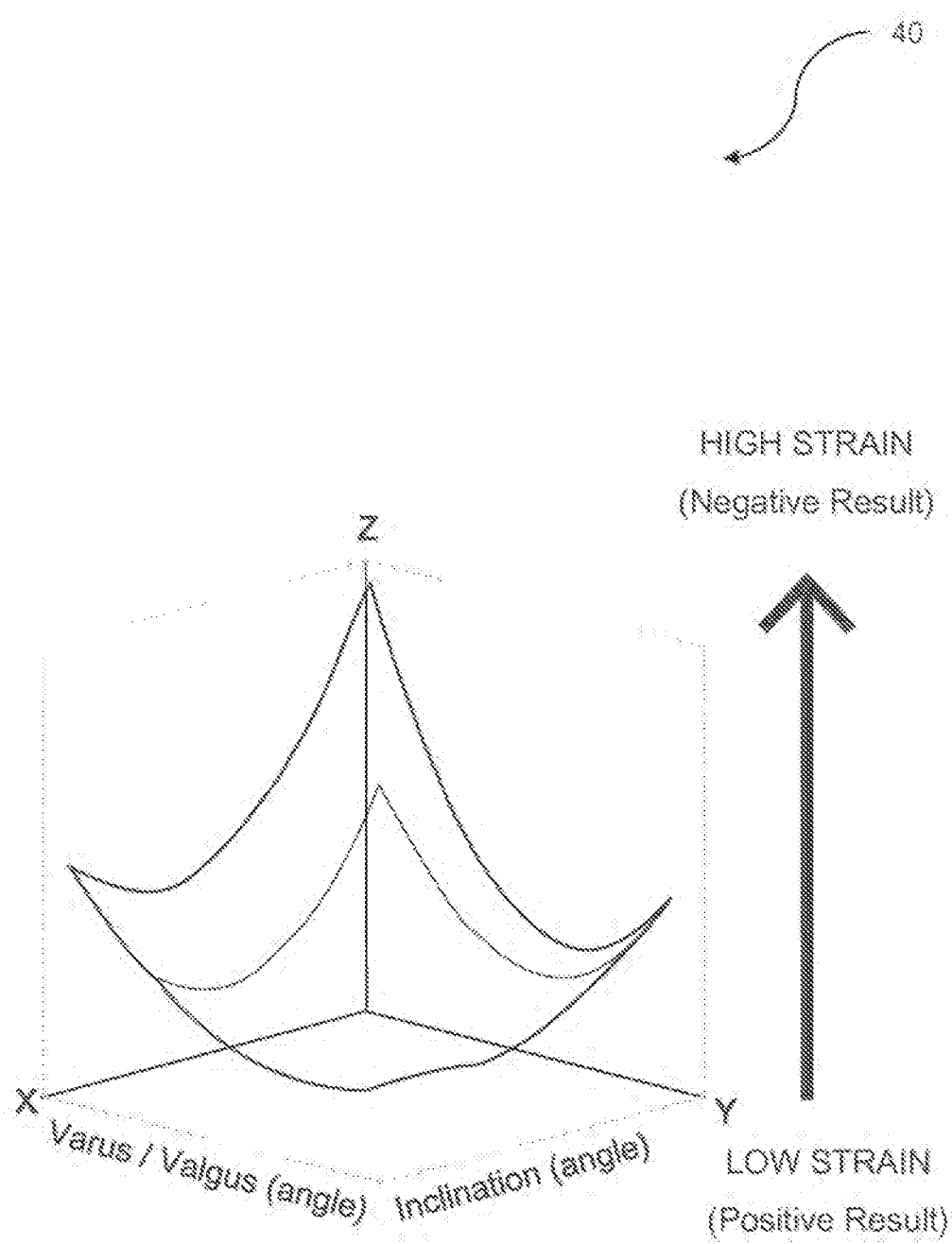
FIG. 12 is a graphic representation of a response curve demonstrating a functional kinematic response for a knee joint.

It will be appreciated that the graphical representation is not limited to displaying a schematic 3D model of the joint, but may in various embodiments, also include graphical representations of a model of the joint using a predetermined orthopaedic implant, a model of the patient's joint using a predetermined alignment configuration, or a graphical response curve showing such information as joint stress in response to the choice or orthopaedic implant and choice of alignment configuration. The graph 40 of FIG. 12 is an example of a response curve showing the level of strain on a model of a joint.

Manufacturing Parameters
Orthopaedic Implant

Figure 8:
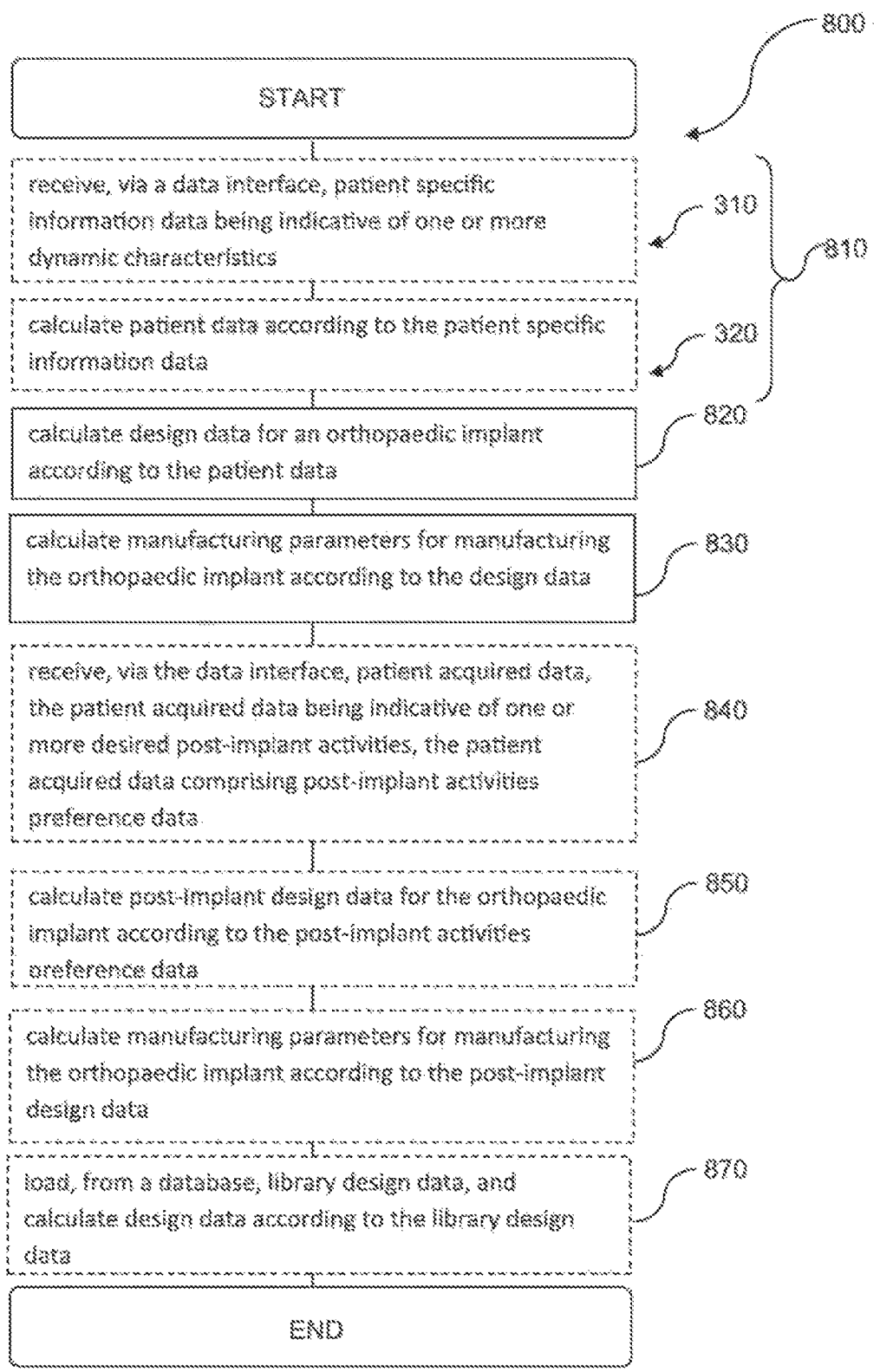
FIG. 8 shows a computer-implemented method in accordance with an embodiment of the present invention.

FIG. 8 shows a computer-implemented method 800 for developing manufacturing parameters for manufacturing an orthopaedic implant for a joint of a patient having an orthopaedic implant articulation surface in accordance with another embodiment of the present invention. The computer-implemented method 800 starts, at step 810, by deriving the patient data from the patient specific information data according to steps 310 and 320. At step 820, the processor 1000 is then further controlled by the computer program code to calculate design data for the orthopaedic implant according to the patient data. In this step, the design data relates to the structural parameters of the whole orthopaedic implant including the articulation surface of the orthopaedic implant. In other embodiments, the design data only relates to structural parameters of the articulation surface.

At step 830, the processor 1000 is further controlled by the computer program code to calculate the manufacturing parameters, such as a 3D CAD model, for manufacturing the orthopaedic implant according to the design data. The developed manufacturing parameters can then be used in the manufacture of the orthopaedic implant using one or more suitable manufacturing processes. Such manufacturing processes may comprise an additive manufacturing process, such as stereolithography (SLA), selective laser sintering (SLS), direct metal laser sintering (DMLS), electron beam melting (EBM), and 3D printing (3DP), or a subtractive manufacturing process, such as biomachining, abrasive flow machining, abrasive jet machining, milling, laser cutting, and water jet cutting.

In one embodiment, the computer-implemented method 800 is taken one step further to take into consideration the one or more desired post-implant activities of the patient. In this embodiment, the processor 1000 is further controlled by the computer program code, at step 840, to receive, via the data interface (140, 180), the patient acquired data 58, being indicative of the one or more desired post-implant activities, and comprising the post-implant activities preference data, and to then calculate, at step 850, post-implant design data of the orthopaedic implant based on the post-implant activities preference data. In this step, the post-implant design data defines an orthopaedic implant, and in particular the articulation surface of the orthopaedic implant that would enable the patient to perform the desired post-implant activities according to their preference for performing the post-implant activities once the orthopaedic implant has been fitted. The processor 1000 is then further controlled by the computer program code, at step 860, to calculate the manufacturing parameters for manufacturing the orthopaedic implant further according to the post-implant design data.

In one embodiment, the computer-implemented method 800 is taken one step further to take into consideration library design data relating to the design data for a group of available orthopaedic implants for performing at least one of the one or more desired post-implant activities or design data relating to a group of patients fitted with an orthopaedic implant for performing at least one of the one or more desired post-implant activities. In this embodiment, the processor 1000 is controlled by the computer program code, at step 870, to load from the database 1030, the library design data, and to then calculate the manufacturing parameters for manufacturing the orthopaedic implant further according to the known library design data.

As a result of the above embodiments, an operator is thus able to develop manufacturing parameters to be used in the manufacture of an orthopaedic implant for the joint of the patient based on a comparison of the structural parameters of the patient's joint and the known functional capabilities of the group of available orthopaedic implants in the database 1030 that would best suit the patient to enable them to perform the desired post-implant activities according to their desired preference.

Custom Articulation

Figure 9:
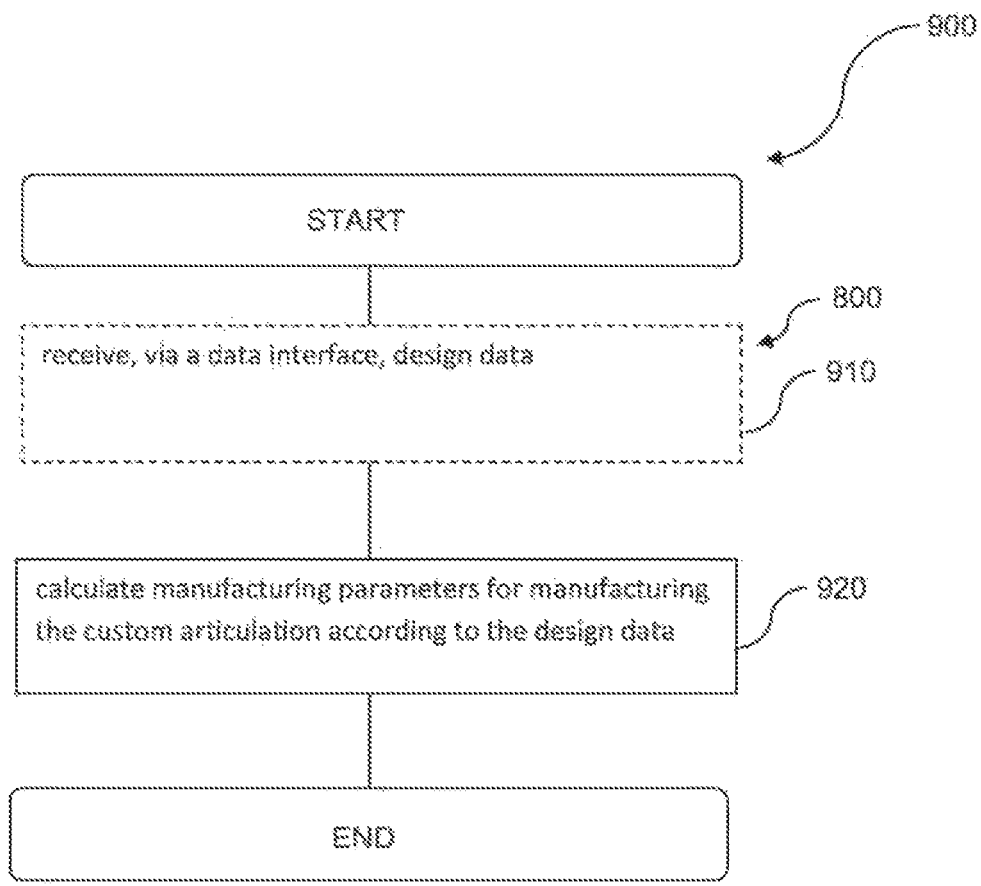
FIG. 9 shows a computer-implemented method in accordance with an embodiment of the present invention.

FIG. 9 shows a computer-implemented method 900 for developing manufacturing parameters for manufacturing a custom articulation (not shown) for attachment to an orthopaedic implant in accordance with another embodiment of the present invention. The custom articulation is part of the orthopaedic implant (generally attached, mechanically locked, or adhered thereto) having the manufacturing parameters as developed above, will best enable the joint to perform desired functional outcomes. The computer-implemented method 900 starts at step 910, by receiving the design data calculated for the orthopaedic implant according to the computer-implemented method 800 as described above. At step 920, the processor 1000 is then further controlled by the computer program code to calculate manufacturing parameters for manufacturing the custom articulation according to the design data. In this step, the manufacturing parameters for the customized articulation implant take into consideration the design data for the orthopaedic implant, in particular the design data that relates to the articulation surface of the orthopaedic implant, and then uses this data to develop an articulation surface for the customized implant that complements the articulation surface of the orthopaedic implant. The developed manufacturing parameters can then be used in the manufacture of the custom articulation using one or more of the manufacturing processes listed above.

As a result of the above embodiments, an operator is thus able to develop manufacturing parameters to be used in the manufacture of a customized articulation implant having a complementary articulation surface to the articulation surface of the manufactured orthopaedic implant described above. In this sense, the orthopaedic implant and the custom articulation, once attached, adhered, or mechanically locked to the corresponding implant (for example, a tibial tray), can be fitted to the joint of the patient to enable the patient to perform the desired post-implant activities according to their desired preference.

Patient Specific Jig

Figure 10:
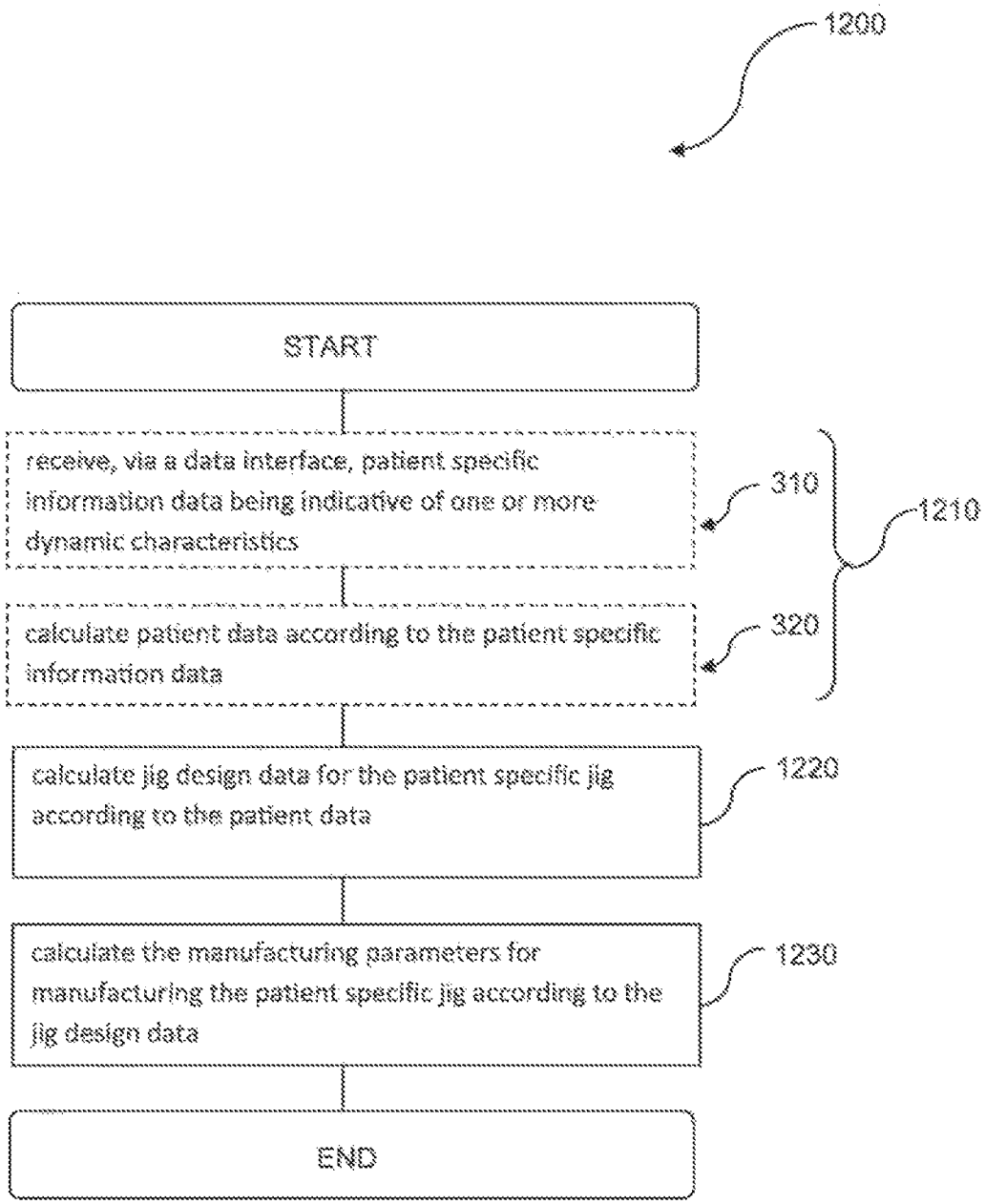
FIG. 10 shows a computer-implemented method in accordance with an embodiment of the present invention.

FIG. 10 shows a computer-implemented method 1200 for developing manufacturing parameters for manufacturing a patient specific jig (not shown) for use in preparing a joint in readiness for aligning an orthopaedic implant to the joint of a patient in accordance with another embodiment of the present invention. In this embodiment, the manufacturing parameters are in the form of a computer file for use by a computer navigation software system or a robotics file for use by a robotics system. The patient specific jig is a cutting guide device which can be mounted to a particular bone of the joint for the purpose of guiding a surgeon during the resectioning, cutting of forming holes in the bones of the joint in order to align the orthopaedic implant with the joint in the same spatial orientation which provides the best overall performance for a particular post-implant activity.

The computer-implemented method 1200 starts, at step 1210, by deriving the patient data from the patient specific information data according to steps 310 and 320. At step 1220, the processor 1000 is then further controlled by the computer program code to calculate jig design data for the patient specific jig according to the patient data. At step 1230, the processor 1000 is then further controlled by the computer program code to calculate manufacturing parameters for manufacturing the patient specific jig according to the jig design data. The developed manufacturing parameters can then be used in the manufacture of the patient specific jig using one or more of the manufacturing processes listed above. As a result, the jig design data relies on the patient data to establish a patient specific jig that can conform to the joint.

FIGS. 14 to 20 illustrate various graphical representations of predicted computer simulation results for a knee joint of a patient based on the alignment information data calculated using the computer-implemented method 300 described above.

Figure 14A:
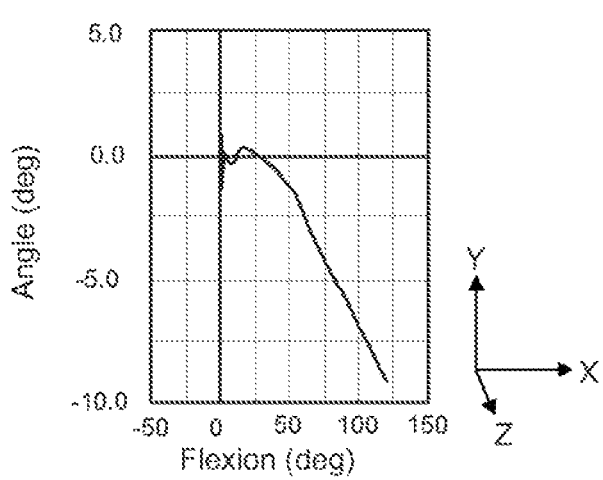
FIGS. 14A, 14B and 14C show graphical representations of predicted computer simulation results for the change in varus angle (in degrees) of a knee joint of a patient based on alignment information data calculated using a computer-implemented method in accordance with an embodiment of the present invention, shown for a generally standing position, FIG. 14A, a generally kneeling position, FIG. 14C, and an intermediate position, FIG. 14B.
Figure 14A:
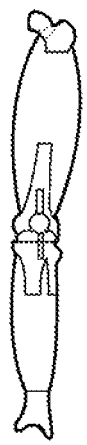
Figure 14B:
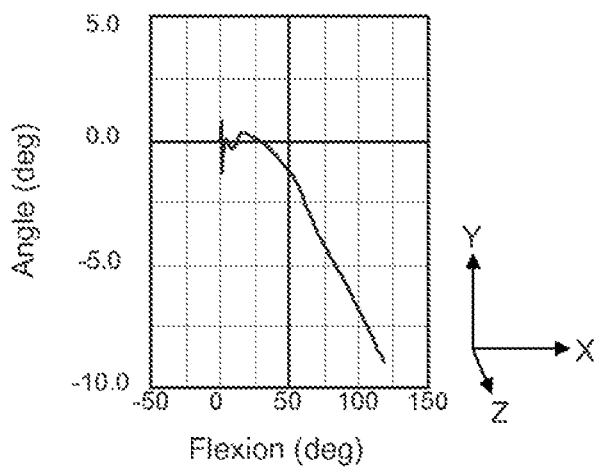
Figure 14B:
Figure 14C:
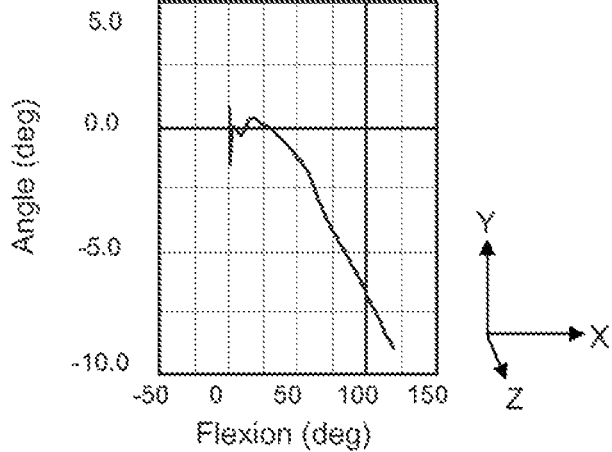
Figure 14C:

FIGS. 14A, 14B and 14C illustrate simulated kinematics results for the change in varus angle (in degrees) of a knee joint as the knee bends or flexes to represent the patient going through the steps of transitioning from a generally standing position, namely a flexion angle of 0 degrees (see FIG. 14AI), to a generally kneeling position, namely a flexion angle of 100 degrees (see FIG. 14C).

Figure 15A:
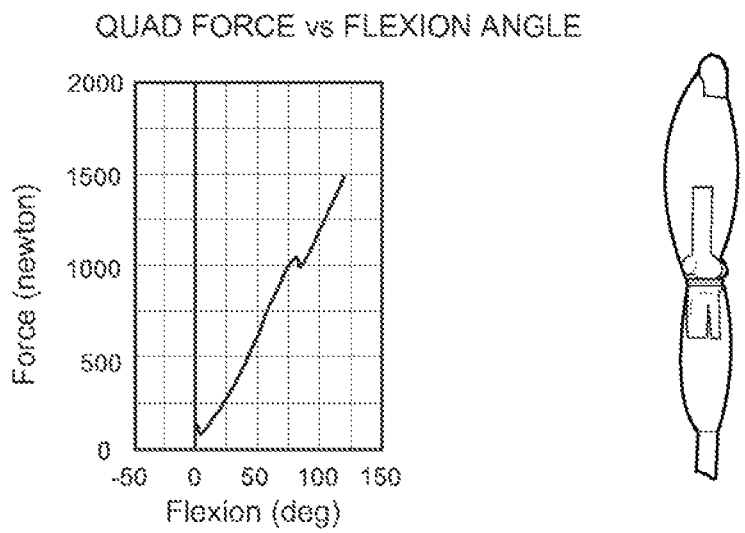
FIGS. 15A, 15B and 15C show graphical representations of predicted computer simulation results for the change in quadricept force (in newtons) of a knee joint of a patient based on alignment information data calculated using a computer-implemented method in accordance with an embodiment of the present invention, shown for a generally standing position, FIG. 15A, a generally kneeling position, FIG. 15C, and an intermediate position, FIG. 15B.
Figure 15B:
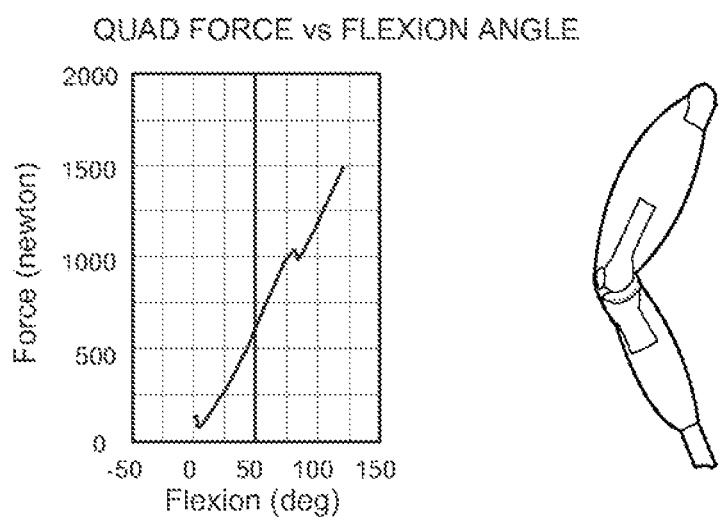
Figure 15C:
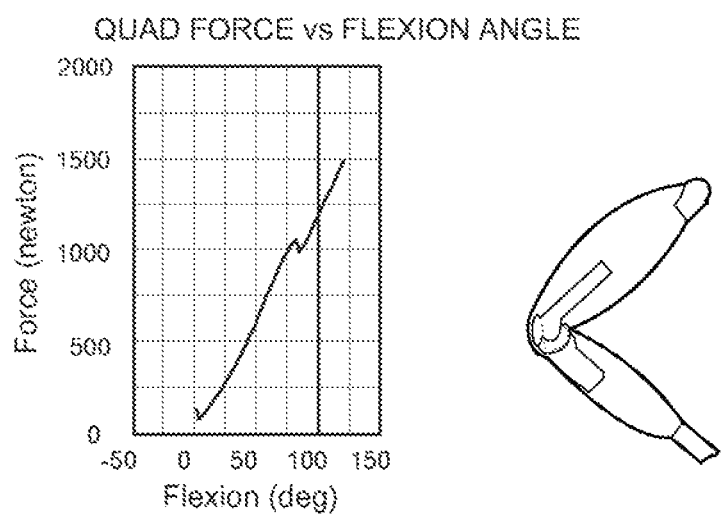

FIGS. 15A, 15B and 15C illustrate simulated kinematics results for the change in quadricept force (in newtons) of a knee joint as the knee bends or flexes to represent the patient going through the steps of transitioning from a generally standing position, namely a flexion angle of 0 degrees (see FIG. 15A), to a generally kneeling position, namely a flexion angle of 100 degrees (see FIG. 15C).

Figure 16A:
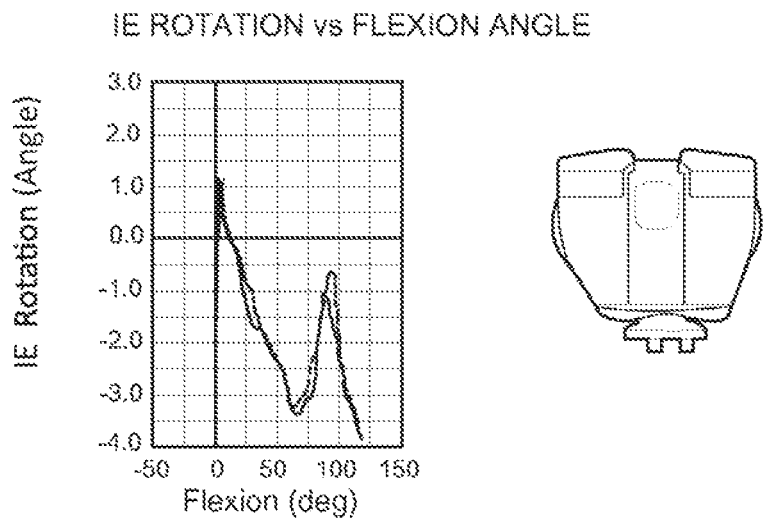
FIGS. 16A, 16B and 16C show graphical representations of predicted computer simulation results for the change in internal-external rotation (in degrees) of a knee joint of a patient based on alignment information data calculated using a computer-implemented method in accordance with an embodiment of the present invention, shown for a generally standing position, FIG. 16A, a generally kneeling position, FIG. 16C, and an intermediate position, FIG. 16B.
Figure 16A:
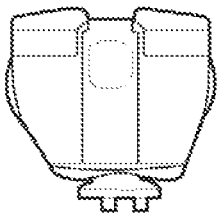
Figure 16B:
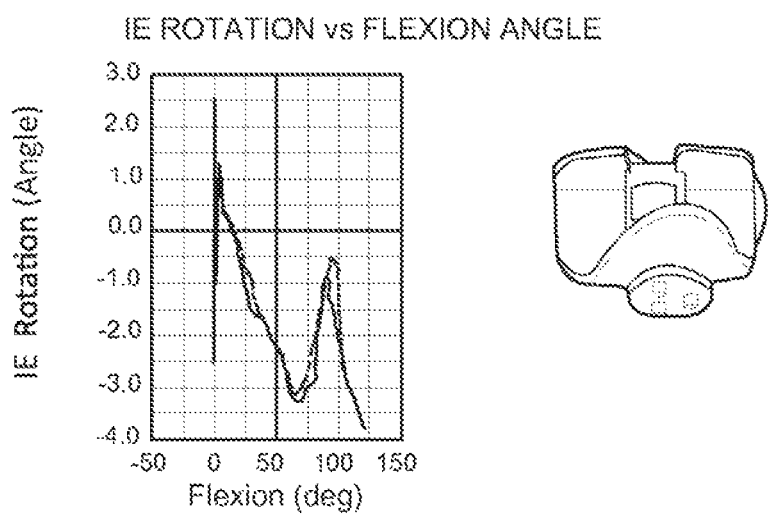
Figure 16B:
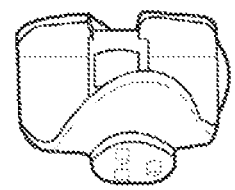
Figure 16C:
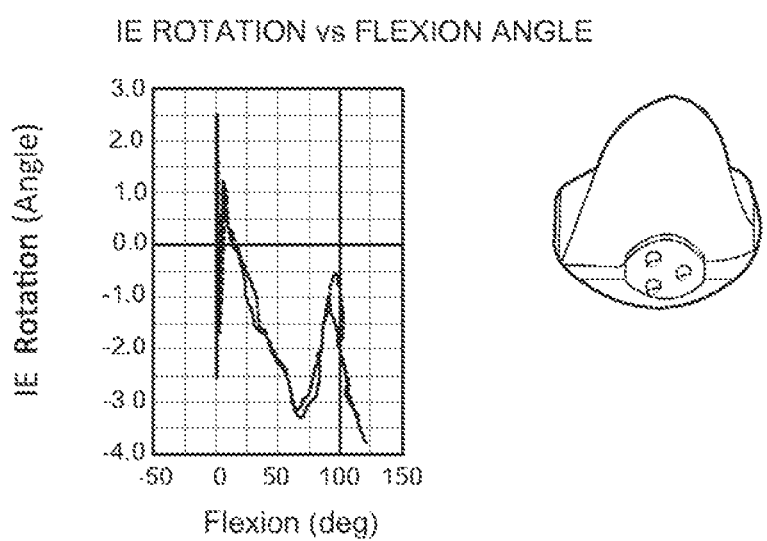
Figure 16C:
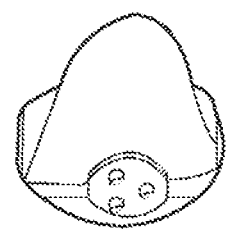

FIGS. 16A, 16B and 16C illustrate simulated kinematics results for the change in internal-external rotation (in degrees) of a knee joint as the knee bends or flexes to represent the patient going through the steps of transitioning from a generally standing position, namely a flexion angle of 0 degrees (see FIG. 16A), to a generally kneeling position, namely a flexion angle of 100 degrees (see FIG. 16C).

Figure 17A:
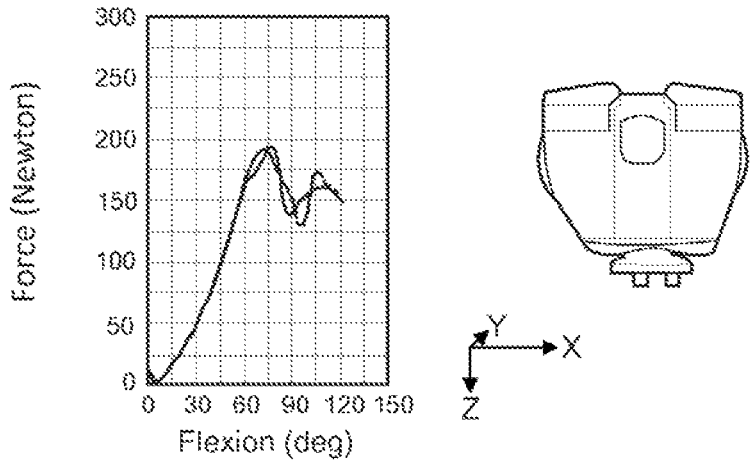
FIGS. 17A, 17B and 17C show graphical representations of predicted computer simulation results for the change in patella lateral shear force (in newtons) of a knee joint of a patient based on alignment information data calculated using a computer-implemented method in accordance with an embodiment of the present invention, shown for a generally standing position, FIG. 17A, a generally kneeling position, FIG. 17C, and an intermediate position, FIG. 17B.
Figure 17B:
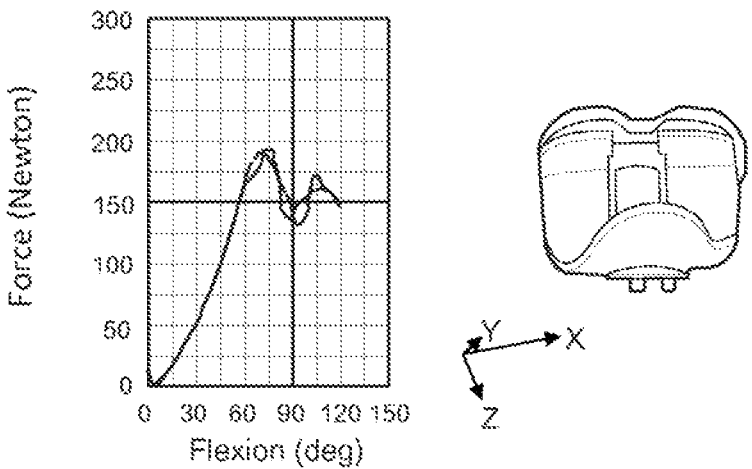
Figure 17C:
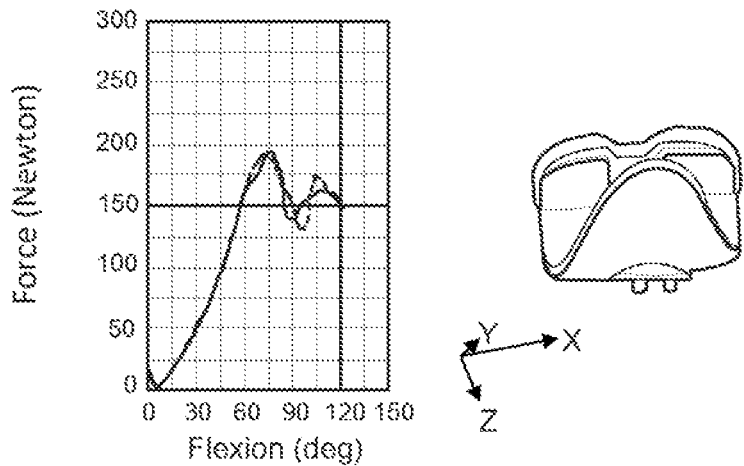

FIGS. 17A, 17B and 17C illustrate simulated kinematics results for the change in patella lateral shear force (in newtons) of a knee joint as the knee bends or flexes to represent the patient going through the steps of transitioning from a generally standing position, namely a flexion angle of 0 degrees (see FIG. 17A), to a generally kneeling position, namely a flexion angle of 120 degrees (see FIG. 17C).

Figure 18A:
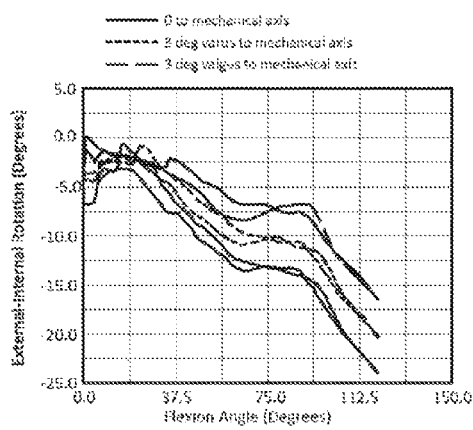
FIGS. 18A, 18B and 18C show graphical representations of predicted computer simulation results for the change in internal-external rotation (in degrees) of a knee joint of a patient at three different varus/valgus angles based on alignment information data calculated using a computer-implemented method in accordance with an embodiment of the present invention, shown for a generally standing position, FIG. 18A, a generally crouching or squatting position, FIG. 18C, and an intermediate position, FIG. 18B.
Figure 18A:
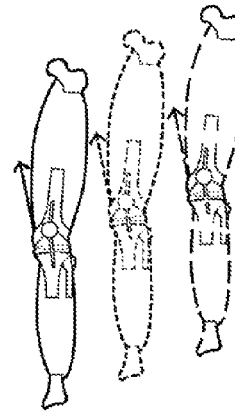
Figure 18B:
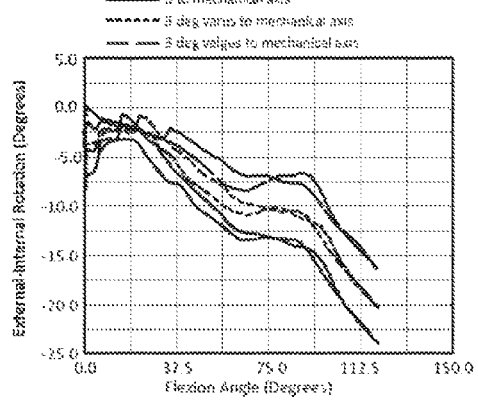
Figure 18B:
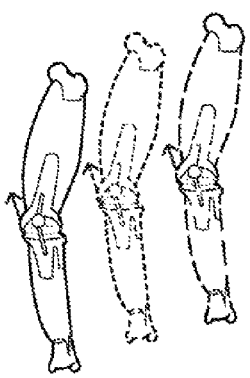
Figure 18C:
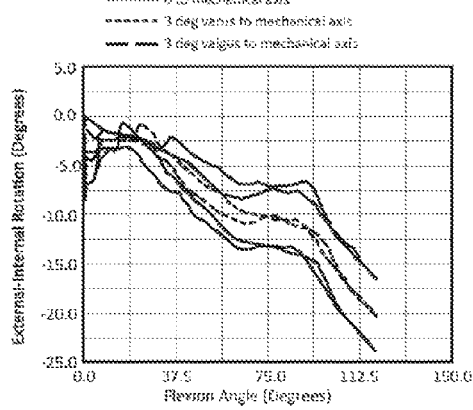
Figure 18C:
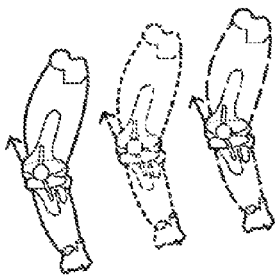

FIGS. 18A, 18B and 18C illustrate simulated kinematics results for the change in internal-external rotation (in degrees) of a knee joint as the knee bends or flexes to represent the patient going through the steps of transitioning from a generally standing position, namely a flexion angle of 0 degrees (see FIG. 18A), to a generally crouching or squatting position, namely a flexion angle of around 112.5 degrees (see FIG. 18C). The results illustrate the degree of variation in the of the internal-external rotation at three different varus/valgus angles relative to the primary mechanical axis of the knee joint.

Figure 19A:
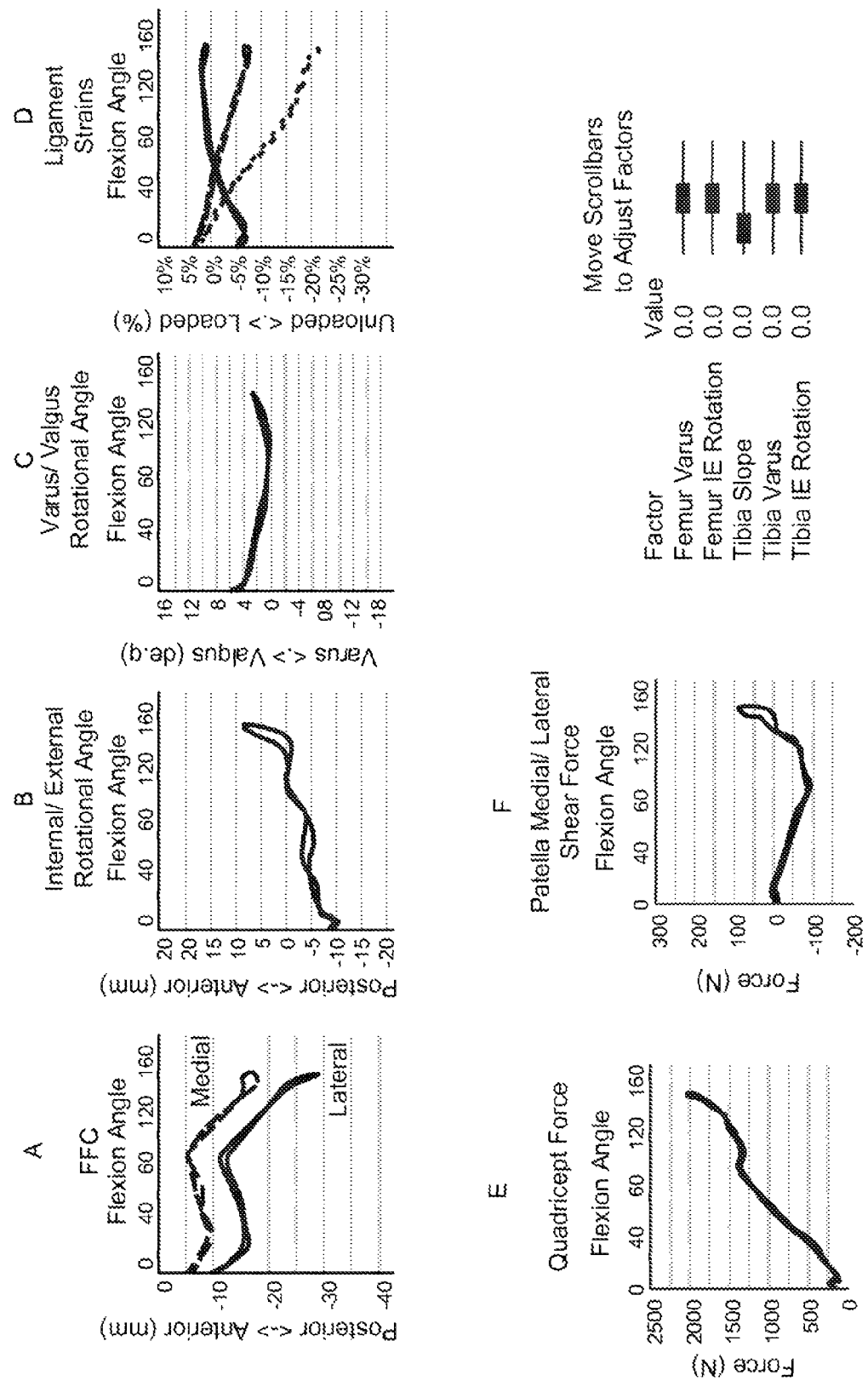
FIGS. 19A and 19B shows graphical representations of predicted computer simulation results for the change in various parameters of a knee joint of a patient based on alignment information data calculated using a computer-implemented method in accordance with an embodiment of the present invention, shown for a generally standing position, FIG. 19A, and a generally kneeling position, FIG. 19B.
Figure 19B:
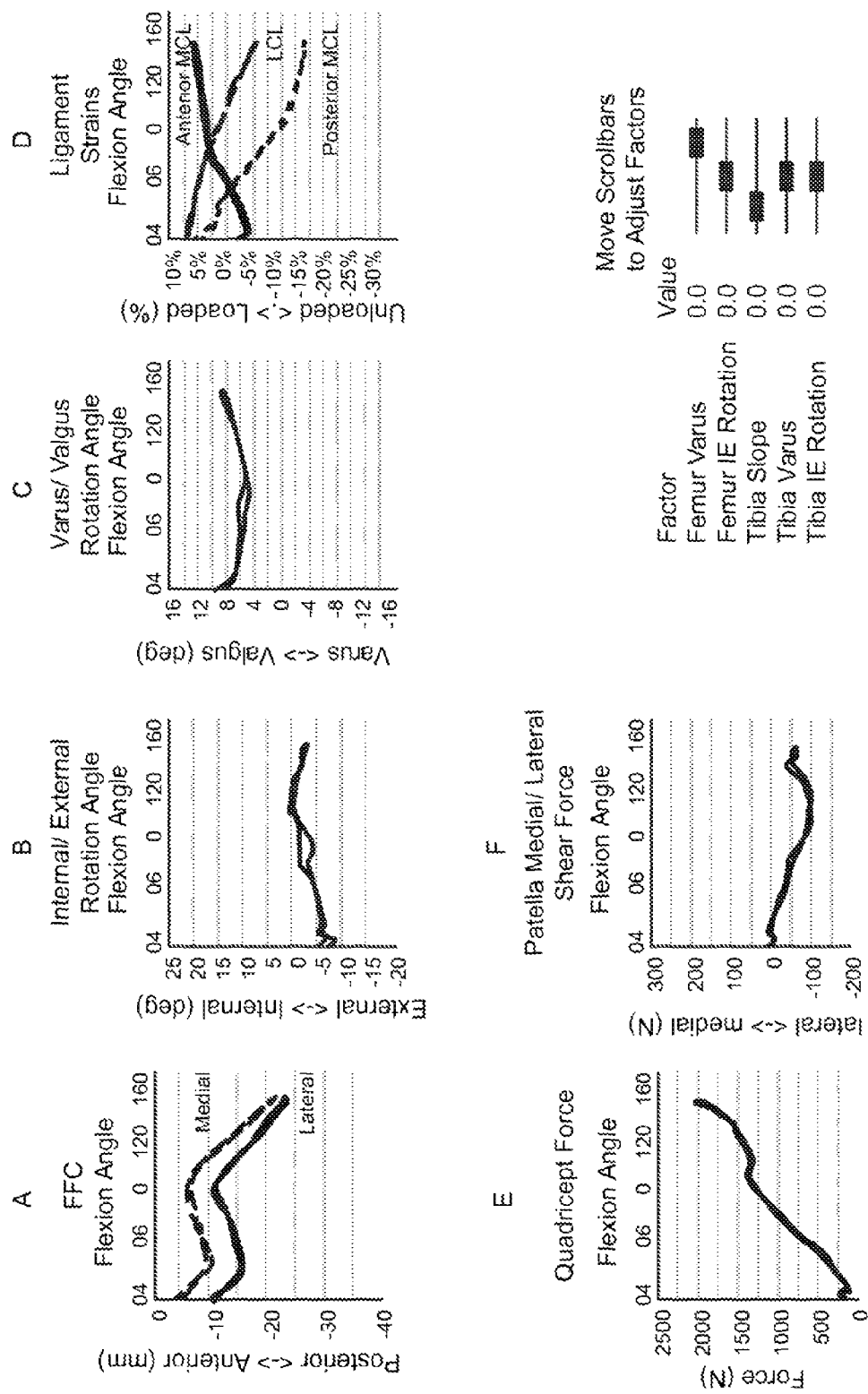

FIGS. 19A and 19B illustrate simulated kinematics results for the change in various parameters of a knee joint as the knee bends or flexes to represent the patient going through the steps of transitioning from a generally standing position, namely a flexion angle of 0 degrees, to a generally kneeling position, namely a flexion angle of around 140 degrees. In this arrangement, an operator, such as a surgeon, has the ability to predict simulated kinematics results for the knee joint of a patient by adjusting the various parameters associated with the knee joint, such as the varus angle (in degrees), the internal-external rotation (in degrees) and slope (in degrees). For example, in FIG. 19A, the varus angle (in degrees), and the internal-external rotation (in degrees) of the femur and tibia are all set to zero, as is the slope of the tibia. However, when the varus angle of the femur is adjusted to 3.0 degrees (see FIG. 19B), there are noticeable differences in the medial (see the flexion facet centre (FFC) results in FIG. 19B image A), the internal-external rotation angle of the knee joint (see FIG. 19B image B), the ligament strain on the lateral collateral ligament (LCL), the anterior medial collateral ligament (anterior MCL) and the posterior medial collateral ligament (posterior MCL) (see FIG. 19B image D), and the patella medial/lateral shear force (in newtons) (see FIG. 19B image E). In this sense, by adjusting the various parameters associated with the knee joint, the surgeon is able to predict the optimum results for aligning an orthopaedic implant relative to the joint of the patient.

Figure 20A:
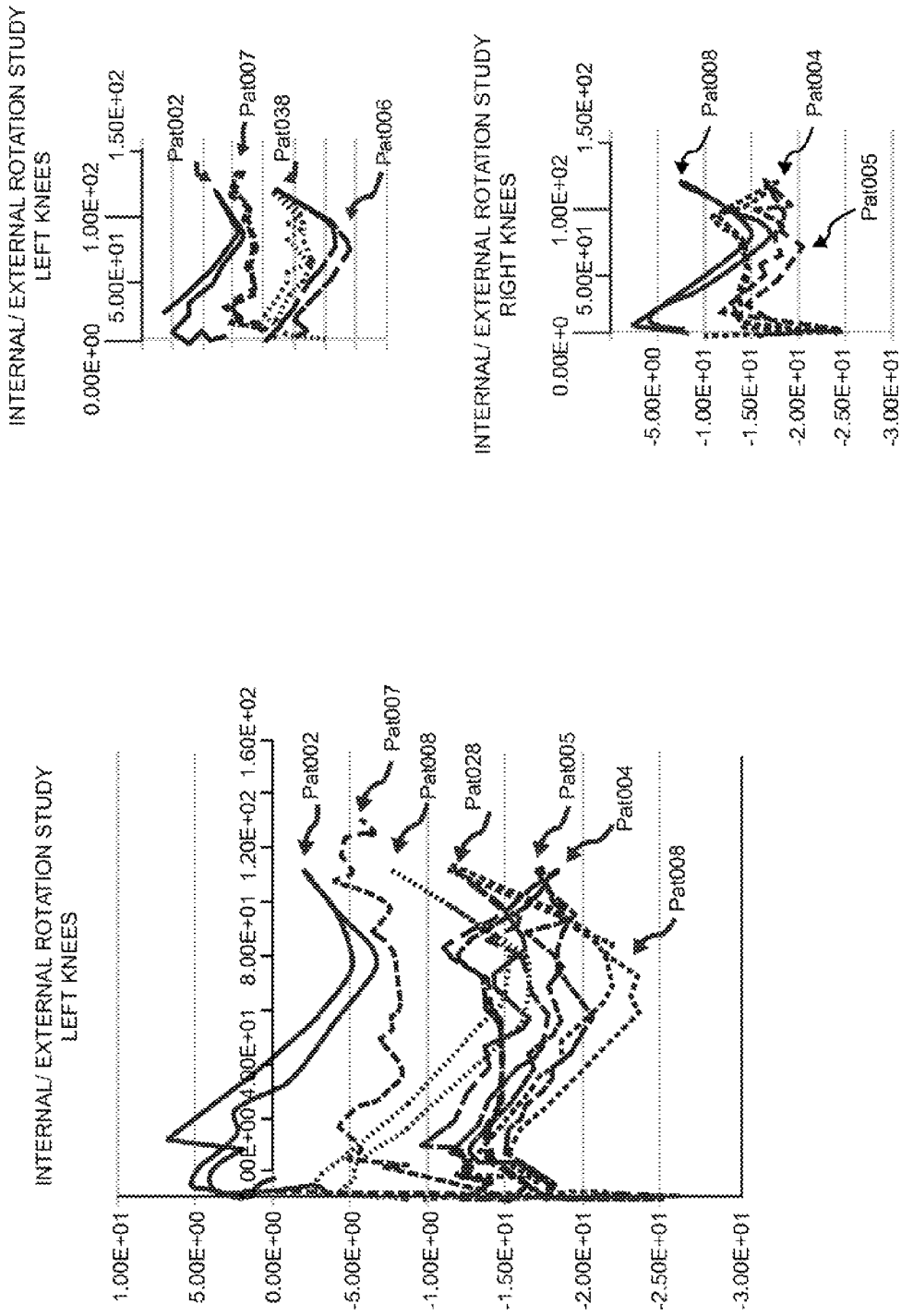

FIG. 20A illustrates a patient survey obtained for a group of eight patients, each fitted with an orthopaedic implant, stored as library alignment information data and library alignment configuration data in the database 1030. The results of the survey show the change in internal-external rotation (in degrees) of their respective left and right knee joints as the knees bend or flex to represent the patients going through the steps of transitioning from a generally standing position to a generally crouching or squatting position. Based on the results of the left knees studied, all exhibit generally the same internal-external rotation with respect to the fitted orthopaedic implant. For the right knees studied, the right knee of one patient (pat004) shows an abnormal internal-external rotation when compared with the others.

FIG. 20B illustrates a corresponding set of results obtained from the same group of eight patients showing the change in patella shear force (in newtons) of the left and right knee joints of the eight patients as their respective knees bend or flex to represent the patients going through the steps of transitioning from a generally standing position to a generally crouching or squatting position. Based on the results of the left knees studied, all but one of the left knees (pat2ERyanLeftTECHSIM) exhibits generally the same patella shear force with respect to the fitted orthopaedic implant. For the right knees studied, the right knee of one patient (pat008) shows an abnormal patella shear force when compared with the others.

Based on the results of FIG. 20A and FIG. 20B, an operator, such as a surgeon, can observe the effects of a particular orthopaedic implant when fitted to each of the eight patients and how it influences the corresponding patients' biomechanical performance. The surgeon can then use these results to predict how the same orthopaedic implant when fitted to the patient will influence their biomechanical performance through a comparison of the alignment information data and alignment configuration of the patient with the corresponding library data stored in the database 1030.

FIGS. 21 to 23 illustrate various graphical representations of predicted computer simulation results for a hip joint of a patient based on the alignment information data calculated using the computer-implemented method 300 described above.

Figure 21A:
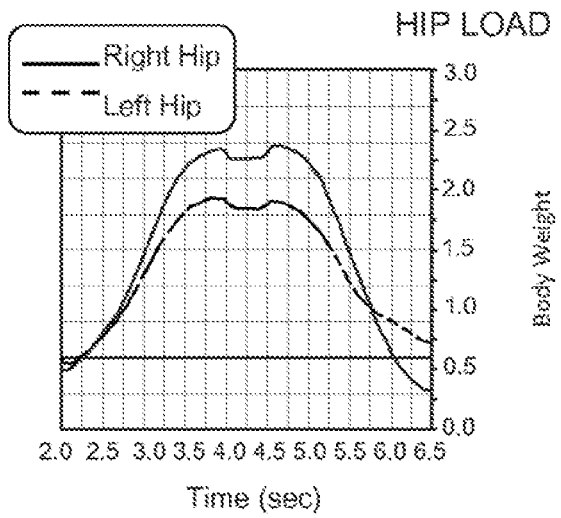
FIGS. 21A, 21B and 21C show graphical representations of predicted computer simulation results for the change in hip load (in newtons) of the left and right hip joints of a patient based on alignment information data calculated using a computer-implemented method in accordance with an embodiment of the present invention, shown for a generally standing position, FIG. 21A, a generally crouching position, FIG. 21B, and then returning to a generally standing position, FIG. 21C.
Figure 21A:
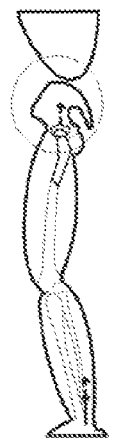
Figure 21B:
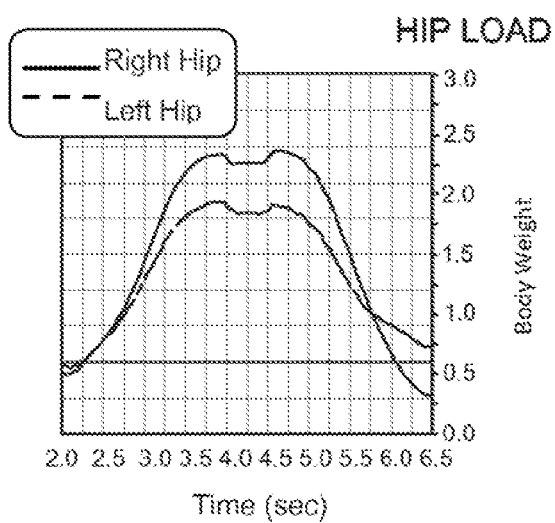
Figure 21B:
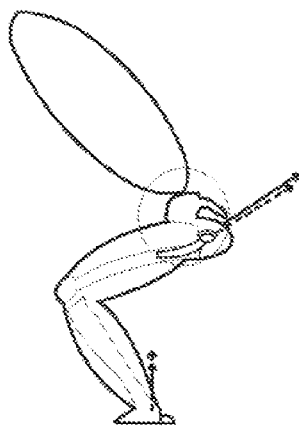
Figure 21C:
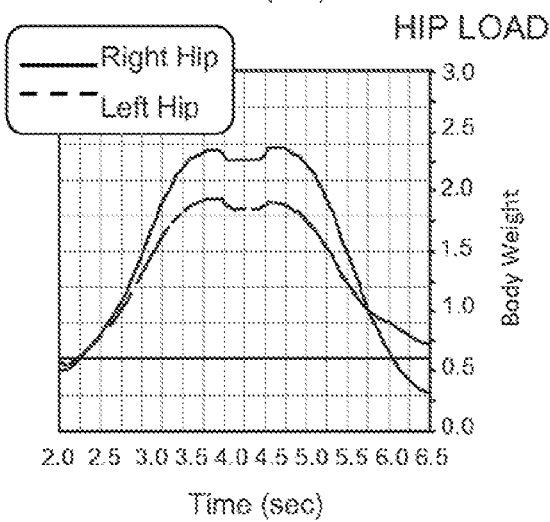
Figure 21C:

FIGS. 21A, 21B and 21C illustrate simulated kinematics results for the change in hip load (magnitude and direction) of the left and right hip joints of a patient as the patient goes through the steps of transitioning from a generally standing position (see FIG. 21A), to a generally crouching position (see FIG. 21B), and back to the generally standing position (see FIG. 21C). In this example, the left hip joint simulated orthopaedic implant comprises the stem of the femur and the corresponding acetabular cup into which the femoral stem is received.

Figure 22A:
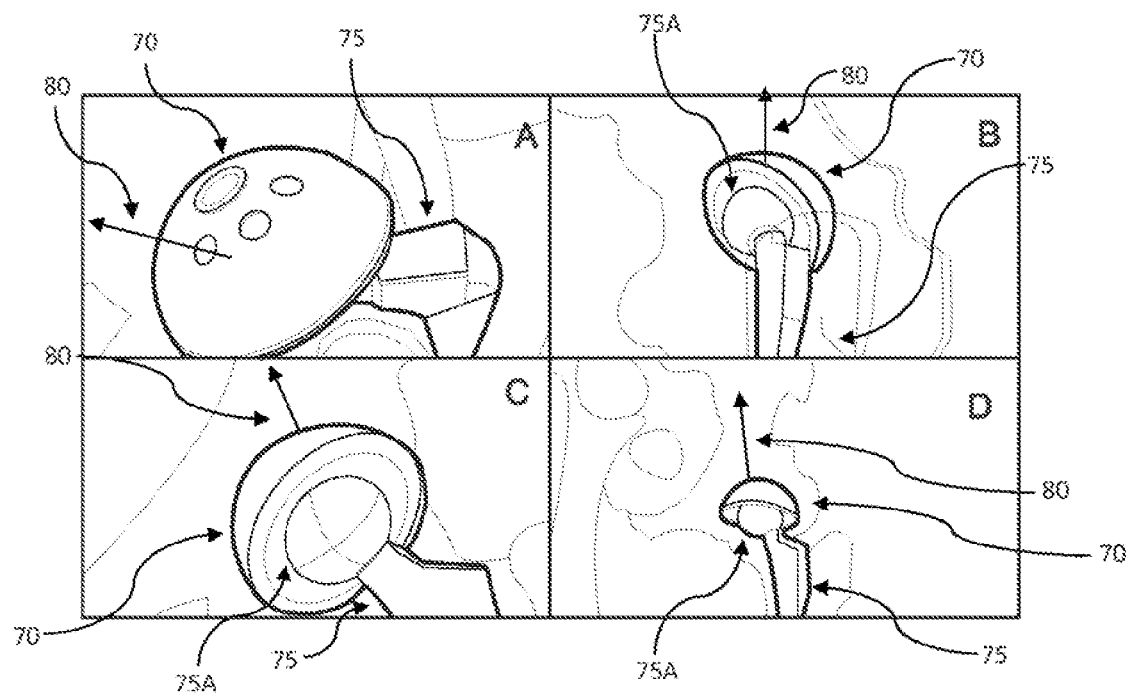
FIGS. 22A, 22B and 22C show graphical representations of predicted computer simulation results for the placement (in degrees) of an acetabular cup of a hip joint of a patient based on alignment information data calculated using a computer-implemented method in accordance with an embodiment of the present invention, shown for a generally standing position, FIG. 22A, and a generally sitting position, FIG. 22B, with FIG. 22C showing a corresponding 2D plot that is representative of the interior articulation surface of the acetabular cup.
Figure 22B:
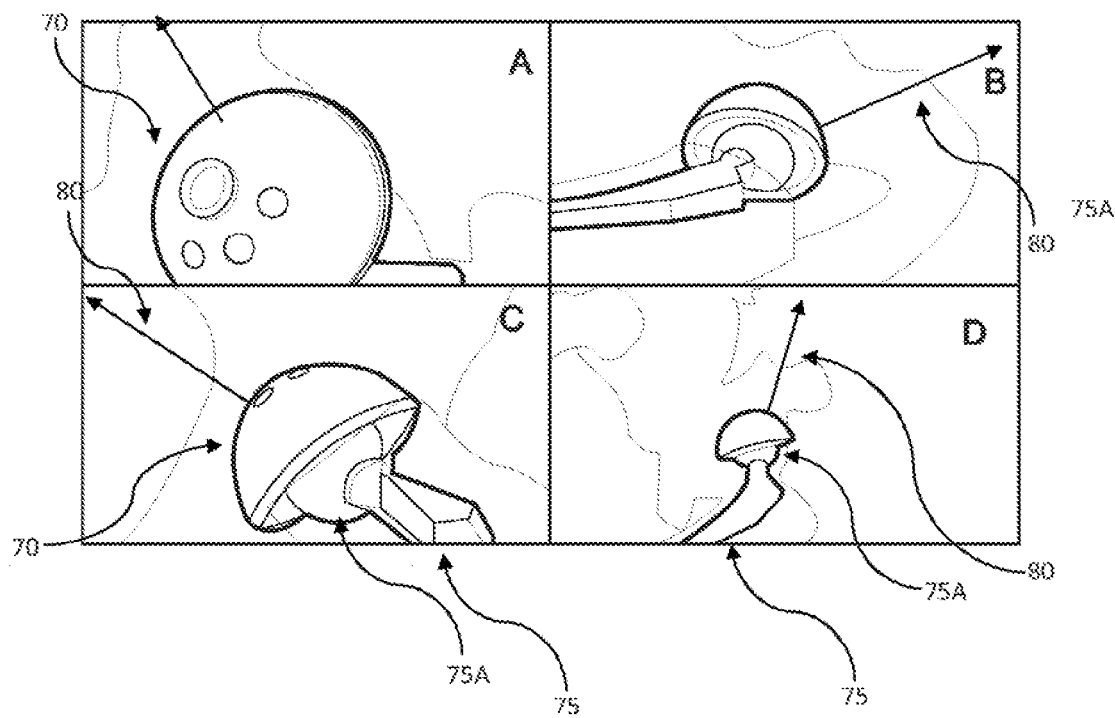
Figure 22C:
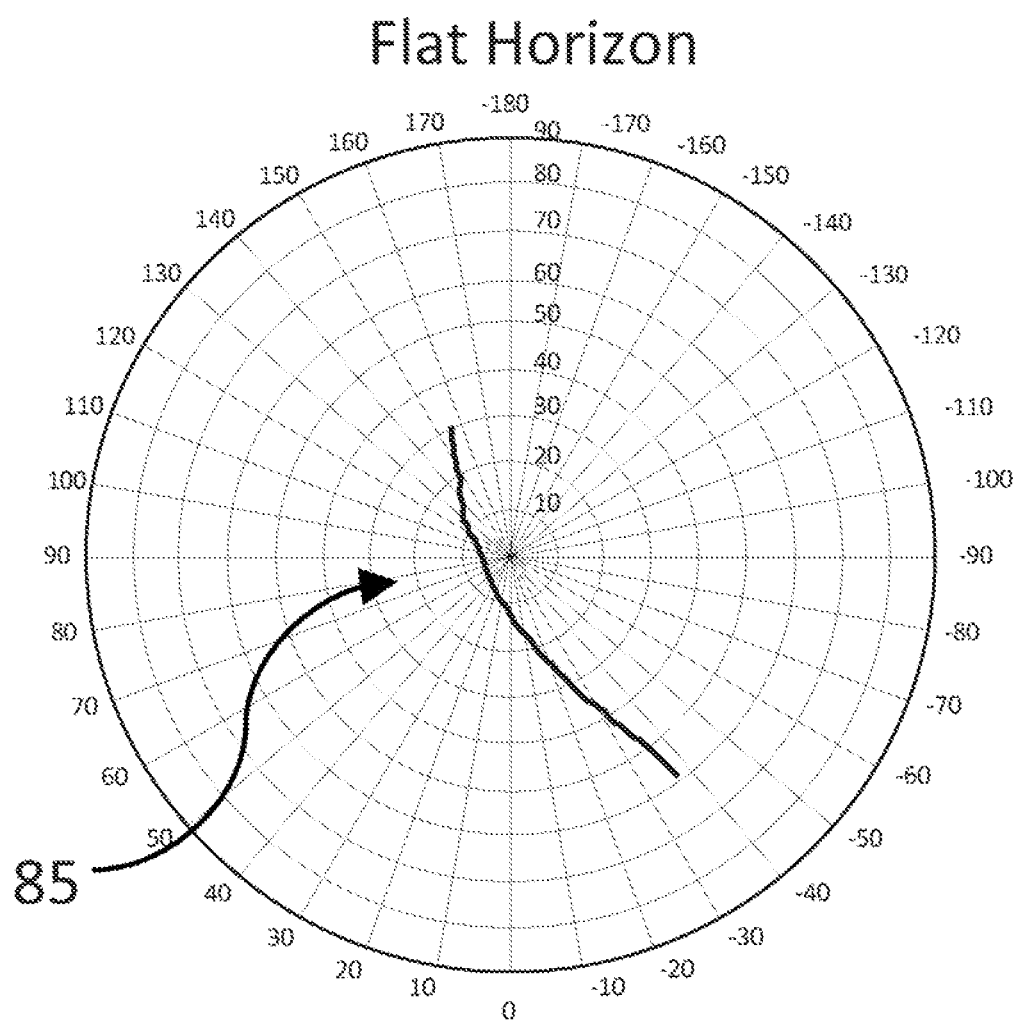

FIGS. 22A, 22B and 22C illustrate simulated kinematics results for the placement (in degrees) of a simulated orthopaedic implant in the form of an acetabular cup 70 and a femur 75 with a femoral stem 75, in which the acetabular cup 70 of the hip joint has an angle of inclination of 45 degrees and 25 degrees anteversion with reference to the anterior pelvic plane. The direction of the hip load is indicated by arrow 80 in each of the four images (A, B, C and D) in both FIGS. 22A and 22B.

FIG. 22A corresponds to the patient fitted with the simulated orthopaedic implant in a generally standing position, and FIG. 22B corresponds to the patient in a generally sitting position. The four images (A, B, C, D) in each of FIGS. 22A and 22B correspond to different views of the same hip joint as the patient transitions between the standing and sitting position.

FIG. 22C shows a corresponding 2D plot that is representative of the interior articulation surface of the cup 70, and of the resultant hip load 80, which is shown as a trace line 85 that is produced by the femoral stem 75A acting on the articulation surface of the cup 70 as the patient goes through the steps of transitioning from a generally standing position (see FIG. 22A) to a generally sitting position (see FIG. 22B). The trace line 85 corresponds to the hip load (including the magnitude and direction of the hip load). The centre of the 2D plot corresponds to the polar region of the articulation surface of the cup 70, while the outer periphery of the 2D plot corresponds to the edge of the articulation surface of the cup 70.

Figure 23A:
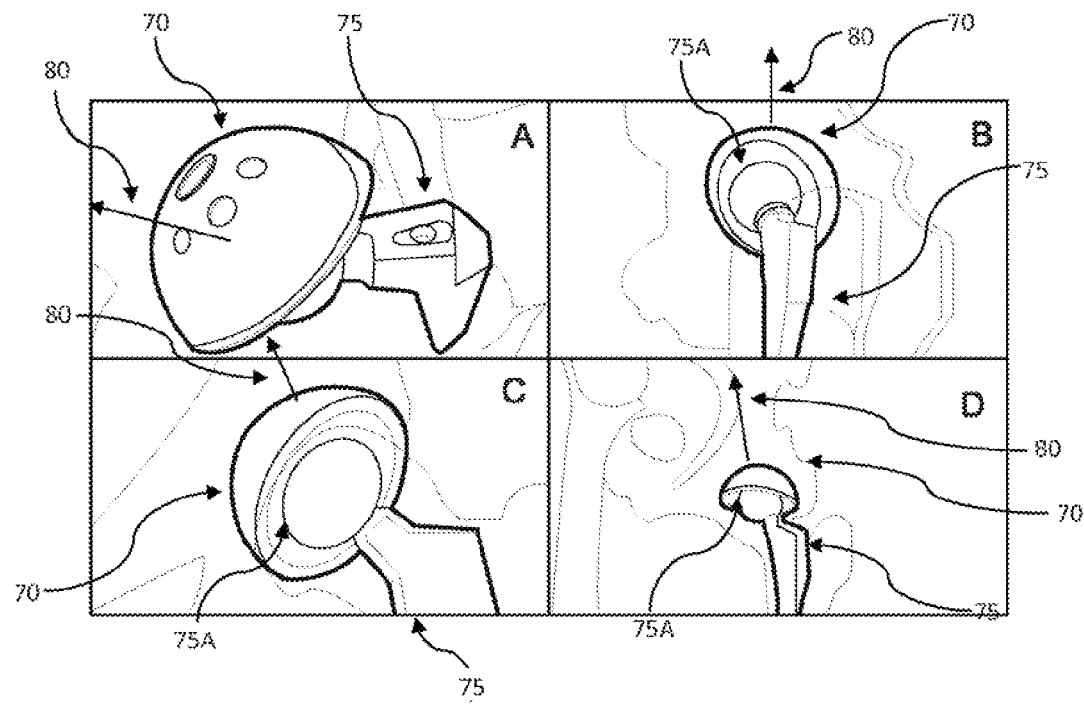
FIGS. 23A, 23B and 23C show graphical representations of predicted computer simulation results for the placement (in degrees) of an acetabular cup of a hip joint of a patient based on alignment information data calculated using a computer-implemented method in accordance with an embodiment of the present invention, shown for a generally standing position, FIG. 23A, and a generally sitting position, FIG. 23B, with FIG. 23C showing a corresponding 2D plot that is representative of the interior articulation surface of the acetabular cup.
Figure 23B:
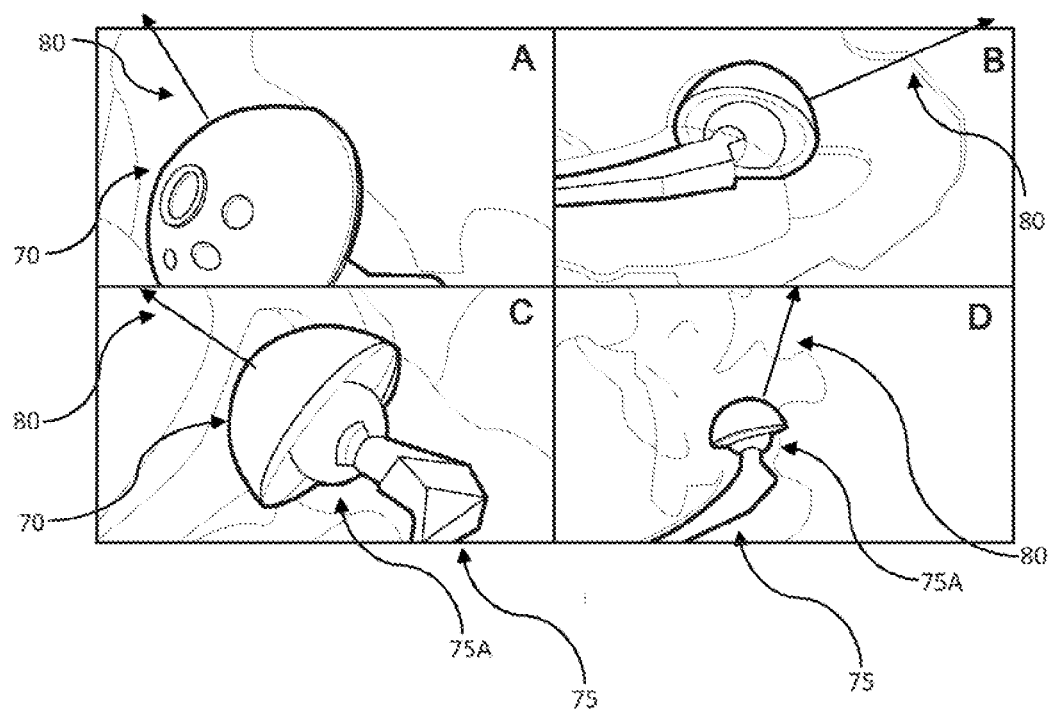
Figure 23C:
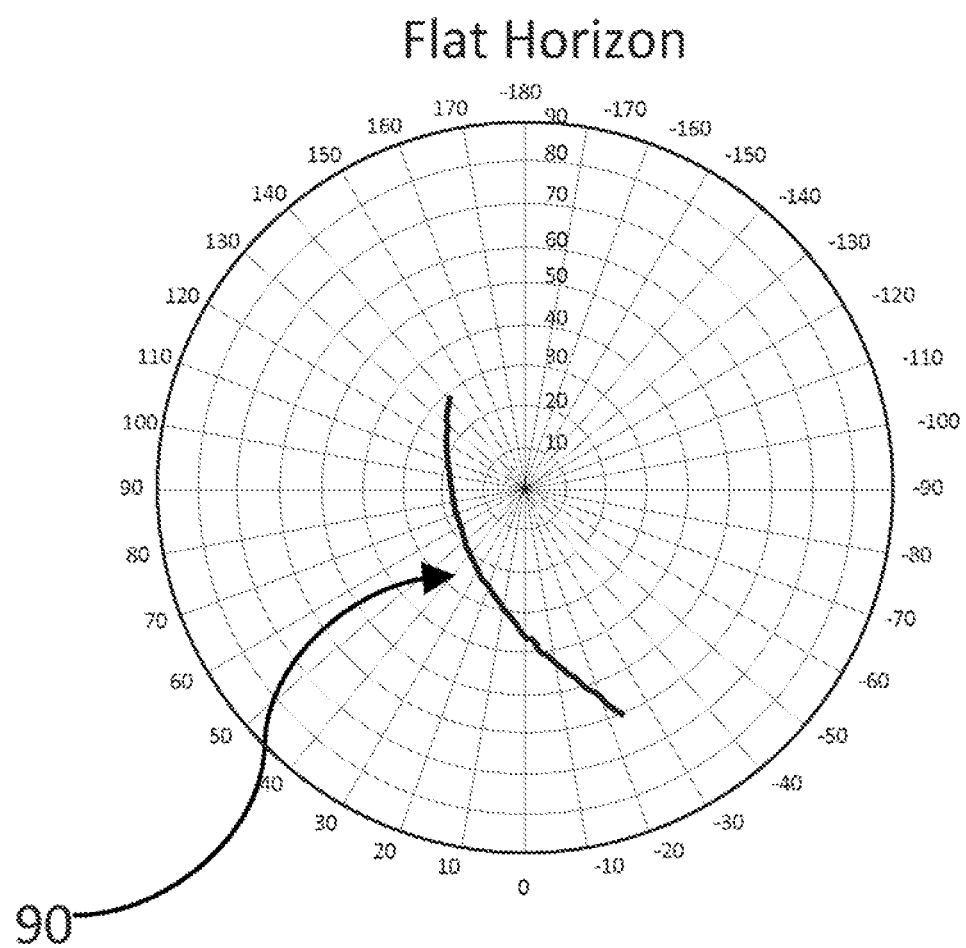

FIGS. 23A, 23B and 23C illustrate simulated kinematics results for the placement (in degrees) of a simulated orthopaedic implant in the form of an acetabular cup 70 and a femur 75 with a femoral stem 75, in which the acetabular cup 70 of the hip joint has an angle of inclination of −35 degrees and 15 degrees anteversion (see FIG. 23A) with reference to the anterior pelvic plane. The direction of the hip load is indicated by arrow 80 in each of the four images (A, B, C and D) in both FIGS. 23A and 23B.

FIG. 23C shows a corresponding 2D plot that is representative of the interior articulation surface of the cup 70, and of the resultant hip load 80, which is shown as a trace line 90 that is produced by the femoral stem 75A acting on the articulation surface of the cup 70 as the patient goes through the steps of transitioning from a generally standing position (see FIG. 23A) to a generally sitting position (see FIG. 23B). The trace line 90 corresponds to the hip load (including the magnitude and direction of the hip load). The centre of the 2D plot corresponds to the polar region of the articulation surface of the cup 70, while the outer periphery of the 2D plot corresponds to the edge of the articulation surface of the cup 70.

The simulated results of FIG. 22C and FIG. 23C show that the trace line 85 in FIG. 22C is generally closer to the centre of the 2D plot (the polar region of the articulation surface) than trace line 90 (see FIG. 23C). In addition, the trace line 90 also extends slightly further towards the outer periphery of the 2D plot than the trace line 85.

It will be appreciated that the simulated kinematics results of FIGS. 14 to 23 are not limited to those shown, but may include other dynamic metrics.

Implant Design Data

Figure 11:
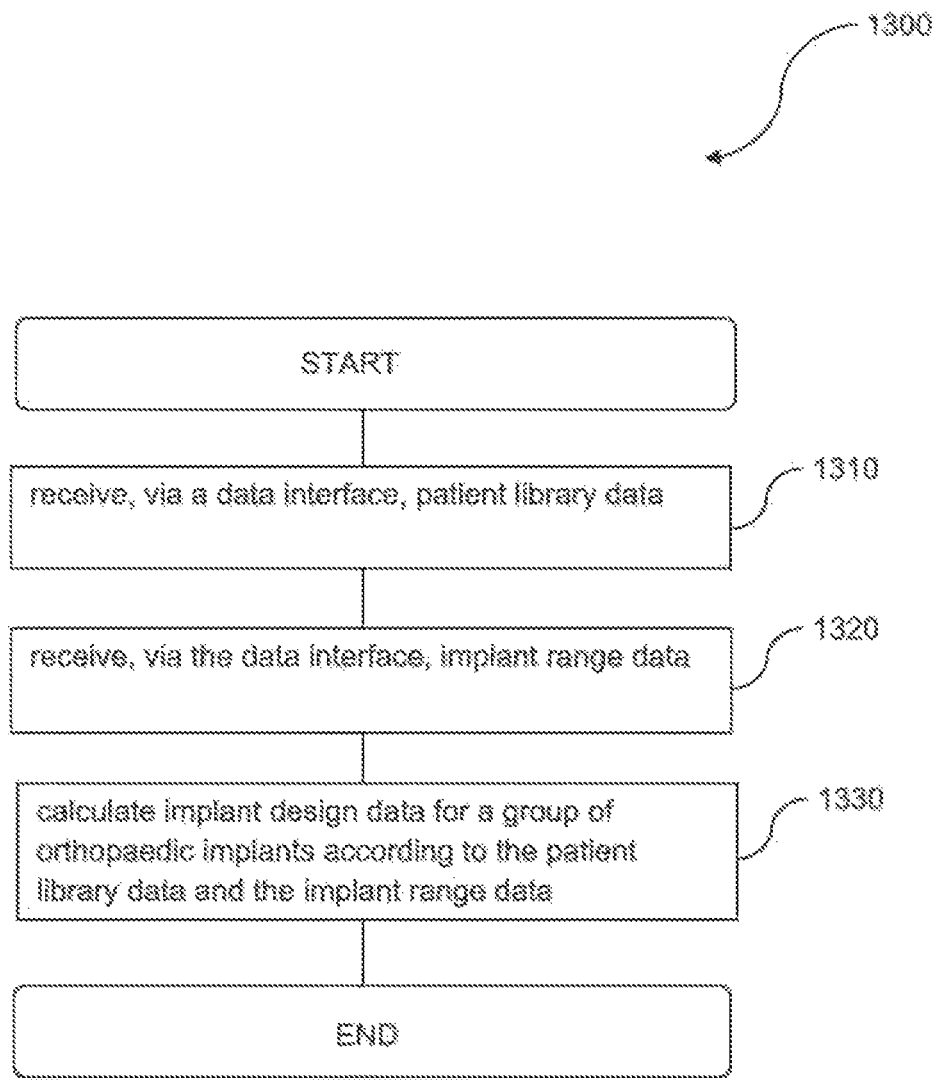
FIG. 11 shows a computer-implemented method in accordance with an embodiment of the present invention.

FIG. 11 shows a computer-implemented method 1300 for calculating implant design data for a group of orthopaedic implants in accordance with another embodiment of the present invention. The computer-implemented method 1300 starts at step 1310 where the processor 1000 is controlled by the computer program code to receive, via the data interface (180, 140), patient library data, corresponding to the alignment information data of multiple orthopaedic implants of multiple patients provided by the computer-implemented method 300 described above. At step 1320, the processor 1000 is further controlled by the computer program code to receive, via the data interface (180, 140), implant range data, indicative of one or more subsets of the patient library data selected according to a user input request. At step 1330, the processor 1000 is further controlled by the computer program code to calculate the implant design data for the group of orthopaedic implants according to the patient library data and the implant range data. Revised patient library data is calculated on the basis of filtering the patient library data according to the implant range data. The implant design data for the group or orthopaedic implants can then be calculated according to a statistical analysis of the revised patient library data using an appropriate statistical analysis method. A number of statistical analysis methods are available for such purpose including, but not limited to, such methods as regression analysis and least squares analysis.

In one embodiment, the operator can choose to filter the patient library data further according to patient satisfaction data relating to a number of satisfied patients selected from a group of patients fitted with an orthopaedic implant for performing certain post-implant activities. The patient satisfaction data may relate to the overall performance of the particular orthopaedic implant with respect to its biomechanical performance when performing the post-implant activity or activities, the degree of comfort experienced by the patient when performing that particular post-implant activity, and the degree of freedom of motion when performing that particular post-implant activity. Therefore, if a number of patients were satisfied with a particular orthopaedic implant and its biomechanical performance then this result can be indicated graphically on a chart, to alert the operator to the potential that this orthopaedic implant has in relation to a patient looking to receive the orthopaedic implant.

In one embodiment, the operator can choose to filter the patient library data according to the number of orthopaedic implants selected from a group of orthopaedic implants for performing at least one of the one or more post-implant activities of the patient.

In one embodiment, the operator can choose to filter the patient library data according to the number of orthopaedic implants of a particular size that are available to the patient to enable them to perform at least one of the one or more post-implant activities.

Figures 24A, 24B:
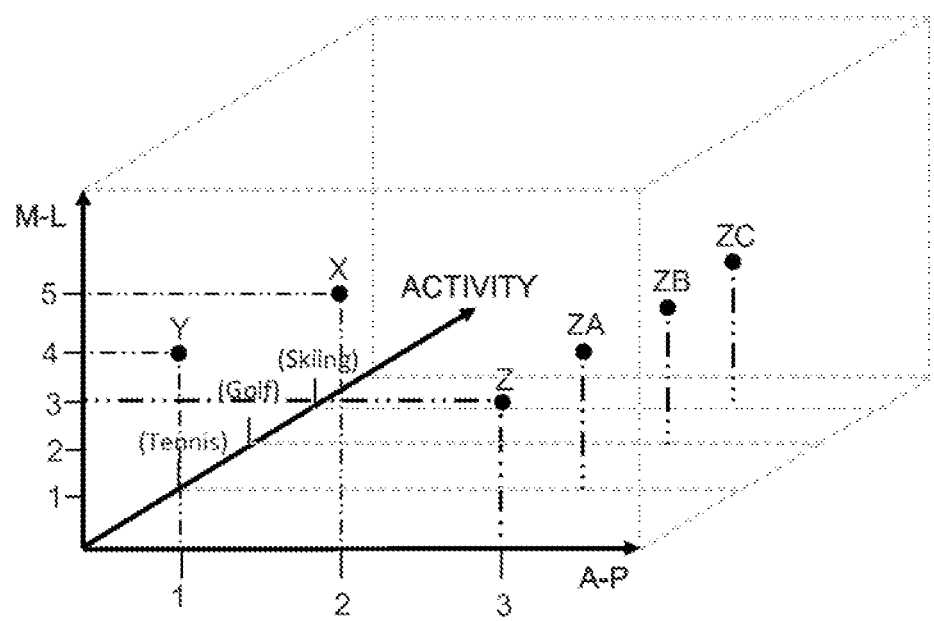
FIG. 24A shows a plot for calculating implant design data for a group of orthopaedic implants in accordance with an embodiment of the present invention, FIG. 24B showing a legend for the plot of FIG. 24A.

FIG. 24 illustrates an exemplar graphical representation that an operator, such as a surgeon, can use to identify an orthopaedic implant that is the most appropriate fit for the joint of a patient that will enable the patient to perform one or more of the desired post-implant activities. Firstly, the size of the patient's joint is determined based on the anterior-posterior (A-P) and median-lateral (M-L) dimensions of the joint. The dimensions of the joint are then plotted against a range of orthopaedic implants (for example, X, Y and Z), obtained from the corresponding library data stored in the database 1030, to identify the most appropriately sized orthopaedic implant for the patient. In this example, and as shown in FIG. 24A, the A-P and M-L dimensions of the joint are sizes 3 and 3, respectively, such that the most appropriately sized orthopaedic implant is Z. Orthopaedic implants Z, ZA, ZB, and ZC all have the same A-P and M-L dimensions as the joint, but their articulation surfaces differ by varying degrees. For example, the depth of the trochlear for orthopaedic implant Z may be greater than that for orthopaedic implants ZA, ZB, and ZC to provide stability to the joint once implanted.

As shown in FIG. 24A, the selected orthopaedic implants (Z, ZA, ZB, and ZC) correspond to an associated post-implant activity (for example, tennis, golf, skiing, or any defined kinematic propositions) by virtue of the difference in the associated articulation surface. For example, orthopaedic implant ZA comprises an articulation surface that is translation limiting, making it suitable for such activities as tennis, while orthopaedic implant ZB has an articulation surface that is rotation accommodating, thereby making it suitable for such activities as golf. Assuming the patient has a greater desire to play tennis over the other two post-implant activities (golf and skiing), the surgeon would opt for orthopaedic implant ZA, as indicated in FIG. 24B.

Figure 25:
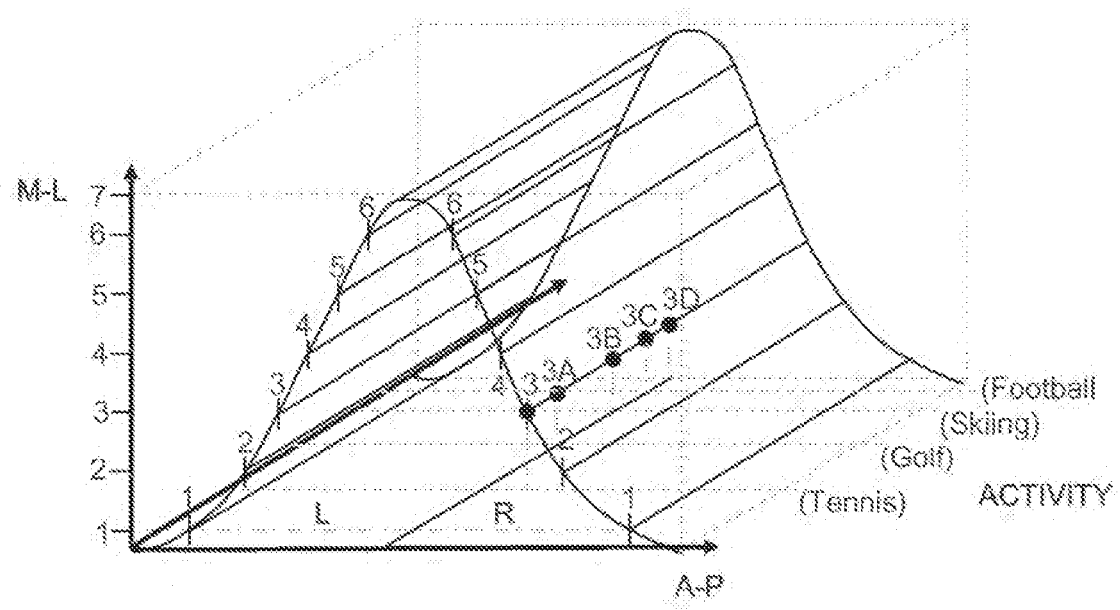
FIG. 25 shows a plot for calculating implant design data for a group of orthopaedic implants in accordance with an embodiment of the present invention.

FIG. 25 illustrates another exemplar graphical representation that an operator, such as a surgeon, can use to identify a range of orthopaedic implants for both left and right knee joints, stored within the database 1030 as patient library data, which fall within a certain size range. Firstly, the desired size range of left and right orthopaedic implants are input as implant range data according to both the anterior-posterior (A-P) and median-lateral (M-L) dimensions of each orthopaedic implant. In this example, the size range selected includes sizes from 1 to 6 for both left (L) and right (R) orthopaedic implants, respectively. The corresponding plot provides a bell curve as shown in FIG. 25.

As indicated in the plot, post-implant activities (tennis, golf, skiing, football, or any defined kinematic propositions) are also taken into consideration when generating such results, producing a 3D bell curve. In this example, and as shown in FIG. 25, the A-P and M-L dimensions of the right (R) orthopaedic implant of size 3, are the same as the A-P and M-L dimensions for the corresponding right (R) orthopaedic implants 3A, 3B, 3C, 3D, but the articulation surfaces of each implant differs, as described in the example above (see FIG. 24), where 3A has an articulation surface that is suitable for playing tennis, 3B for golf, 3C for skiing, and 3D for football.

By being able to identify orthopaedic implants of a particular size range, it is possible for a customer to create, for example, an inventory of orthopaedic implants to suit one or more sectors of the general public.

It will be appreciated that the patient library data and implant range data are not limited to those described above, but that a range of patient data or orthopaedic implant data may be stored in the database 1030 for future reference.

Advantages

The various embodiments described above provide a range of advantages including:

Providing improved patient specific alignment by considering a range of possible alignment configurations before the implant operation. Once an improved patient specific alignment has been identified, a surgeon can choose a modern and precise computer assisted surgical technique, such as a customized cutting guide or surgical navigation, to deliver this alignment with the required precision.

Providing improved patient specific alignment by considering a nominal alignment configuration, determined by the operator as being an alignment configuration that would be suitable for the patient to perform one or more of their desired post-implant activities.

Providing patient specific improvement of the choice of orthopaedic implant available. A person skilled in the art would be aware that there are a number of predetermined orthopaedic implants commercially available with each implant having slight differences. The alignment information data and alignment configuration data calculated according to the embodiments described above can be presented in various forms, such as, for example, graphical representations, to enable a surgeon to select the most appropriate orthopaedic implant with respect to the patient's joint and their desired post-implant activities.

Enabling the specification of a specific articulator insert (for example a tibial insert for a knee) comprising a customized implant with an articulation surface having a shape derived from the patient specific improvement, and the alignment/placement of that patient specific articulator insert relative to the knee joint.

The provision of the simulated results in the form of, for example, one or more data files, enables the manufacture of a physical product:

Custom patient specific jig, namely a cutting guide that can be placed on the joint of a patient during the operation to physically guide the surgeon.

Custom made computer navigation file, essentially an interactive demonstration specific to the implant operation with respect to the positioning and placement of an orthopaedic implant relative to the joint of a patient.

Custom made robotics file that can be used by an alignment system to align an orthopaedic implant relative to the joint of a patient.

Customized implant with an articulation surface having a shape derived from the patient specific improvement process. The custom articulation can then be attached, adhered, or mechanically locked to the implant of an articulator insert (such as a tibial tray for a tibial insert).

Complete custom made orthopaedic implants with patient specific custom articulation surface.

Use

A step by step general example of a preferred embodiment of the present invention is set out below which provides a virtual kinematic simulator:

A 3D image of the bone geometry of a knee joint in the form of a CT or MRI image is acquired by usual means and converted to a DICOM file by an operator.

The DICOM file is communicated to the computing device 100 using, for example, a client computing device 220 connected to the computing device 100 via the Internet 230 or a private WAN.

The DICOM file is filtered and segmented to remove unwanted data.

Anatomical landmarks are identified from the DICOM file.

Surgery is planned for a generic default position, such as mechanical axis alignment for the knee, and a chosen implant design. This specifically involves aligning the implants such that the default position would be achieved if no improvement occurred.

A deterministic patient specific rigid body mechanics simulation is performed by the computing device 100, A deterministic model is developed when a simulation is performed on a specific implant position to produce a simulated result.

The operator can view the simulation result of the default position with chosen orthopaedic implants in the form of, for example, a graphical representation, by using a client computing device 220 connected to the computing device 100 via the Internet 230.

The operator can then modify the position from the previous default and/or modify the chosen orthopaedic implant and view new simulation results. The factors that influence the modification are those understood by the operator, based on the operator's skills and experience. These could be patient specific or more general, for example, it could relate to a specific patient requirement for more external rotation of the femoral component, or it could be more simply a recognition that in all the extension is achieved by increasing the distal femoral resection.

Once the operator, such as a surgeon, is satisfied with the simulation, the surgeon can then order a patient specific surgical delivery plan using a client computing device 220 connected to the computing device 100 via the Internet 230.

A surgical plan delivery tool is generated: this includes an actual patient specific jig, namely, a cutting guide that would be pinned to the bone and used to cut through, and also provide visual navigation instructions that the surgeon can follow.

A step by step general example of a preferred embodiment of the present invention is set out below, which looks at a goal driven improvement that provides the simulation result in the form of, for example, a graphical representation, which includes implant design, position and articulation:

A 3D image of a knee joint in the form of a CT or MRI image is acquired by usual means and converted to a DICOM file by a surgeon.

The DICOM file is communicated to the computing device 100 using, for example, a client computing device 220 connected to the computing device 100 via the Internet 230 or a private WAN.

The DICOM file is filtered and segmented to remove unwanted data.

Anatomical landmarks are identified from the DICOM file.

Damage on the articular surfaces is identified and corrected by interpolation of shape from non damaged articular surfaces to generate a virtual corrected natural model.

A deterministic patient specific rigid body mechanics simulation is performed by the computing device 100, specifically processor 1000.

The design, shape and articulation of the orthopaedic implants could be:

A. an existing design.

B. a combination of existing design and custom made components

C. a completely custom made orthopaedic implant.

The operator, such as a surgeon and/or implant manufacturer, can define an acceptable range of implant positions within six degrees of freedom, for example (whilst maintaining distal femoral and posterior condylar offset, distal femoral cut—three degrees valgus to three degrees varus, distal femoral cut—zero to five degrees flexion, rotation—three degrees internal to three degrees external in regards to the trans-epicondylar axis).

Using, for example, a client computing device 220 connected to the computing device 100 via the Internet 230 or a private WAN, the surgeon can view the simulation result of a default position with chosen orthopaedic implants in the form of, for example, a graphical representation.

The surgeon can then modify the position from the previous default and/or modify the chosen implant and view new simulation results. The factors that influence the modification are those understood by the surgeon, based on the surgeon's skills and experience. These could be patient specific or more general, for example, it could relate to a specific patient requirement for more external rotation of the femoral component, or it could be more simply recognition that in all, the extension is achieved by increasing the distal femoral resection.

Once the surgeon is satisfied with the simulation, the surgeon can then order a patient specific surgical delivery plan using, for example, a client computing device 220 connected to the computing device 100 via the Internet 230 or a private WAN.

A surgical plan delivery tool is generated: this includes an actual patient specific jig that would be pinned to the bone and used to cut through, and also provide visual navigation instructions that the surgeon can follow.

A step by step general example of a preferred embodiment of the present invention is set out below, which looks at a multi objective goal-driven improvement directed towards patient specific functionality goals:

Patient functionality objectives, namely, desired post-implant activities, and the patient's preference for the post-implant activities are captured in lay language by the questionnaire.

Functionality goals are then ranked in a hierarchy by the patient according to their preference for performing the post-implant activities, and by the surgeon: for example (the ability to kneel is most important, the ability to walk up stairs is second most important, the ability to play lawn bowls is third most important, and so on).

A 3D image of the knee joint of the patient in the form of, for example, a CT or MRI image, is acquired by usual means and converted to a DICOM file by an operator.

The DICOM file is communicated to the computing device 100 using, for example, a client computing device 220, via the Internet 230 or a private WAN.

The DICOM file is filtered and segmented to remove unwanted data.

Anatomical landmarks are identified from the DICOM file.

A deterministic patient specific rigid body mechanics simulation is performed by the computing device 100, specifically processor 1000, and an appropriate orthopaedic implant is chosen by the operator. The design, shape and articulation of the orthopaedic implant could be:

A. an existing design.

B. a combination of existing design and custom made components.

C. a completely custom made orthopaedic implant.

A multi objective goal-driven improvement is performed as follows:

i. Surgeon and/or implant manufacturer define an acceptable range of implant positions within six degrees of freedom for all parameters: for example (whilst maintaining distal femoral and posterior condylar offset, distal femoral cut—three degrees valgus to three degrees varus, distal femoral cut—zero to five degrees flexion, rotation—three degrees internal to three degrees external in regards to the trans-epicondylar axis).

ii. Patient functionality objectives, namely, desired post-implant activities, and the patient's preference for the activities are transposed by the computing device 100 into numerical goals: for example ("I want to be able to play tennis" becomes "maximum possible external rotation of the femur, relative to the tibia, in extension is required").

iii. Patient specific numerical goals that exist outside the parameters created by the surgeon and manufacturer are excluded.

iv. Patient specific numerical goals that exist inside the parameters created by the surgeon and manufacturer are included.

An improved position is generated, based on the simulation result, which best satisfies the multiples of objectives.

The surgeon can then view the simulation result of the default position with chosen orthopaedic implants in the form of, for example, a graphical representation, using a client computing device 220 connected to the computing device 100 via the Internet 230 or private WAN.

The surgeon can then modify the position from the previous default and/or modify the chosen orthopaedic implant and view new simulation results. The factors that influence the modification are those understood by the surgeon, based on the surgeon's skills and experience. These could be patient specific or more general.

Once the surgeon is satisfied with the simulation, the surgeon can then order a patient specific surgical delivery plan using, for example, a client computing device 220 connected to the computing device 100 via the Internet 230 or private WAN.

A surgical plan delivery tool is generated: this includes an actual patient specific jig that would be pinned to the bone and used to cut through, and also provide visual navigation instructions that the surgeon can follow.

It is emphasized that ideal simulation models correspond to a variety of different post-implant activities and actions ranging from simple everyday movements such as climbing up and down a staircase and getting into and out of a car, to more rigorous activities such as playing netball and skiing.

It will be appreciated by those skilled in the art that the patient specific alignment will provide patients with significantly improved functional outcomes. This is generally done by the computer-implemented methods described above which:

Pre-operatively create accurate patient specific models of individual patients.

Improves the alignment for each patient to meet their individual functional requirements.

Dynamic modelling techniques have been shown to be a valuable tool for the virtual prediction of joint kinematics, loading and articulation behaviour. When applied to joint replacements, dynamic modelling has been used to distinguish the generalised effects that design variations have on joint kinematics, joint loading and joint articulation behaviour before needing to test these designs on patients. This is valuable when comparing the general features and benefits of different designs.

The simulation of patient specific scenarios by inputting patient specific parameters, rather than generalised 'average' parameters, gives rise to predictions that are relevant to a specific patient in a specific "real life" scenario.

This is especially advantageous as applications are made for the surgical delivery plan to be accessed directly from a surgical theatre using, for example, a client computing device 220 connected to the computing device 100 via the Internet 230 or a private WAN.

Other advantages of the invention include:

Providing a full biomechanical simulation using inverse dynamics with rigid body mechanics simulations to predict a post operative range of motion, joint kinematics, joint loading, joint behaviour, friction, and functionality results in a certain situation. For example: if a certain orthopaedic implant X is placed in a particular patient Y in specific orientation Z, the result can be accurately predicted. Further, all desirable ranges of positions and shapes can be tested/sampled.

Providing prediction of patient specific natural kinematics by using an inverse dynamics with rigid body mechanics simulation to predict the non pathologic natural range of motion, kinematics, loading, friction and functionality results. Setting this as the goal of the surgery and then using a goal driven improvement to achieve the closest possible representation via selection of implant design, shape, size, articulation and position.

Satisfying patient specific functional goals, namely post-implant activities, by translating the patient lay language from the questionnaire into numerical goals for a multi objective improvement using an inverse dynamics with rigid body mechanics simulation. Achieving the improved position in the closest manner possible via selection of implant design, shape, size, articulation and position.

Providing a surgeon access to the simulation environment and providing the opportunity to pre-operatively and specifically vary the parameters and boundaries and observe the resultant impact to the patient.

It is emphasized that, although the examples and embodiments given above are directed towards knee replacements, the same general technology can be applied to hip replacements in a similar manner. Accordingly, it will be appreciated by those skilled in the art that the general principles above can be applied to embodiments where the joint is a hip joint.

In other embodiments, other image file-types are used such as STL, JPEG, GIF and TIF image files.

In other embodiments, the general principles above can be applied to all articulating implantable devices such as, but not limited to: shoulder replacements, spinal disc replacements, and ankle replacements.

In other embodiments, the general principles above can be applied to all implantable devices that are used in articulating joints, but where the implantable device is not itself an articulation replacement, including but not limited to: knee anterior cruciate ligament reconstruction and shoulder rotator cuff repair.

Interpretation

Wireless:

The invention may be embodied using devices conforming to other network standards and for other applications, including, for example other WLAN standards and other wireless standards. Applications that can be accommodated include IEEE 802.11 wireless LANs and links, and wireless Ethernet.

In the context of this document, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not. In the context of this document, the term "wired" and its derivatives may be used to describe circuits, devices, systems, methods, techniques, communications channels, etc., that may communicate data through the use of modulated electromagnetic radiation through a solid medium. The term does not imply that the associated devices are coupled by electrically conductive wires.

Processes:

Unless specifically stated otherwise, as apparent from the following discussions, it is appreciated that throughout the specification discussions utilizing terms such as "processing", "computing", "calculating", "determining", "analysing" or the like, refer to the action and/or processes of a computer or computing system, or similar electronic computing device, that manipulate and/or transform data represented as physical, such as electronic, quantities into other data similarly represented as physical quantities.

Processor:

In a similar manner, the term "processor" may refer to any device or portion of a device that processes electronic data, e.g., from registers and/or memory to transform that electronic data into other electronic data that, e.g., may be stored in registers and/or memory. A "computer" or a "computing device" or a "computing machine" or a "computing platform" may include one or more processors.

The methodologies described herein are, in one embodiment, performable by one or more processors that accept computer-readable (also called machine-readable) code containing a set of instructions that when executed by one or more of the processors carry out at least one of the methods described herein. Any processor capable of executing a set of instructions (sequential or otherwise) that specify actions to be taken are included. Thus, one example is a typical processing system that includes one or more processors. The processing system further may include a memory subsystem including main RAM and/or a static RAM, and/or ROM.

Computer-Readable Medium:

Furthermore, a computer-readable carrier medium may form, or be included in a computer program product. A computer program product can be stored on a computer usable carrier medium, the computer program product comprising a computer readable program means for causing a processor to perform a method as described herein.

Networked or Multiple Processors:

In alternative embodiments, the one or more processors operate as a standalone device or may be connected, e.g., networked to other processor(s), in a networked deployment, the one or more processors may operate in the capacity of a server or a client machine in server-client network environment, or as a peer machine in a peer-to-peer or distributed network environment. The one or more processors may form a web appliance, a network router, switch or bridge, or any machine capable of executing a set of instructions (sequential or otherwise) that specify actions to be taken by that machine.

Note that while some diagram(s) only show(s) a single processor and a single memory that carries the computer-readable code, those in the art will understand that many of the components described above are included, but not explicitly shown or described in order not to obscure the inventive aspect. For example, while only a single machine is illustrated, the term "machine" shall also be taken to include any collection of machines that individually or jointly execute a set (or multiple sets) of instructions to perform any one or more of the methodologies discussed herein.

Additional Embodiments

Thus, one embodiment of each of the methods described herein is in the form of a computer-readable carrier medium carrying a set of instructions, e.g., a computer program that are for execution on one or more processors. Thus, as will be appreciated by those skilled in the art, embodiments of the present invention may be embodied as a method, an apparatus such as a special purpose apparatus, an apparatus such as a data processing system, or a computer-readable carrier medium. The computer-readable carrier medium carries computer readable code including a set of instructions that when executed on one or more processors cause a processor or processors to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code embodied in the medium.

Carrier Medium:

The software may further be transmitted or received over a network via a network interface device. While the carrier medium is shown in an example embodiment to be a single medium, the term "carrier medium" should be taken to include a single medium or multiple media (e.g., a centralized or distributed database, and/or associated caches and servers) that store the one or more sets of instructions. The term "carrier medium" shall also be taken to include any medium that is capable of storing, encoding or carrying a set of instructions for execution by one or more of the processors and that cause the one or more processors to perform any one or more of the methodologies of the present invention. A carrier medium may take many forms, including but not limited to, non-volatile media, volatile media, and transmission media.

Implementation:

It will be understood that the steps of methods discussed are performed in one embodiment by an appropriate processor (or processors) of a processing (i.e., computer) system executing instructions (computer-readable code) stored in storage. It will also be understood that the invention is not limited to any particular implementation or programming technique and that the invention may be implemented using any appropriate techniques for implementing the functionality described herein. The invention is not limited to any particular programming language or operating system.

Means for Carrying Out a Method or Function

Furthermore, some of the embodiments are described herein as a method or combination of elements of a method that can be implemented by a processor of a processor device, computer system, or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

Connected

Similarly, it is to be noticed that the term connected, when used in the claims, should not be interpreted as being limitative to direct connections only. Thus, the scope of the expression a device A connected to a device B should not be limited to devices or systems wherein an output of device A is directly connected to an input of device B. It means that there exists a path between an output of A and an input of B which may be a path including other devices or means. "Connected" may mean that two or more elements are either in direct physical or electrical contact, or that two or more elements are not in direct contact with each other but yet still co-operate or interact with each other.

Embodiments

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description of Specific Embodiments are hereby expressly incorporated into this Detailed Description of Specific Embodiments, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Different Instances of Objects

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

Specific Details

In the description provided herein, numerous specific details are set forth. However, it is understood that embodiments of the invention may be practiced without these specific details. In other instances, well-known methods, structures and techniques have not been shown in detail in order not to obscure an understanding of this description.

Terminology

In describing the preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar technical purpose. Terms such as "forward", "rearward", "radially", "peripherally", "upwardly", "downwardly", and the like are used as words of convenience to provide reference points and are not to be construed as limiting terms.

Comprising and Including

In the claims which follow and in the preceding description of the invention, except where the context requires otherwise due to express language or necessary implication, the word "comprise" or variations such as "comprises" or "comprising" are used in an inclusive sense, i.e. to specify the presence of the stated features but not to preclude the presence or addition of further features in various embodiments of the invention.

Any one of the terms: including or which includes or that includes as used herein is also an open term that also means including at least the elements/features that follow the term, but not excluding others. Thus, including is synonymous with and means comprising.

Scope of Invention

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

Although the invention has been described with reference to specific examples, it will be appreciated by those skilled in the art that the invention may be embodied in many other forms.

INDUSTRIAL APPLICABILITY

It is apparent from the above, that the arrangements described are applicable to the healthcare medical device and medical software-as-a-service industries.

What is claimed is:

1. A method for modelling the alignment of an orthopaedic implant for a joint of a patient, the method comprising the computer-implemented steps of:
   being responsive to patient specific information data for deriving patient data, the patient specific information data being indicative of one or more dynamic characteristics; and
   being responsive to the patient data for providing 3D model data of the joint, such that the 3D model data shows the orthopaedic implant in an alignment configuration based on the patient specific information data.

2. A method as claimed in claim 1, wherein the one or more dynamic characteristics comprise a virtual prediction based on one or more of: joint kinematics data; joint loading data; and joint articulation behaviour data during desired post-implant activities.

3. A method as claimed in claim 2, wherein the virtual prediction comprises a computer model prediction.

4. A method as claimed in claim 1, wherein the patient specific information data is indicative of one or more static characteristics.

5. A method as claimed in claim 4, wherein the one or more static characteristics comprises one or more load bearing axes of a biomechanical reference frame.

6. A method as claimed in claim 5, wherein the one or more load bearing axes of the biomechanical reference frame comprises a primary load bearing axis.

7. A method as claimed in claim 4, wherein the one or more static characteristics comprise one or more load bearing axes of at least one reference frame of the group of biomechanical reference frames comprising: an acetabular reference frame, a femoral reference frame, a tibial reference frame, and a spinal reference frame.

8. A method as claimed in claim 1, wherein the patient specific information data comprises 2D imaging data.

9. A method as claimed in claim 1, wherein the patient specific information data comprises 3D imaging data.

10. A method as claimed in claim 1, wherein the patient specific information data comprises 4D imaging data.

11. A method as claimed in claim 1, wherein the patient specific information data comprises data being indicative of one or more physical characteristics of the patient.

12. A method as claimed in claim 11, wherein the one or more physical characteristics comprises one or more of: age data, gender data, height data, weight data, activity level data, BMI data, body condition data, and body shape data.

13. A method as claimed in claim 1, the method further comprising the computer-implemented or non-computer-implemented steps of:
    determining a set of possible alignment configurations according to the patient data and patient acquired data, the patient acquired data being indicative of one or more desired post-implant activities, the patient acquired data comprising post-implant activities preference data; and
    selecting an alignment configuration from the set of possible alignment configurations according to the post-implant activities preference data.

14. A method as claimed in claim 13, wherein the post-implant activities preference data is a preference ratio being indicative of comparative patient preference for the one or more desired post-implant activities.

15. A method as claimed in claim 13, the method further comprising the computer-implemented or non-computer-implemented step of:
    accessing a database of library alignment configuration data, wherein the alignment configuration is further selected according to the library alignment configuration data.

16. A method as claimed in claim 15, wherein the library alignment configuration data comprises data relating to a group of available orthopaedic implants for performing at least one of the one or more desired post-implant activities.

17. A method as claimed in claim 15, wherein the library alignment configuration data comprises data relating to a group of patients fitted with an orthopaedic implant for performing at least one of the one or more desired post-implant activities.

18. A computing device for modelling the alignment of an orthopaedic implant for a joint of a patient, the computing device comprising:
    a processor for processing digital data;
    a memory device for storing digital data including computer program code and being coupled to the processor via a bus; and
    a data interface for sending and receiving digital data and being coupled to the processor via the bus, wherein the processor is controlled by the computer program code to:
        receive, via the data interface, patient specific information data for deriving patient data, the patient specific information data being indicative of one or more dynamic characteristics;
        calculate patient data according to the patient specific information data; and
        calculate 3D model data of the joint according to the patient data, such that the 3D model data shows the orthopaedic implant in an alignment configuration.

19. A computing device as claimed in claim 18, wherein the one or more dynamic characteristics comprise a virtual prediction based on one or more of: joint kinematics data; joint loading data; and joint articulation behaviour data during desired post-implant activities.

20. A computing device as claimed in claim 19, wherein the virtual prediction comprises a computer model prediction.

21. A computing device as claimed in claim 18, wherein the patient specific information data is indicative of one or more static characteristics.

22. A computing device as claimed in claim 21, wherein the one or more static characteristics comprises one or more load bearing axes of a biomechanical reference frame.

23. A computing device as claimed in claim 22, wherein the one or more load bearing axes of the biomechanical reference frame comprises a primary load bearing axis.

24. A computing device as claimed in claim 21, wherein the one or more static characteristics comprise one or more load bearing axes of at least one reference frame of the group of biomechanical reference frames comprising: an acetabular reference frame, a femoral reference frame, a tibial reference frame, and a spinal reference frame.

25. A computing device as claimed in claim 18, wherein the patient specific information data comprises data being indicative of one or more physical characteristics of the patient.

26. A computing device as claimed in claim 25, wherein the one or more physical characteristics comprises one or more of: age data, gender data, height data, weight data, activity level data, BMI data, body condition data, and body shape data.

27. A computing device as claimed in claim 18, wherein the processor is further controlled by the computer program code to:
    receive, via the data interface, patient acquired data being indicative of one or more desired post-implant activities, the patient acquired data comprising post-implant activities preference data;
    calculate a set of possible alignment configurations according to the patient data and the patient acquired data; and
    select an alignment configuration from the set of possible alignment configurations according to the post-implant activities preference data.

28. A computing device as claimed in claim 27, wherein the post-implant activities preference data is a preference ratio being indicative of comparative patient preference for the one or more desired post-implant activities.

29. A computing device as claimed in claim 27, further comprising a database for storing digital data including library alignment configuration data, the database being coupled to the processor, wherein the processor is further controlled by the computer program code to:

load from the database, the library alignment configuration data, wherein the alignment configuration is further selected according to the library alignment configuration data.

30. A computing device as claimed in claim 29, wherein the library alignment configuration data comprises data relating to a group of available orthopaedic implants for performing at least one of the one or more desired post-implant activities.

31. A computing device as claimed in claim 29, wherein the library alignment configuration data comprises data relating to a group of patients fitted with an orthopaedic implant for performing at least one of the one or more desired post-implant activities.

32. A computer readable storage medium comprising computer program code instructions, being executable by a computer, for:

receiving, via a data interface, patient specific information data for deriving patient data, the patient specific information being indicative of one or more dynamic characteristics;

calculating patient data according to the patient specific information data; and calculating 3D model data of a joint according to the patient data, such that the 3D model data shows an orthopaedic implant in an alignment configuration.

33. A computer readable storage medium as claimed in claim 32, wherein the one or more dynamic characteristics comprise a virtual prediction based on one or more of: joint kinematics data; joint loading data; and joint articulation behaviour data during desired post-implant activities.

34. A computer readable storage medium as claimed in claim 33, wherein the virtual prediction comprises a computer model prediction.

35. A computer readable storage medium as claimed in claim 32, further comprising instructions for:

receiving, via the data interface, patient acquired data being indicative of one or more desired post-implant activities, the patient acquired data comprising post-implant activities preference data;

calculating a set of possible alignment configurations according to the patient data and the patient acquired data; and selecting an alignment configuration from the set of possible alignment configurations according to the post-implant activities preference data.

36. A computer readable storage medium as claimed in claim 35, wherein the post-implant activities preference data is a preference ratio being indicative of comparative patient preference for the one or more desired post-implant activities.

37. A client computing device comprising an interface for sending and receiving digital data and being coupled, across a data link, to a computing device as claimed in any one of claims 18 to 31, wherein the interface is adapted for sending and receiving digital data as referred to in any one of claims 18 to 31.

\* \* \* \* \*